(12) United States Patent
DiNinno et al.

(10) Patent No.: US 6,750,213 B2
(45) Date of Patent: Jun. 15, 2004

(54) ESTROGEN RECEPTOR MODULATORS

(75) Inventors: Frank P. DiNinno, Old Bridge, NJ (US); Jane Y. Wu, Marlboro, NJ (US); Seongkon Kim, Holmdel, NJ (US); Helen Y. Chen, Livingston, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/120,723

(22) Filed: Apr. 11, 2002

(65) Prior Publication Data

US 2002/0165226 A1 Nov. 7, 2002

Related U.S. Application Data

(63) Continuation-in-part of application No. PCT/US01/42735, filed on Oct. 15, 2001
(60) Provisional application No. 60/241,582, filed on Oct. 19, 2000.

(51) Int. Cl.$^7$ .............. A61K 31/395; A61K 31/55; A61P 5/00; C07D 405/00; C07D 409/00

(52) U.S. Cl. .............. 514/210.19; 514/63; 514/217.03; 514/318; 514/321; 514/422; 540/596; 546/14; 546/194; 546/197; 548/526; 548/950

(58) Field of Search .................. 514/63, 210.19, 514/217.03, 318, 321, 422; 540/596; 546/14, 194, 197; 548/526, 950

(56) References Cited

U.S. PATENT DOCUMENTS

| 5,919,814 A | 7/1999 | Guillaumet et al. ........ 514/432 |
| 6,013,607 A | 1/2000 | Otten et al. ................. 504/288 |

FOREIGN PATENT DOCUMENTS

| WO | WO 02 32373 | 4/2002 |

OTHER PUBLICATIONS

Miller et al., Targeting the Estrogen Receptor with SERMs, Annual Reports in Medicinal Chemistry, vol. 36, pp. 149–158, 2001.*
Paige et al., Estrogen Receptor (ER) Modulators Each Induce Distinct Conformational Changes in ER alpha and ER beta, Proceedings of the National Academy of Sciences, vol. 96, No. 7, pp. 3999–4004, Mar. 1999.*
Powles, T.J. "Breast Cancer Prevention", The Oncologist, vol. 7 (2002), pp. 60–64.
Park, W.C. and Jordan, V.C., "Selective estrogen receptor modulators (SERMS) and their roles in breast cancer prevention", Trends in Moleecular Medicine, vol. 8, No. 2 (Feb. 2002), pp. 82–88.
Wolff, A.C., "Use of SERMs for the Adjuvant Therapy of Early–Stage Breast Cancer", Annals NY Academy of Sciences, vol. 949 (Dec. 2001), pp. 80–88.

Steiner, M.S. et al., "Selective Estrogen Receptor Modulators for the Chemoprevention of Prostate Cancer", Urology, vol. 57 (Supplement 4A) (Apr. 2001), pp. 68–72.
Campisi, C., et al., "Complete resolution of breast cancer bone metastasis through the use of beta–Interferon and Tamoxifen", Eur J Gynaecol Oncology, vol. 14, No. 6 (1993), pp. 479–483.
Ribiero, G. and Swindell, R., "Adjuvant Tamoxifen for male breast cancer (MBC)", Br. J. Cancer (1992), vol. 65, pp. 252–254.
Jordan, V.C., et al., "Selective Estrogen Receptor Modulation and Reduction in Risk of Breast Cancer, Osteoporosis, and Coronary Heart Disease", (Nat'l Cancer Inst., vol. 93, No. 19 (Oct. 2001), pp. 1449–1457.
Bjarnason, N.H., et al., "Six and twelve month changes in bone turnover are related to reduction in vertebral fracture risk during 3 years of raloxifene treatment in postmenopausal osteoporosis", Osteoporosis Int. (2001), vol. 12, pp. 922–930.
Fentiman, I.S., et al., Tamoxifen Protects Against Steroid––induced Bone Loss:, Eur. J. Cancer, vol. 28, No. 2/3(1992), pp. 684–685.
Rodan, G. A., et al., "Therapeutic Approaches to Bone Diseases", Science (Sep. 2000), vol. 289, pp. 1508–1514.
Palomba, S., et al., "Effects of raloxifene treatment on uterine leiomyomas in postmenopausal women", Fertility and Sterility, vol. 76, No. 1 (Jul. 2001), pp. 38–43.
Picard, F., et al., "Effects of the estrogen antagonist EM–652.HCl on energy balance and lipid metabolism in ovariectomized rats", Int. Journal of Obesity (2000), vol. 24, pp. 830–840.
Badger, A.M., et al., "Idoxifene, a Novel Selective Estrogen Receptor Modulator, is Effective in a Rat Model of Adjuvant–Induced Arthritis", Journ. of Pharmacol and Experimental Ther. (Dec. 1999), vol. 291, No. 3, pp. 1380–1386.
Goldstein, S.R., "The Effect of SERMs on the Endometrium", Annals NY Academy of Sciences, vol. 949 (2001), pp. 237–242.

(List continued on next page.)

*Primary Examiner*—Brenda Coleman
(74) *Attorney, Agent, or Firm*—Nicole M. Beeler; Mark R. Daniel

(57) ABSTRACT

The present invention relates to compounds and derivatives thereof, their synthesis, and their use as estrogen receptor modulators. The compounds of the instant invention are ligands for estrogen receptors and as such may be useful for treatment or prevention of a variety of conditions related to estrogen functioning including: bone loss, bone fractures, osteoporosis, cartilage degeneration, endometriosis, uterine fibroid disease, hot flashes, increased levels of LDL cholesterol, cardiovascular disease, impairment of cognitive functioning, cerebral degenerative disorders, restenosis, gynecomastia, vascular smooth muscle cell proliferation, obesity, incontinence, and cancer, in particular of the breast, uterus and prostate.

24 Claims, No Drawings

OTHER PUBLICATIONS

Goldstein, S.R., "Raloxifene Effect on Frequency of Surgery for Pelvic Floor Relaxation", The American College of Obstet. and Gynecol., vol. 98, No. 1 (Jul. 2001), pp. 91–96.

Nuttall, M.E., et al., "Idoxifen: A Novel Selective Estrogen Receptor Modulator Prevents Bone Loss and Lowers Cholesterol Levels in Ovariectomized Rats and Decreases Uterine Weight in Intact Rats", Endocrinology (Dec. 1998), vol. 139, No. 12, pp. 5224–5234.

Guzzo, J.A., "Selective Estrogen Receptor Modulators—a New Age of Estrogens in Cardiovascular Disease?" Clin. Cardiol (2000), vol. 23, No. 1, pp. 15–17.

Simoncini, T. and Genazzani, A.R., "Direct vascular effects of estrogen and selective estrogen receptor modulators", Curr. Opinion in Obsterics and Gynecology (Jun. 2000), vol. 12, No. 3, pp. 181–187.

Yaffe, K., et al., "Cognitive Function in Postmenopausal Women Treated with Raloxifene", N. Engl. Journal of Medicine, vol. 344, No. 16, (Apr. 2001), pp. 1207–1213.

Bendinskas, et al—Bioconjugate Chemistry, vol. 9, No. 5, pp. 555–563, 1998.

* cited by examiner

ESTROGEN RECEPTOR MODULATORS

CROSS-REFERENCE TO RELATED APPLICATIONS

This application is a continuation-in-part of PCT/US01/42735, filed Oct. 15, 2001 which claims the benefit of U.S. Provisional Application No. 60/241,582 filed Oct. 19, 2000.

BACKGROUND OF THE INVENTION

Naturally occurring and synthetic estrogens have broad therapeutic utility, including: relief of menopausal symptoms, treatment of acne, treatment of dysmenorrhea and dysfunctional uterine bleeding, treatment of osteoporosis, treatment of hirsutism, treatment of prostatic cancer, treatment of hot flashes and prevention of cardiovascular disease. Because estrogen is very therapeutically valuable, there has been great interest in discovering compounds that mimic estrogen-like behavior in estrogen responsive tissues.

For example, estrogen-like compounds would be beneficial in the treatment and prevention of bone loss. Bone loss occurs in a wide range of subjects, including women that are post-menopausal or have had a hysterectomy, patients who were or are currently being treated with corticosteroids, and patient's having gonadal dysgenesis. The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid-induced osteoporosis. All of these conditions are characterized by bone loss, resulting from an imbalance between bone resorption, i.e. breakdown, and bone formation, which continues throughout life at the rate of about 14% per year on the average. However, the rate of bone turnover differs from site to site, for example, it is higher in the trabecular bone of the vertebrae and the alveolar bone in the jaws than in the cortices of the long bones. The potential for bone loss is directly related to turnover and can amount to over 5% per year in vertebrae immediately following menopause, a condition which leads to increased fracture risk.

In the U.S., there are currently about 20 million people with detectable fractures of the vertebrae due to osteoporosis. In addition, there are about 250,000 hip fractures per year attributed to osteoporosis. This clinical situation is associated with a 12% mortality rate within the first two years, while 30% of the patients require nursing home care after the fracture.

Osteoporosis affects approximately 20 to 25 million postmenopausal women in the U.S. alone. It has been theorized that the rapid loss of bone mass in these women is due to the cessation of estrogen production of the ovaries. Since studies have shown that estrogen slows the reduction of bone mass due to osteoporosis, estrogen replacement therapy is a recognized treatment for post-menopausal osteoporosis.

In addition to bone mass, estrogen appears to have an effect on the biosynthesis of cholesterol and cardiovascular health. Statistically, the rate of occurrence of cardiovascular disease is roughly equal in postmenopausal women and men; however, premenopausal women have a much lower incidence of cardiovascular disease than men. Because postmenopausal women are estrogen deficient, it is believed that estrogen plays a beneficial role in preventing cardiovascular disease. The mechanism is not well understood, but evidence indicates that estrogen can upregulate the low density lipid (LDL) cholesterol receptors in the liver to remove excess cholesterol.

Postmenopausal women given estrogen replacement therapy experience a return of lipid levels to concentrations comparable to levels associated with the premenopausal state. Thus, estrogen replacement therapy could be an effective treatment for such disease. However, the side effects associated with long term estrogen use limit the use of this alternative.

Other disease states that affect postmenopausal women include estrogen-dependent breast cancer and uterine cancer. Anti-estrogen compounds, such as tamoxifen, have commonly been used as chemotherapy to treat breast cancer patients. Tamoxifen, a dual antagonist and agonist of estrogen receptors, is beneficial in treating estrogen-dependent breast cancer. However, treatment with tamoxifen is less than ideal because tamoxifen's agonist behavior enhances its unwanted estrogenic side effects. For example, tamoxifen and other compounds that agonize estrogen receptors tend to increase cancer cell production in the uterus. A better therapy for such cancers would be an anti-estrogen compound that has negligible or nonexistent agonist properties.

Although estrogen can be beneficial for treating pathologies such as bone loss, increased lipid levels, and cancer, long-term estrogen therapy has been implicated in a variety of disorders, including an increase in the risk of uterine and endometrial cancers. These and other side effects of estrogen replacement therapy are not acceptable to many women, thus limiting its use.

Alternative regimens, such as a combined progestogen and estrogen dose, have been suggested in an attempt to lessen the risk of cancer. However, such regimens cause the patient to experience withdrawal bleeding, which is unacceptable to many older women. Furthermore, combining estrogen with progestogen reduces the beneficial cholesterol-lowering effect of estrogen therapy. In addition, the long term effects of progestogen treatment are unknown.

In addition to post-menopausal women, men suffering from prostatic cancer can also benefit from anti-estrogen compounds. Prostatic cancer is often endocrine-sensitive; androgen stimulation fosters tumor growth, while androgen suppression retards tumor growth. The administration of estrogen is helpful in the treatment and control of prostatic cancer because estrogen administration lowers the level of gonadotropin and, consequently, androgen levels.

The estrogen receptor has been found to have two forms: ER$\alpha$ and ER$\beta$. Ligands bind differently to these two forms, and each form has a different tissue specificity to binding ligands. Thus, it is possible to have compounds that are selective for ER$\alpha$ or ER$\beta$, and therefore confer a degree of tissue specificity to a particular ligand.

What is needed in the art are compounds that can produce the same positive responses as estrogen replacement therapy without the negative side effects. Also need are estrogen-like compounds that exert selective effects on different tissues of the body.

The compounds of the instant invention are ligands for estrogen receptors and as such may be useful for treatment or prevention of a variety of conditions related to estrogen functioning including: bone loss, bone fractures, osteoporosis, glucocorticoid induced osteoporosis, Paget's disease, abnormally increased bone turnover, periodontal disease, tooth loss, rheumatoid arthritis, osteoarthritis, periprosthetic osteolysis, osteogenesis imperfecta, metastatic bone disease, hypercalcemia of malignancy, and multiple myeloma, cartilage degeneration, endometriosis, uterine fibroid disease, cancer of the breast, uterus or prostate, hot flashes, cardiovascular disease, impairment of cognitive function, cerebral degenerative disorders, restenosis, gynecomastia, vascular smooth muscle cell proliferation, obesity and incontinence.

SUMMARY OF THE INVENTION

The present invention relates to compounds that are capable of treating and/or preventing a variety of conditions related to estrogen functioning. One embodiment of the present invention is illustrated by a compound of Formula I, and the pharmaceutically acceptable salts and stereoisomers thereof:

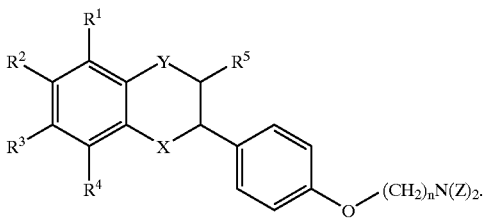

I

DETAILED DESCRIPTION OF THE INVENTION

The present invention relates to compounds useful as estrogen receptor modulators. Compounds of the present invention are described by the following chemical formula:

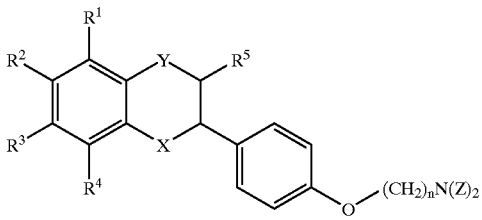

wherein $R^1$, $R^2$, $R^3$, and $R^4$ are each independently selected from the group consisting of hydrogen, $C_{1-5}$ alkyl, $C_{3-8}$ cycloalkyl, $C_{2-5}$ alkenyl, $C_{2-5}$ alkynyl, $C_{3-8}$ cycloalkenyl, phenyl, heteroaryl, heterocyclyl, $CF_3$, —$OR^6$, halogen, $C_{1-5}$ alkylthio, thiocyanato, cyano, —$CO_2H$, —$COOC_{1-5}$ alkyl, —$COC_{1-5}$ alkyl, —$CONZ_2$, —$SO_2NZ_2$, and —$SO_2C_{1-5}$ alkyl, wherein said alkyl, alkenyl, alkynyl, cycloalkyl, cycloalkenyl, phenyl, heteroaryl and heterocyclyl can be optionally substituted with $C_{1-5}$ alkyl, $C_{3-8}$ cycloalkyl, $CF_3$, phenyl, heteroaryl, heterocyclyl, —$OR^6$, halogen, amino, $C_{1-5}$ alkylthio, thiocyanato, cyano, —$CO_2H$, —$COOC_{1-5}$ alkyl, —$COC_{1-5}$ alkyl, —$CONZ_2$, —$SO_2NZ_2$ or —$SO_2C_{1-5}$ alkyl;

$R^5$ is selected from the group consisting of $C_{1-5}$ alkyl, $C_{3-8}$ cycloalkyl, $C_{2-5}$ alkenyl, $C_{2-5}$ alkynyl, $C_{3-8}$ cycloalkenyl, phenyl, heteroaryl and heterocyclyl, wherein said alkyl, cycloalkyl, alkenyl, alkynyl, cycloalkenyl, phenyl, heteroaryl and heterocyclyl can be optionally substituted with $C_{1-5}$ alkyl, $C_{3-8}$ cycloalkyl, $CF_3$, phenyl, heteroaryl, heterocyclyl, —$OR^6$, halogen, amino, $C_{1-5}$ alkylthio, thiocyanato, cyano, —$CO_2H$, —$COOC_{1-5}$ alkyl, —$COC_{1-5}$ alkyl, —$CONZ_2$, —$SO_2NZ_2$ or —$SO_2C_{1-5}$ alkyl;

X and Y are each independently selected from the group consisting of oxygen, sulfur, sulfoxide and sulfone;

$R^6$ is selected from the group consisting of hydrogen, $C_{1-5}$ alkyl, benzyl, methoxymethyl, triorganosilyl, $C_{1-5}$ alkylcarbonyl, alkoxycarbonyl and $CONZ_2$;

each Z is independently selected from the group consisting of hydrogen, $C_{1-5}$ alkyl, trifluoromethyl, wherein said alkyl can be optionally substituted with $C_{1-5}$ alkyl, $CF_3$, —$OR^6$, halogen, amino, $C_{1-5}$ alkylthio, thiocyanato, cyano, —$CO_2H$, —$COOC_{1-5}$ alkyl, —$COC_{1-5}$ alkyl, —$CONV_2$, —$SO_2NV_2$ or —$SO_2C_{1-5}$ alkyl;

both Zs and the nitrogen to which they are attached may be taken together to form a 3–8 membered ring, said ring may optionally contain atoms selected from the group consisting of carbon, oxygen, sulfur, and nitrogen, wherein said ring may either be saturated or unsaturated, and the carbon atoms of said ring maybe optionally substituted with one to three substituents selected from the group consisting of $C_{1-5}$ alkyl, $CF_3$, —$OR^6$, halogen, amino, $C_{1-5}$ alkylthio, thiocyanato, cyano, —$CO_2H$, —$COOC_{1-5}$ alkyl, —$COC_{1-5}$ alkyl, —$CONV_2$, —$SO_2NV_2$, and —$SO_2C_{1-5}$ alkyl;

each V is independently selected from the group consisting of $C_{1-5}$ alkyl, $CF_3$, —$OR^6$, halogen, amino, $C_{1-5}$ alkylthio, thiocyanato, cyano, —$CO_2H$, —$COOC_{1-5}$ alkyl, —$COC_{1-5}$ alkyl, and —$SO_2C_{1-5}$ alkyl;

each n is independently an integer from one to five;

or a pharmaceutically acceptable salt or stereoisomer thereof.

In one class of compounds of the present invention, X is Oxygen, and Y is Sulfur. In another class of compounds of the present invention, X is Oxygen, and Y is Oxygen. In another class of compounds of the present invention, X is Sulfur, and Y is Sulfur.

In one class of compounds of the present invention, $R^1$, $R^2$, $R^3$ and $R^4$ are each independently selected from the group consisting of hydrogen, $C_{1-5}$ alkyl, $C_{3-8}$ cycloalkyl, $C_{1-5}$ alkenyl, $C_{1-5}$ alkynyl, —$OR^6$ and halogen.

In one class of compounds of the present invention $R^5$ is selected from the group consisting of $C_{3-8}$ cycloalkyl, phenyl, heteroaryl and heterocyclyl wherein said cycloalkyl, phenyl, heteroaryl or heterocyclyl can be optionally substituted with —$OR^6$ and halogen. In a preferred class of the present invention $R^5$ is phenyl and can be optionally substituted with —$OR^6$ and halogen.

In one class of compounds of the present invention, $R^6$ is selected from the group consisting of hydrogen, $C_{1-5}$ alkyl, benzyl, methoxymethyl and triisopropylsilyl. In a preferred class, $R^6$ is hydrogen.

In one class of compounds of the present invention, both Zs and the nitrogen to which they are attached are taken together to form a 3–8 membered ring, wherein said ring optionally contains atoms selected from the group consisting of carbon, oxygen, sulfur, and nitrogen, and said ring may either be saturated or unsaturated, and the carbon atoms of said ring maybe optionally substituted with one to three substituents selected from the group consisting of $C_{1-5}$ alkyl, $CF_3$, —$OR^6$, halogen, amino, $C_{1-5}$ alkylthio, thiocyanato, cyano, —$CO_2H$, —$COOC_{1-5}$ alkyl, —$COC_{1-5}$ alkyl, —$CONV_2$, —$SO_2NV_2$, and —$SO_2C_{1-5}$ alkyl. Each V is independently selected from the group consisting of $C_{1-5}$ alkyl, $CF_3$, —$OR^6$, halogen, amino, $C_{1-5}$ alkylthio, thiocyanato, cyano, —$CO_2H$, —$COOC_{1-5}$ alkyl, —$COC_{1-5}$ alkyl, and —$SO_2C_{1-5}$ alkyl. Examples of the heterocycles that can thus be formed include, but are not limited five or six membered rings containing at least one nitrogen, which is optionally substituted with one or more substituents as described above. A preferred embodiment is when optionally substituted pyrolidinyl is formed.

Non-limiting examples of the present invention include:
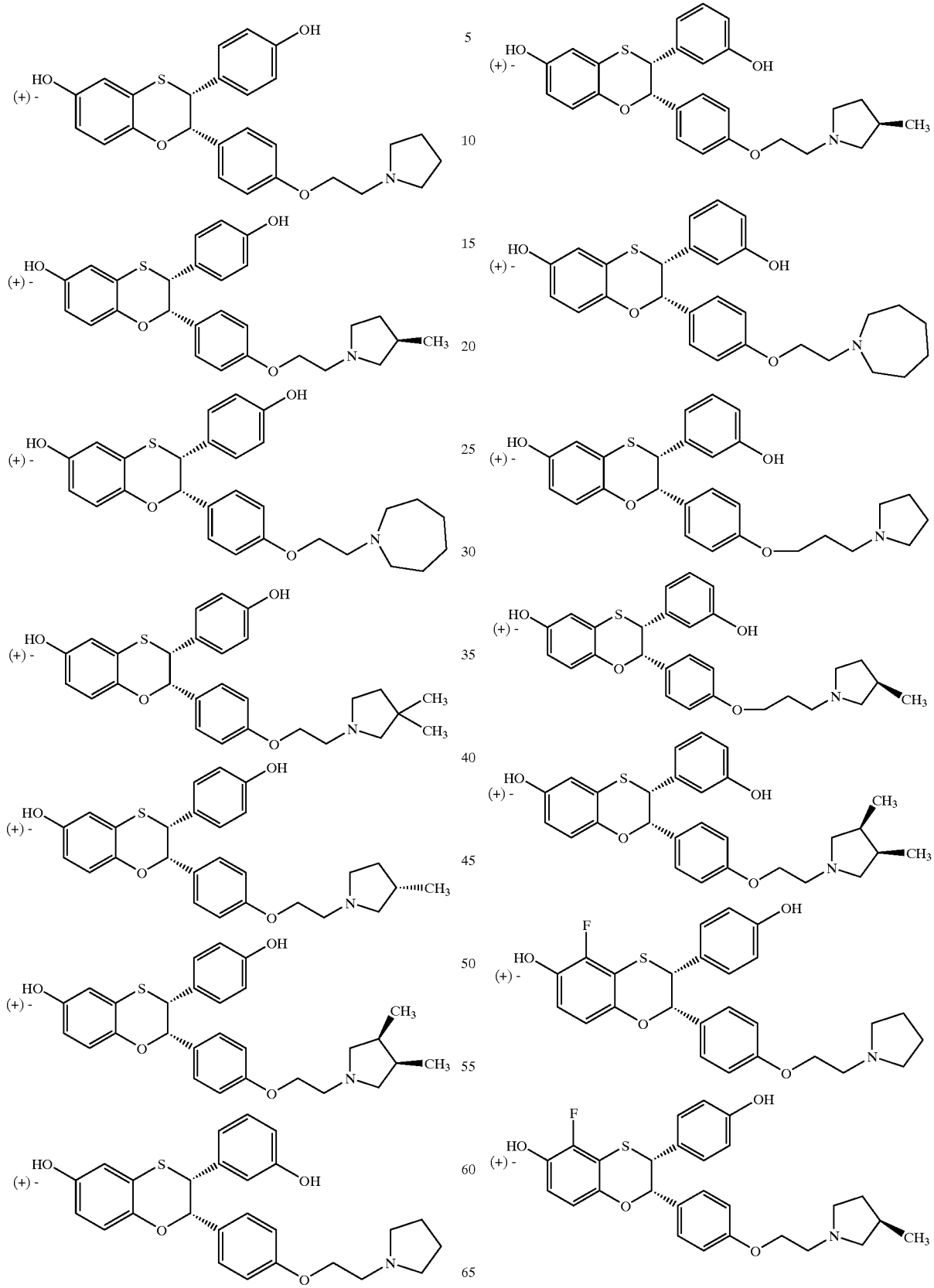

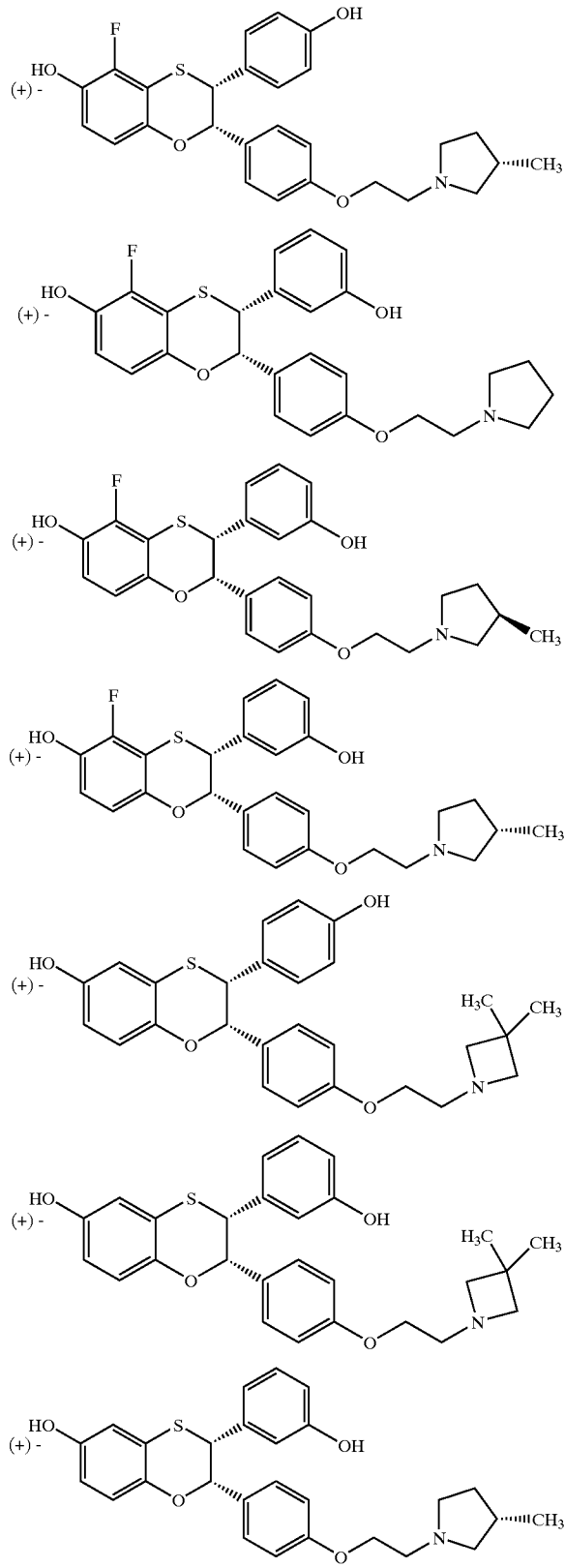
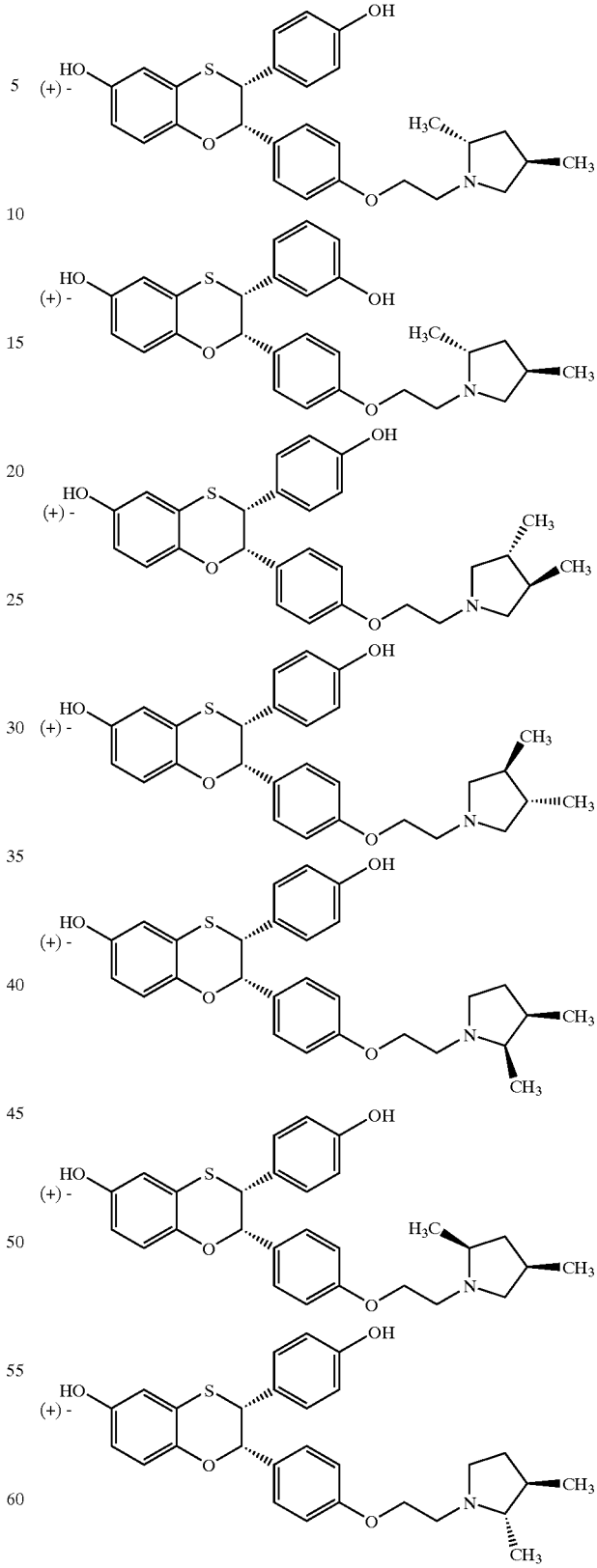

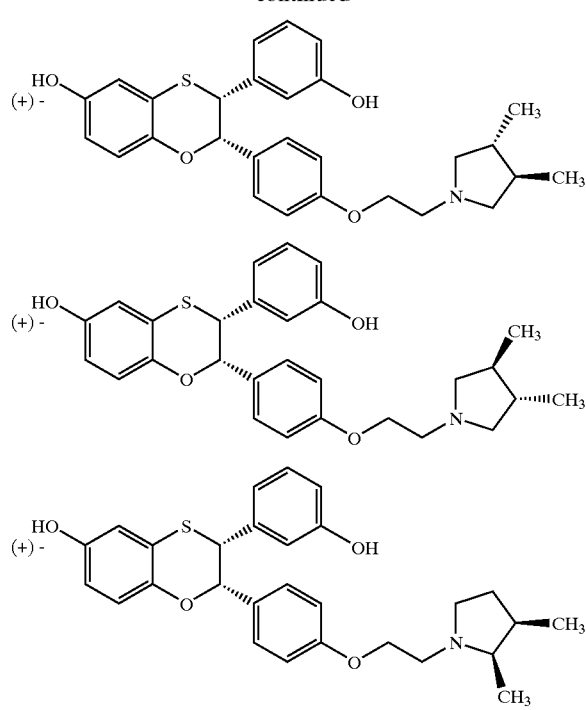
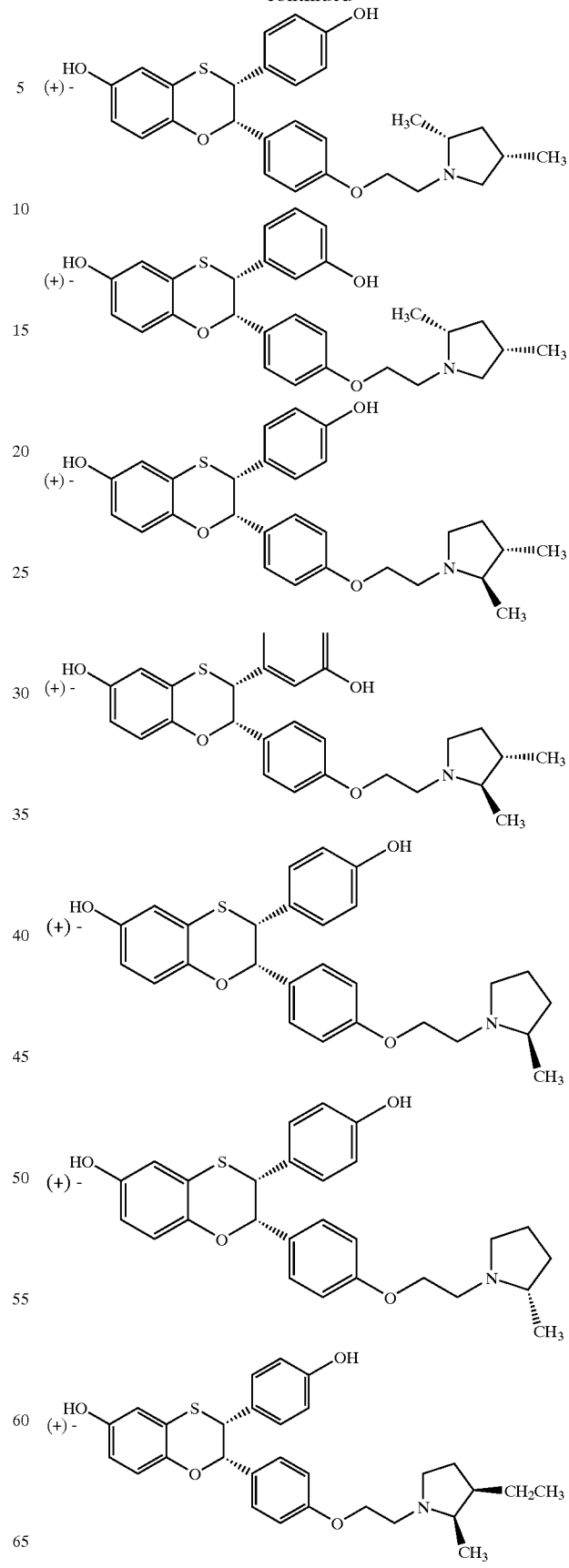

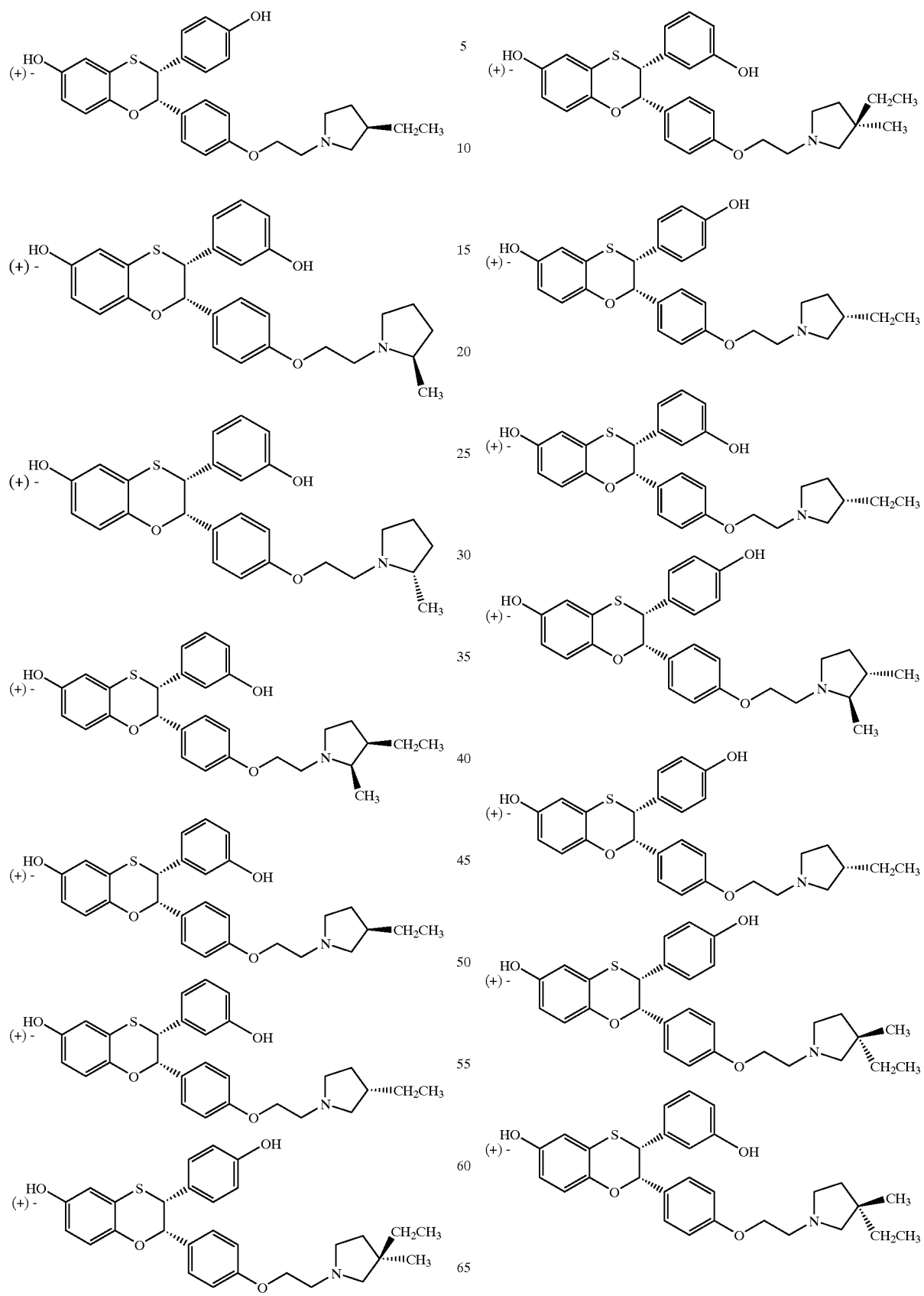

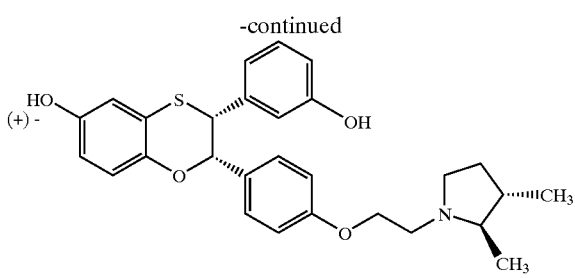

and the pharmaceutically acceptable salts and stereoisomers thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. The present invention also relates to methods for making the pharmaceutical compositions of the present invention. The present invention is also related to processes and intermediates useful for making the compounds and pharmaceutical compositions of the present invention. These and other aspects of the invention will be apparent from the teachings contained herein.

Utilities

The compounds of the present invention are selective modulators of estrogen receptors and are therefore useful to treat or prevent a variety of diseases and conditions related to estrogen receptor functioning in mammals, preferably humans.

"A variety of diseases and conditions related to estrogen receptor functioning" includes, but is not limited to, bone loss, bone fractures, osteoporosis, glucocorticoid induced osteoporosis, Paget's disease, abnormally increased bone turnover, periodontal disease, tooth loss, rheumatoid arthritis, osteoarthritis, periprosthetic osteolysis, osteogenesis imperfecta, metastatic bone disease, hypercalcemia of malignancy, and multiple myeloma, cartilage degeneration, endometriosis, uterine fibroid disease, cancer of the breast, uterus or prostate, hot flashes, cardiovascular disease, impairment of cognitive function, cerebral degenerative disorders, restenosis, gynecomastia, vascular smooth muscle cell proliferation, obesity and incontinence. In treating such conditions with the instantly claimed compounds, the required therapeutic amount will vary according to the specific disease and is readily ascertainable by those skilled in the art. Although both treatment and prevention are contemplated by the scope of the invention, the treatment of these conditions is the preferred use.

The present invention also relates to methods for eliciting an estrogen receptor modulating effect in a mammal in need thereof by administering the compounds and pharmaceutical compositions of the present invention.

The present invention also relates to methods for eliciting an estrogen receptor antagonizing effect in a mammal in need thereof by administering the compounds and pharmaceutical compositions of the present invention. The estrogen receptor antagonizing effect can be either an ERα antagonizing effect, and ERβ antagonizing effect or a mixed ERα and ERβ antagonizing effect.

The present invention also relates to methods for eliciting an estrogen receptor agonizing effect in a mammal in need thereof by administering the compounds and pharmaceutical compositions of the present invention. The estrogen receptor agonizing effect can be either an ERα agonizing effect, and ERβ agonizing effect or a mixed ERα and ERβ agonizing effect.

The present invention also relates to methods for treating or preventing disorders related to estrogen functioning, bone loss, bone fractures, osteoporosis, glucocorticoid induced osteoporosis, Paget's disease, abnormally increased bone turnover, periodontal disease, tooth loss, rheumatoid arthritis, osteoarthritis, periprosthetic osteolysis, osteogenesis imperfecta, metastatic bone disease, hypercalcemia of malignancy, and multiple myeloma, cartilage degeneration, endometriosis, uterine fibroid disease, cancer of the breast, uterus or prostate, hot flashes, cardiovascular disease, impairment of cognitive function, cerebral degenerative disorders, restenosis, gynecomastia, vascular smooth muscle cell proliferation, obesity and incontinence in a mammal in need thereof by administering the compounds and pharmaceutical compositions of the present invention. Exemplifying the invention is a method of treating or preventing osteoporosis. Exemplifying the invention is a method of treating or preventing bone loss. Exemplifying the invention is a method of treating or preventing metastatic bone disease. Exemplifying the invention is a method of treating or preventing cancer. Exemplifying the invention is a method of treating or preventing cardiovascular disease.

An embodiment of the invention is a method for treating or preventing cancer, especially of the breast, uterus or prostate, in a mammal in need thereof by administering the compounds and pharmaceutical compositions of the present invention. The utility of SERMs for the treatment of breast, uterine or prostate cancer is known in the literature, see T. J. Powles, "Breast cancer prevention," Oncologist 2002; 7(1):60–4; Park, W. C. and Jordan, V. C., "Selective estrogen receptor modulators (SERMS) and their roles in breast cancer prevention." Trends Mol Med. February 2002; 8(2):82–8; Wolff, A. C. et al., "Use of SERMs for the adjuvant therapy of early-stage breast cancer," Ann N Y Acad Sci. December 2001; 949:80–8; Steiner, M. S. et al., "Selective estrogen receptor modulators for the chemoprevention of prostate cancer," Urology April 2001; 57(4 Suppl 1):68–72.

Another embodiment of the invention is a method of treating or preventing metastatic bone disease in a mammal in need thereof by administering to the mammal a therapeutically effective amount of any of the compounds or pharmaceutical compositions described above. The utility of SERMS in the treatment of metastatic bone disease is known in the literature, see, Campisi, C. et al., "Complete resoultion of breast cancer bone metastasis through the use of beta-interferon and tamoxifen," Eur J Gynaecol Oncol 1993;14 (6):479–83.

Another embodiment of the invention is a method of treating or preventing gynecomastia in a mammal in need thereof by administering to the mammal a therapeutically effective amount of any of the compounds or pharmaceutical compositions described above. The utility of SERMS in the treatment of gynecomastia is known in the literature, see, Ribeiro, G. and Swindell R., "Adjuvant tamoxifen for male breast cancer." Br J Cancer 1992;65:252–254; Donegan, W., "Cancer of the Male Breast," JGSM Vol. 3, Issue 4, 2000.

Another embodiment of the invention is a method of treating or preventing post-menopausal osteoporosis, glucocorticoid osteoporosis, hypercalcemia of malignancy, bone loss and bone fractures in a mammal in need thereof by administering to the mammal a therapeutically effective amount of any of the compounds or pharmaceutical compositions described above. The utility of SERMs to treat or prevent osteoporosis, hypercalcemia of malignancy, bone loss or bone fractures is known in the literature, see Jordan, V. C. et al., "Selective estrogen receptor modulation and reduction in risk of breast cancer, osteoporosis and coronary heart disease," Natl Cancer Inst October 2001; 93(19):1449–57; Bjarnason, N H et al., "Six and twelve month changes in bone turnover are realted to reduction in vertebral fracture risk during 3 years of raloxifene treatment in postemenopausal osteoporosis," Osteoporosis Int 2001; 12(11):922–3; Fentiman I. S., "Tamoxifen protects against steroid-induced bone loss," Eur J Cancer 28:684–685 (1992); Rodan, G. A. et al., "Therapeutic Approaches to Bone Diseases," Science Vol 289, Sep. 1, 2000.

Another embodiment of the invention is a method of treating of preventing periodontal disease or tooth loss in a mammal in need thereof by administering to the mammal a therapeutically effective amount of any of the compounds or pharmaceutical compositions described above. The use of SERMs to treat periodontal disease or tooth loss in a mammal is known in the literature, see Rodan, G. A. et al., "Therapeutic Approaches to Bone Diseases," Science Vol 289, Sep. 1, 2000 pp. 1508–14.

Another embodiment of the invention is a method of treating of preventing Paget's disease in a mammal in need thereof by administering to the mammal a therapeutically effective amount of any of the compounds or pharmaceutical compositions described above. The use of SERMs to treat Paget's disease in a mammal is known in the literature, see Rodan, G. A. et al., "Therapeutic Approaches to Bone Diseases," Science Vol 289, Sep. 1, 2000 pp. 1508–14.

Another embodiment of the invention is a method of treating or preventing uterine fibroid disease in a mammal in need thereof by administering to the mammal a therapeutically effective amount of any of the compounds or pharmaceutical compositions described above. The use of SERMS to treat uterine fibroids, or uterine leiomyomas, is known in the literature, see Palomba, S., et al, "Effects of raloxifene treatment on uterine leiomyomas in postmenopausal women," Fertil Steril. July 2001; 76(1):38–43.

Another embodiment of the invention is a method of treating or preventing obesity in a mammal in need thereof by administering to the mammal a therapeutically effective amount of any of the compounds or pharmaceutical compositions described above. The use of SERMs to treat obesity is known in the literature, see Picard, F. et al., "Effects of the estrogen antagonist EM-652.HCl on energy balance and lipid metabolism in ovariectomized rats," Int J Obes Relat Metab Disord. July 2000; 24(7):830–40.

Another embodiment of the invention is a method of treating or preventing cartilage degeneration, rheumatoid arthritis or osteoarthritis in a mammal in need thereof by administering to the mammal a therapeutically effective amount of any of the compounds or pharmaceutical compositions described above. The use of SERMs to treat cartilage degeneration, rheumatoid arthritis or osteoarthritis is known in the literature, see Badger, A. M. et al., "Idoxifene, a novel selective estrogen receptor modulator, is effective in a rat model of adjuvant-induced arthritis." J Pharmacol Exp Ther. December 1999;291(3):1380–6.

Another embodiment of the invention is a method of treating or preventing endometriosis in a mammal in need thereof by administering to the mammal a therapeutically effective amount of any of the compounds or pharmaceutical compositions described above. The use of SERMs to treat endometriosis is known in the art, see Steven R. Goldstein, "The Effect of SERMs on the Endometrium," Annals of the New York Academy of Sciences 949:237–242 (2001).

Another embodiment of the invention is a method of treating or preventing urinary incontinence in a mammal in need thereof by administering to the mammal a therapeutically effective amount of any of the compounds or pharmaceutical compositions described above. The use of SERMs to treat urinary incontinence is known in the art, see, Goldstein, S. R., "Raloxifene effect on frequency of surgery for pelvic floor relaxation," Obstet Gynecol. July 2001;98(1):91–6.

Another embodiment of the invention is a method of treating or preventing cardiovascular disease, restenosis, lowering levels of LDL cholesterol and inhibiting vascular smooth muscle cell proliferation in a mammal in need thereof by administering to the mammal a therapeutically effective amount of any of the compounds or pharmaceutical compositions described above. The utility of SERMs in treating or preventing cardiovascular disease, restenosis, lowering levels of LDL cholesterol and inhibiting vascular smooth muscle cell proliferation is known in the art, see Nuttall, ME et al., "Idoxifene: a novel selective estrogen receptor modulator prevents bone loss and lowers cholesterol levels in ovariectomized rats and decreases uterine weight in intact rats," Endocrinology December 1998;139(12):5224–34; Jordan, V. C. et al., "Selective estrogen receptor modulation and reduction in risk of breast cancer, osteoporosis and coronary heart disease," Natl Cancer Inst October 2001; 93(19): 1449–57; Guzzo J A., "Selective estrogen receptor modulators—a new age of estrogens in cardiovascular disease?," Clin Cardiol January 2000;23(1):15–7; Simoncini T, Genazzani A R., "Direct vascular effects of estrogens and selective estrogen receptor modulators," Curr Opin Obstet Gynecol June 2000;12(3):181–7.

Another embodiment of the invention is a method of treating or preventing the impairment of cognitive functioning or cerebral degenerative disorders in a mammal in need thereof by administering to the mammal a therapeutically effective amount of any of the compounds or pharmaceutical compositions described above. The utility of SERMs to prevent the impairment of cognitive functioning is known in the art, see Yaffe, K., K. Krueger, S. Sarkar, et al. 2001. Cognitive function in postmenopausal women treated with raloxifene. N. Eng. J. Med. 344: 1207–1213.

Exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone loss, bone resorption, bone fractures, metastatic bone disease and/or disorders related to estrogen functioning.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

In the case of tablets for oral use, carriers which are commonly used include lactose and corn starch, and lubricating agents, such as magnesium stearate, are commonly added. For oral administration in capsule form, useful diluents include lactose and dried corn starch. For oral use of a therapeutic compound according to this invention, the selected compound may be administered, for example, in the form of tablets or capsules, or as an aqueous solution or suspension. For oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The instant compounds are also useful in combination with known agents useful for treating or preventing bone loss, bone fractures, osteoporosis, glucocorticoid induced osteoporosis, Paget's disease, abnormally increased bone turnover, periodontal disease, tooth loss, rheumatoid arthritis, osteoarthritis, periprosthetic osteolysis, osteogenesis imperfecta, metastatic bone disease, hypercalcemia of malignancy, and multiple myeloma, cartilage degeneration, endometriosis, uterine fibroid disease, cancer of the breast, uterus or prostate, hot flashes, cardiovascular disease, impairment of cognitive function, cerebral degenerative disorders, restenosis, gynecomastia, vascular smooth muscle cell proliferation, obesity and incontinence. Combinations of the presently disclosed compounds with other agents useful in treating or preventing osteoporosis or other bone disorders are within the scope of the invention. A person of ordinary skill in the art would be able to discern which combinations of agents would be useful based on the particular characteristics of the drugs and the disease involved. Such agents include the following: an organic bisphosphonate; a cathepsin K inhibitor; an estrogen or an estrogen receptor modulator; an androgen receptor modulator; an inhibitor of osteoclast proton ATPase; an inhibitor of HMG-CoA reductase; an integrin receptor antagonist; an osteoblast anabolic agent, such as PTH; calcitonin; Vitamin D or a synthetic Vitamin D analogue; selective serotonin reuptake inhibitors (SSRIs); and the pharmaceutically acceptable salts and mixtures thereof. A preferred combination is a compound of the present invention and an organic bisphosphonate. Another preferred combination is a compound of the present invention and a cathepsin K inhibitor. Another preferred combination is a compound of the present invention and an estrogen. Another preferred combination is a compound of the present invention and an androgen receptor modulator. Another preferred combination is a compound of the present invention and an osteoblast anabolic agent.

"Organic bisphosphonate" includes, but is not limited to, compounds of the chemical formula

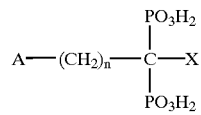

wherein n is an integer from 0 to 7 and wherein A and X are independently selected from the group consisting of H, OH, halogen, $NH_2$, SH, phenyl, C1–C30 alkyl, C3–C30 branched or cycloalkyl, bicyclic ring structure containing two or three N, C1–C30 substituted alkyl, C1–C10 alkyl substituted $NH_2$, C3–C10 branched or cycloalkyl substituted $NH_2$, C1–C10 dialkyl substituted $NH_2$, C1–C10 alkoxy, C1–C10 alkyl substituted thio, thiophenyl, halophenylthio, C1–C10 alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a C3–C10 ring.

In the foregoing chemical formula, the alkyl groups can be straight, branched, or cyclic, provided sufficient atoms are selected for the chemical formula. The C1–C30 substituted alkyl can include a wide variety of substituents, nonlimiting examples which include those selected from the group consisting of phenyl, pyridyl, furanyl, pyrrolidinyl, imidazonyl, $NH_2$, C1–C10 alkyl or dialkyl substituted $NH_2$, OH, SH, and C1–C10 alkoxy.

The foregoing chemical formula is also intended to encompass complex carbocyclic, aromatic and hetero atom structures for the A and/or X substituents, nonlimiting examples of which include naphthyl, quinolyl, isoquinolyl, adamantyl, and chlorophenylthio.

Pharmaceutically acceptable salts and derivatives of the bisphosphonates are also useful herein. Non-limiting examples of salts include those selected from the group consisting alkali metal, alkaline metal, ammonium, and mono-, di-, tri-, or tetra-C1–C30-alkyl-substituted ammonium. Preferred salts are those selected from the group consisting of sodium, potassium, calcium, magnesium, and ammonium salts. More preferred are sodium salts. Non-limiting examples of derivatives include those selected from the group consisting of esters, hydrates, and amides.

It should be noted that the terms "bisphosphonate" and "bisphosphonates", as used herein in referring to the therapeutic agents of the present invention are meant to also encompass diphosphonates, biphosphonic acids, and diphosphonic acids, as well as salts and derivatives of these materials. The use of a specific nomenclature in referring to the bisphosphonate or bisphosphonates is not meant to limit the scope of the present invention, unless specifically indicated. Because of the mixed nomenclature currently in use by those of ordinary skill in the art, reference to a specific weight or percentage of a bisphosphonate compound in the present invention is on an acid active weight basis, unless indicated otherwise herein. For example, the phrase "about 5 mg of a bone resorption inhibiting bisphosphonate selected from the group consisting of alendronate, pharmaceutically acceptable salts thereof, and mixtures thereof, on an alendronic acid active weight basis" means that the amount of the bisphosphonate compound selected is calculated based on 5 mg of alendronic acid.

Non-limiting examples of bisphosphonates useful herein include the following:

Alendronic acid, 4-amino-i-hydroxybutylidene-1,1-bisphosphonic acid.

Alendronate (also known as alendronate sodium or alendronate monosodium trihydrate), 4-amino-1-hydroxybutylidene-1,1-bisphosphonic acid monosodium trihydrate.

Alendronic acid and alendronate are described in U.S. Pat. Nos. 4,922,007, to Kieczykowski et al., issued May 1, 1990; 5,019,651, to Kieczykowski et al., issued May 28, 1991; 5,510,517, to Dauer et al., issued Apr. 23, 1996; 5,648,491, to Dauer et al., issued Jul. 15, 1997, all of which are incorporated by reference herein in their entirety.

Cycloheptylaminomethylene-1,1-bisphosphonic acid, YM 175, Yamanouchi (incadronate, formerly known as cimadronate), as described in U.S. Pat. No. 4,970,335, to Isomura et al., issued Nov. 13, 1990, which is incorporated by reference herein in its entirety.

1,1-dichloromethylene-1,1-diphosphonic acid (clodronic acid), and the disodium salt (clodronate, Procter and Gamble), are described in Belgium Patent 672,205 (1966) and *J. Org. Chem* 32, 4111 (1967), both of which are incorporated by reference herein in their entirety.

1-hydroxy-3-(1-pyrrolidinyl)-propylidene-1,1-bisphosphonic acid (EB-1053).

1-hydroxyethane-1,1-diphosphonic acid (etidronic acid).

1-hydroxy-3-(N-methyl-N-pentylamino)propylidene-1,1-bisphosphonic acid, also known as BM-210955, Boehringer-Mannheim (ibandronate), is described in U.S. Pat. No. 4,927,814, issued May 22, 1990, which is incorporated by reference herein in its entirety.

1-hydroxy-2-imidazo-(1,2-a)pyridin-3-yethylidene (minodronate).

6-amino-1-hydroxyhexylidene-1,1-bisphosphonic acid (neridronate).

3-(dimethylamino)-1-hydroxypropylidene-1,1-bisphosphonic acid (olpadronate).

3-amino-1-hydroxypropylidene-1,1-bisphosphonic acid (pamidronate).

[2-(2-pyridinyl)ethylidene]-1,1-bisphosphonic acid (piridronate) is described in U.S. Pat. No. 4,761,406, which is incorporated by reference in its entirety.

1-hydroxy-2-(3-pyridinyl)-ethylidene-1,1-bisphosphonic acid (risedronate).

(4-chlorophenyl)thiomethane-1,1-disphosphonic acid (tiludronate) as described in U.S. Pat. No. 4,876,248, to Breliere et al., Oct. 24, 1989, which is incorporated by reference herein in its entirety.

1-hydroxy-2-(1H-imidazol-1-yl)ethylidene-1,1-bisphosphonic acid (zoledronate).

Nonlimiting examples of bisphosphonates include alendronate, cimadronate, clodronate, etidronate, ibandronate, incadronate, minodronate, neridronate, olpadronate, pamidronate, piridronate, risedronate, tiludronate, and zolendronate, and pharmaceutically acceptable salts and esters thereof. A particularly preferred bisphosphonate is alendronate, especially a sodium, potassium, calcium, magnesium or ammonium salt of alendronic acid. Exemplifying the preferred bisphosphonate is a sodium salt of alendronic acid, especially a hydrated sodium salt of alendronic acid. The salt can be hydrated with a whole number of moles of water or non whole numbers of moles of water. Further exemplifying the preferred bisphosphonate is a hydrated sodium salt of alendronic acid, especially when the hydrated salt is alendronate monosodium trihydrate.

It is recognized that mixtures of two or more of the bisphosphonate actives can be utilized.

The precise dosage of the organic bisphosphonate will vary with the dosing schedule, the particular bisphosphonate chosen, the age, size, sex and condition of the mammal or human, the nature and severity of the disorder to be treated, and other relevant medical and physical factors. Thus, a precise pharmaceutically effective amount cannot be specified in advance and can be readily determined by the caregiver or clinician. Appropriate amounts can be determined by routine experimentation from animal models and human clinical studies. Generally, an appropriate amount of bisphosphonate is chosen to obtain a bone resorption inhibiting effect, i.e. a bone resorption inhibiting amount of the bisphosphonate is administered. For humans, an effective oral dose of bisphosphonate is typically from about 1.5 to about 6000 $\mu$g/kg body weight and preferably about 10 to about 2000 $\mu$g/kg of body weight. For alendronate monosodium trihydrate, common human doses which are administered are generally in the range of about 2 mg/day to about 40 mg/day, preferably about 5 mg/day to about 40 mg/day. In the U.S. presently approved dosages for alendronate monosodium trihydrate are 5 mg/day for preventing osteoporosis, 10 mg/day for treating osteoporosis, and 40 mg/day for treating Paget's disease.

In alternative dosing regimens, the bisphosphonate can be administered at intervals other than daily, for example once-weekly dosing, twice-weekly dosing, biweekly dosing, and twice-monthly dosing. In a once weekly dosing regimen, alendronate monosodium trihydrate would be administered at dosages of 35 mg/week or 70 mg/week. The bisphosphonates may also be administered monthly, ever six months, yearly or even less frequently, see WO 01/97788 (published Dec. 27, 2001) and WO 01/89494 (published Nov. 29, 2001).

"Estrogen" includes, but is not limited to naturally occurring estrogens [7-estradiol ($E_2$), estrone ($E_1$), and estriol ($E_3$)], synthetic conjugated estrogens, oral contraceptives and sulfated estrogens. See, Gruber C J, Tschugguel W, Schneeberger C, Huber J C., "Production and actions of estrogens" N Engl J Med Jan. 31, 2002;346(5):340–52.

"Estrogen receptor modulators" refers to compounds which interfere or inhibit the binding of estrogen to the receptor, regardless of mechanism. Examples of estrogen receptor modulators include, but are not limited to, estrogen, progestogen, estradiol, droloxifene, raloxifene, lasofoxifene, TSE-424, tamoxifen, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Cathepsin K inhibitors" refers to compounds which interfere with the activity of the cysteine protease cathepsin K. Nonlimiting examples of cathepsin K inhibitors can be found in PCT publications WO 00/55126 to Axys Pharmaceuticals and WO 01/49288 to Merck Frosst Canada & Co. and Axys Pharmaceuticals.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"An inhibitor of osteoclast proton ATPase" refers to an inhibitor of the proton ATPase, which is found on the apical membrane of the osteoclast, and has been reported to play a significant role in the bone resorption process. This proton pump represents an attractive target for the design of inhibitors of bone resorption which are potentially useful for the treatment and prevention of osteoporosis and related metabolic diseases. See C. Farina et al., "Selective inhibitors of the osteoclast vacuolar proton ATPase as novel bone anti-resorptive agents," DDT, 4: 163–172 (1999)), which is hereby incorporated by reference in its entirety.

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30–33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85–89 (Feb. 5, 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

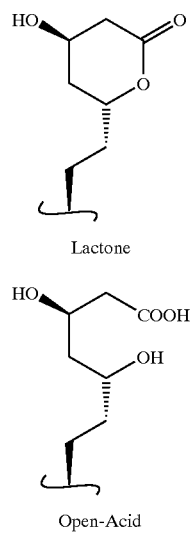

Lactone

Open-Acid

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenz-imidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

As used above, "integrin receptor antagonists" refers to compounds which selectively antagonize, inhibit or counteract binding of a physiological ligand to the $\alpha_v\beta_3$ integrin, to compounds which selectively antagonize, inhibit or counter-act binding of a physiological ligand to the αvβ5 integrin, to compounds which antagonize, inhibit or counteract binding of a physiological ligand to both the $α_vβ_3$ integrin and the $α_vβ_5$ integrin, and to compounds which antagonize, inhibit or counteract the activity of the particular integrin(s) expressed on capillary endothelial cells. The term also refers to antagonists of the $α_vβ_6$, $α_vβ_8$, $α_1β_1$, $α_2β_1$, $α_5β_1$, $α_6β_1$, $α_6β_4$ integrins. The term also refers to antagonists of any combination of $α_vβ_3$, $α_vβ_5$, $α_vβ_6$, $α_vβ_8$, $α_1β_1$, $α_2β_1$, $α_5β_1$, $α_6β_1$ and $α_6β_4$ integrins. H. N. Lode and coworkers in PNAS USA 96: 1591–1596 (1999) have observed synergistic effects between an antiangiogenic αv integrin antagonist and a tumor-specific antibody-cytokine (interleukin-2) fusion protein in the eradication of spontaneous tumor metastases. Their results suggested this combination as having potential for the treatment of cancer and metastatic tumor growth. $α_vβ_3$ integrin receptor antagonists inhibit bone resorption through a new mechanism distinct from that of all currently available drugs. Integrins are heterodimeric transmembrane adhesion receptors that mediate cell—cell and cell-matrix interactions. The α and β integrin subunits interact non-covalently and bind extracellular matrix ligands in a divalent cation-dependent manner. The most abundant integrin on osteoclasts is $α_vβ_3$ ($>10^7$/ osteoclast), which appears to play a rate-limiting role in cytoskeletal organization important for cell migration and polarization. The $α_vβ_3$ antagonizing effect is selected from inhibition of bone resorption, inhibition of restenosis, inhibition of macular degeneration, inhibition of arthritis, and inhibition of cancer and metastatic growth.

"An osteoblast anabolic agent" refers to agents that build bone, such as PTH. The intermittent administration of parathyroid hormone (PTH) or its amino-terminal fragments and analogues have been shown to prevent, arrest, partially reverse bone loss and stimulate bone formation in animals and humans. For a discussion refer to D. W. Dempster et al., "Anabolic actions of parathyroid hormone on bone," Endocr Rev 14: 690–709 (1993). Studies have demonstrated the clinical benefits of parathyroid hormone in stimulating bone formation and thereby increasing bone mass and strength. Results were reported by R M Neer et al., in New Eng J Med 344 1434–1441 (2001).

In addition, parathyroid hormone-related protein fragments or analogues, such as PTHrP-(1–36) have demonstrated potent anticalciuric effects [see M. A. Syed et al., "Parathyroid hormone-related protein-(1–36) stimulates renal tubular calcium reabsorption in normal human volunteers: implications for the pathogenesis of humoral hypercalcemia of malignancy," JCEM 86: 1525–1531 (2001)] and may also have potential as anabolic agents for treating osteoporosis.

Calcitonin is a 32 amino acid pepetide produced primarily by the thyroid which is known to participate in calcium and phosphorus metabolism. Calcitonin suppresses resorption of bone by inhibiting the activity of osteoclasts. Thus, calcitonin can allow osteoblasts to work more effectively and build bone.

"Vitamin D" includes, but is not limited to, vitamin $D_3$ (cholecalciferol) and vitamin $D_2$ (ergocalciferol), which are naturally occurring, biologically inactive precursors of the hydroxylated biologically active metabolites of vitamin D: 1α-hydroxy vitamin D; 25-hydroxy vitamin D, and 1α, 25-dihydroxy vitamin D. Vitamin $D_2$ and vitamin $D_3$ have the same biological efficacy in humans. When either vitamin $D_2$ or $D_3$ enters the circulation, it is hydroxylated by cytochrome $P_{450}$-vitamin D-25-hydroxylase to give 25-hydroxy vitamin D. The 25-hydroxy vitamin D metabolite is biologically inert and is further hydroxylated in the kidney by cytochrome P450-monooxygenase, 25 (OH) D-1α-hydroxylase to give 1,25-dihydroxy vitamin D. When serum calcium decreases, there is an increase in the production of parathyroid hormone (PTH), which regulates calcium homeostasis and increases plasma calcium levels by increasing the conversion of 25-hydroxy vitamin D to 1,25-dihydroxy vitamin D.

1,25-dihydroxy vitamin D is thought to be reponsible for the effects of vitamin D on calcium and bone metabolism. The 1,25-dihydroxy metabolite is the active hormone required to maintain calcium absorption and skeletal integrity. Calcium homeostasis is maintained by 1,25 dihydroxy vitamin D by inducing monocytic stem cells to differentiate into osteoclasts and by maintaining calcium in the normal range, which results in bone mineralization by the deposition of calcium hydroxyapatite onto the bone surface, see Holick, M F, Vitamin D photobiology, metabolism, and clinical applications, In: DeGroot L, Besser H, Burger H G, eg al., eds. *Endocrinology*, $3^{rd}$ ed., 990–1013 (1995). However, elevated levels of 1α,25-dihydroxy vitamin $D_3$ can result in an increase of calcium concentration in the blood and in the abnormal control of calcium concentration by bone metabolism, resulting in hypercalcemia. 1α,25-dihydroxy vitamin $D_3$ also indirectly regulates osteoclastic activity in bone metabolism and elevated levels may be expected to increase excessive bone resorption in osteoporosis.

"Synthetic vitamin D analogues" includes non-naturally occurring compounds that act like vitamin D.

Selective Serotonin Reuptake Inhibitors act by increasing the amount of serotonin in the brain. SSRIs have been used successfully for a decade in the United States to treat depression. Non-limiting examples of SSRIs include fluoxetine, paroxetine, sertraline, citalopram, and fluvoxamine. SSRIs are also being used to treat disoreders realted to estrogen functioning, suchs as premenstrual syndrome and premenstrual dysmorphic disorder. See Sundstrom-Poromaa I, Bixo M, Bjorn I, Nordh O., "Compliance to antidepressant drug therapy for treatment of premenstrual syndrome," J Psychosom Obstet Gynaecol December 2000; 21(4):205–11.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a bisphosphonate, etc.), "administration" and its variants are each understood to include concurrent and sequential introduction of the compound or prodrug thereof and other agents. The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

The present invention also encompasses a pharmaceutical composition useful in the treatment of osteoporosis or other bone disorders, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment. Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The compounds of the present invention can be used in combination with other agents useful for treating estrogen-mediated conditions. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating cathepsin-mediated conditions includes in principle any combination with any pharmaceutical composition useful for treating disorders related to estrogen functioning.

The scope of the invetion therefore encompasses the use of the instantly claimed compounds in combination with a second agent selected from: an organic bisphosphonate; a cathepsin K inhibitor; an estrogen; an estrogen receptor modulator; an androgen receptor modulator; an inhibitor of osteoclast proton ATPase; an inhibitor of HMG-CoA reductase; an integrin receptor antagonist; an osteoblast anabolic agent; calcitonin; Vitamin D; a synthetic Vitamin D analogue; a selective serotonin reuptake inhibitor; and the pharmaceutically acceptable salts and mixtures thereof.

These and other aspects of the invention will be apparent from the teachings contained herein.

Definitions

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The terms "treating" or "treatment" of a disease as used herein includes: preventing the disease, i.e. causing the clinical symptoms of the disease not to develop in a mammal that may be exposed to or predisposed tothe disease but does not yet experience or display symptoms of the disease; inhibiting the disease, i.e., arresting or reducing the development of the disease or its clinical symptoms; or relieving the disease, i.e., causing regression of the disease or its clinical symptoms.

The term "bone resorption," as used herein, refers to the process by which osteoclasts degrade bone.

The term "basic conditions," as used herein, refers to the incorporation or use of a base in the reaction medium. According to the Lowry-Bronsted definition, a base is a substance that accepts a proton; or according to the Lewis definition, a base is a substance that can furnish an electron pair to form a covalent bond. Examples of bases used herein, but are not limited to, are tertiary amine bases such as triethylamine, diisopropylethylamine, or the like.

The term "acidic conditions," as used herein, refers to the incorporation or use of an acid in the reaction medium. According to the Lowry-Bronsted definition, an acid is a substance that gives up a proton; or according to the Lewis definition, an acid is a substance that can take up an electron pair to form a covalent bond. Examples of acids used herein, but are not limited to, are strong carboxylic acids such as trifluoroacetic acid, or the like, strong sulfonic acids, such as trifluoromethane sulfonic acid, or the like, and Lewis acids, such as boron trifluoride etherate, or stannous chloride, or the like.

The term "reducing agent," as used herein, refers to a reagent capable of performing a reduction. A reduction is the conversion of a functional group or an intermediate from one category to a lower one. Examples of reducing agents used herein, but are not limited to, are triorganosilanes or stannanes, such as triethylsilane, triphenylsilane, and tri-n-butyl tin hydride, or the like. Other common reducing agents include, but are not limited to hydrogen, Raney Nickel, lithium aluminum hydride, diisobutylaluminum hydride, and the like.

The term "chemically differentiable" refers to two or more non-identical $R^6$ substituents whose unique structures are such that one of ordinary skill in the art could choose reaction conditions which would convert one of the non-identical $R^6$ substituents to H, without affecting the other $R^6$ substituent.

As used herein, "alkyl" is intended to include both branched and straight-chain saturated aliphatic hydrocarbon groups having the specified number of carbon atoms. For example, $C_1$–$C_{10}$, as in "$C_1$–$C_{10}$ alkyl" is defined to include groups having 1, 2, 3, 4, 5, 6, 7, 8, 9 or 10 carbons in a linear or branched arrangement. For example, "$C_1$–$C_{10}$ alkyl" specifically includes methyl, ethyl, propyl, butyl, pentyl, hexyl, heptyl, octyl, nonyl, decyl, and so on. "Alkoxy" represents an alkyl group of indicated number of carbon atoms attached through an oxygen bridge.

The term "cycloalkyl" or "carbocycle" shall mean cyclic rings of alkanes of three to eight total carbon atoms, or any number within this range (i.e., cyclopropyl, cyclobutyl, cyclopentyl, cyclohexyl, cycloheptyl or cyclooctyl).

If no number of carbon atoms is specified, the term "alkenyl" refers to a non-aromatic hydrocarbon radical, straight or branched, containing from 2 to 10 carbon atoms and at least 1 carbon to carbon double bond. Preferably 1 carbon to carbon double bond is present, and up to 4 non-aromatic carbon—carbon double bonds may be present. Thus, "$C_2$–$C_6$ alkenyl" means an alkenyl radical having from 2 to 6 carbon atoms. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated.

The term "cycloalkenyl" shall mean cyclic rings of 3 to 10 carbon atoms and at least 1 carbon to carbon double bond (i.e., cycloprenpyl, cyclobutenyl, cyclopenentyl, cyclohexenyl, cycloheptenyl or cycloocentyl).

The term "alkynyl" refers to a hydrocarbon radical straight or branched, containing from 2 to 10 carbon atoms and at least 1 carbon to carbon triple bond. Up to 3 carbon—carbon triple bonds may be present. Thus, "$C_2$–$C_6$ alkynyl" means an alkynyl radical having from 2 to 6 carbon atoms. Alkynyl groups include ethynyl, propynyl and butynyl. As described above with respect to alkyl, the straight or branched portion of the alkynyl group may contain triple bonds and may be substituted if a substituted alkynyl group is indicated.

In certain instances, substituents may be defined with a range of carbons that includes zero, such as ($C_0$–$C_6$) alkylaryl. If aryl is taken to be phenyl, this definition would include phenyl itself as well as —$CH_2Ph$, —$CH_2CH_2Ph$, $CH(CH_3)$ $CH_2CH(CH_3)Ph$, and so on.

As used herein, "aryl" is intended to mean any stable monocyclic or bicyclic carbon ring of up to 10 atoms in each ring, wherein at least one ring is aromatic. Examples of such aryl elements include phenyl, naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring.

The term "heteroaryl", as used herein, represents a stable monocyclic or bicyclic ring of up to 10 atoms in each ring, wherein at least one ring is aromatic and contains from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

As appreciated by those of skill in the art, "halo" or "halogen" as used herein is intended to include chloro, fluoro, bromo and iodo.

The term "hydroxyalkyl" means a linear monovalent hydrocarbon raidcal of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, and the like.

The term "heterocycle" or "heterocyclyl" as used herein is intended to mean a 5- to 10-membered nonaromatic ring containing from 1 to 4 heteroatoms selected from the group consisting of O, N and S, and includes bicyclic groups. "Heterocyclyl" therefore includes, but is not limited to the following: imidazolyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also emcompassed by this definition.

The present invention also includes N-oxide derivatives and protected derivatives of compounds of Formula I. For example, when compounds of Formula I contain an oxidizable nitrogen atom, the nitrogen atom can be converted to an N-oxide by methods well known in the art. Also when compounds of Formula I contain groups such as hydroxy, carboxy, thiol or any group containing a nitrogen atom(s), these groups can be protected with a suitable protecting groups. A comprehensive list of suitable protective groups can be found in T. W. Greene, Protective Groups in Organic Synthesis, John Wiley & Sons, Inc. 1981, the disclosure of which is incorporated herein by reference in its entirety. The protected derivatives of compounds of Formula I can be prepared by methods well known in the art.

The alkyl, alkenyl, alkynyl, cycloalkyl, aryl, heteroaryl and heterocyclyl substituents may be unsubstituted or unsubstituted, unless specifically defined otherwise. For example, a (C$_1$–C$_6$)alkyl may be substituted with one or more substituents selected from OH, oxo, halogen, alkoxy, dialkylamino, or heterocyclyl, such as morpholinyl, piperidinyl, and so on. In the case of a disubstituted alkyl, for instance, wherein the substituents are oxo and OH, the following are included in the definition: —(C=O)CH$_2$CH (OH)CH$_3$, —(C=O)OH, —CH$_2$(OH)CH$_2$CH(O), and so on.

Whenever the term "alkyl" or "aryl" or either of their prefix roots appear in a name of a substituent (e.g., aryl C$_{0-8}$ alkyl) it shall be interpreted as including those limitations given above for "alkyl" and "aryl." Designated numbers of carbon atoms (e.g., C$_{1-10}$) shall refer independently to the number of carbon atoms in an alkyl or cyclic alkyl moiety or to the alkyl portion of a larger substituent in which alkyl appears as its prefix root.

The term "triorganosilyl" means those silyl groups trisubstituted by lower alkyl groups or aryl groups or combinations thereof and wherein one substituent may be a lower alkoxy group. Examples of triorganosilyl groups include trimethylsilyl, triethylsilyl, t-butyldimethylsilyl, triisopropylsilyl, triphenylsilyl, dimethylphenylsilyl, t-butyldiphenylsilyl, phenyl-t-butylmethoxysilyl and the like.

In the compounds of the present invention, alkyl, alkenyl, alkynyl, cycloalkyl, cycloalkenyl, heterocyclyl and heteroaryl groups can be further substituted by replacing one or more hydrogen atoms be alternative non-hydrogen groups. These include, but are not limited to, halo, hydroxy, mercapto, amino, carboxy, cyano and carbamoyl.

The terms "arylalkyl" and "alkylaryl" include an alkyl portion where alkyl is as defined above and to include an aryl portion where aryl is as defined above. Examples of arylalkyl include, but are not limited to, benzyl, fluorobenzyl, chlorobenzyl, phenylethyl, phenylpropyl, fluorophenylethyl, chlorophenylethyl, thienylmethyl, thienylethyl, and thienylpropyl. Examples of alkylaryl include, but are not limited to, toluyl, ethylphenyl, and propylphenyl.

The term "heteroarylalkyl," as used herein, shall refer to a system that includes a heteroaryl portion, where heteroaryl is as defined above, and contains an alkyl portion. Examples of heteroarylalkyl include, but are limited to, pyridylmethyl, pyridylethyl and imidazoylmethyl.

The term "oxy" means an oxygen (O) atom. The term "thio" means a sulfur (S) atom. The term "oxo" means =O. The term "oximino" means the =N—O group. The term "keto" means carbonyl (C=O). The term "thiocynanto" refers to —SCN.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The compounds of the present invention may have asymmetric centers, chiral axes, and chiral planes (as described in: E. L. Eliel and S. H. Wilen, *Stereo-chemistry of Carbon Compounds*, John Wiley & Sons, New York, 1994, pages 1119–1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

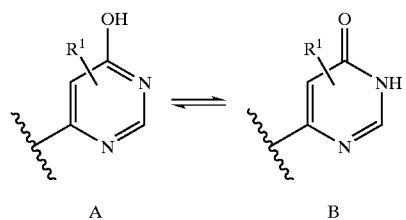

When any variable (e.g. R$^1$, R$^2$, R$^3$ etc.) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring carbon atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

Under standard nonmenclature used throughout this disclosure, the terminal portion of the designated side chain is described first, followed by the adjacent functionality toward the point of attachment. For example, a C$_{1-5}$ alkylcarbonylamino C$_{1-6}$ alkyl substituent is equivalent to

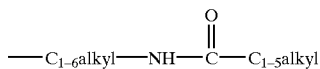

In choosing compounds of the present invention, one of ordinary skill in the art will recognize that the various substituents, i.e. R$^1$, R$^2$, R$^3$, R$^4$, R$^5$, R$^6$, R$^7$, V, X, Y, Z, n, m and p are to be chosen in conformity with well-known principles of chemical structure connectivity.

Representative compounds of the present invention typically display submicromolar affinity for alpha and/or beta estrogen receptors. Compounds of this invention are therefore useful in treating mammals suffering from disorders related to estrogen functioning.

The compounds of the present invention are available in racemic form or as individual enantiomers. For convenience, some structures are graphically represented as a single enantiomer but, unless otherwise indicated, is meant to include both racemic and enantiomerically pure forms. Where cis and trans sterochemistry is indicated for a compound of the present invention, it should be noted that the stereochemistry should be construed as relative, unless indicated otherwise. For example, a (+) or (−) designation should be construed to represent the indicated compound with the absolute stereochemistry as shown.

Racemic mixtures can be separated into their individual enantiomers by any of a number of conventional methods. These include, but are not limited to, chiral chromatography, derivatization with a chiral auxillary followed by separation by chromatography or crystallization, and fractional crystallization of diastereomeric salts. Deracemization procedures may also be employed, such as enantiomeric protonation of a pro-chiral intermediate anion, and the like.

The compounds of the present invention can be used in combination with other agents useful for treating estrogen-mediated conditions. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating estrogen-mediated conditions includes in principle any combination with any pharmaceutical composition useful for treating disorders related to estrogen functioning.

The pharmaceutically acceptable salts of the compounds of this invention include the conventional non-toxic salts of the compounds of this invention as formed inorganic or organic acids. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like. The preparation of the pharmaceutically acceptable salts described above and other typical pharmaceutically acceptable salts is more fully described by Berg et al., "Pharmaceutical Salts," *J. Pharm. Sci.*, 1977:66:1–19, hereby incorporated by reference. The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The novel compounds of the present invention can be prepared according to the following general schemes, using appropriate materials, and are further exemplified by the subsequent specific examples. The compounds illustrated in the examples are not, however, to be construed as forming the only genus that is considered as the invention. Those skilled in the art will readily understand that known variations of the conditions and processes of the following preparative procedures can be used to prepare these compounds. All temperatures are degrees Celsius unless otherwise noted.

The compounds of the present invention can be prepared according to the following generic Scheme I:

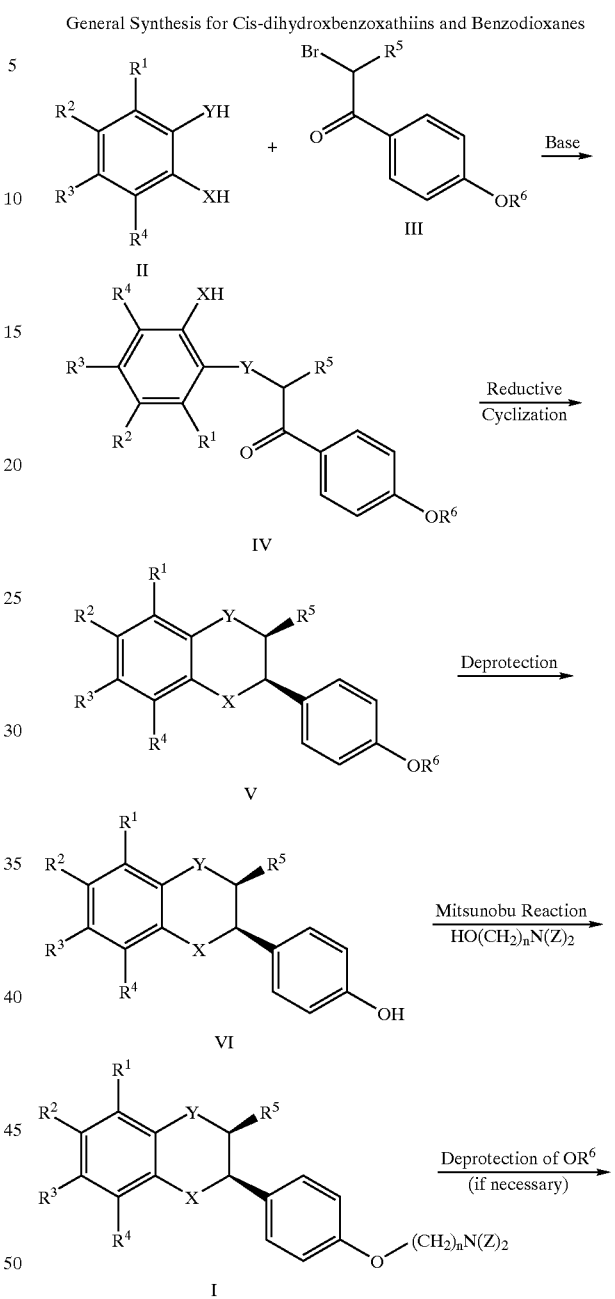

In words relative to the scheme, an appropriately functionalized bis-phenol II (X=O, Y=O), which is readily available, or a mercapto-phenol II (X=O, Y=S), which can be prepared according to literature procedures, can be reacted with a bromo-ketone derivative III, which is readily prepared from the corresponding ketone by bromination with phenyltrimethylammonium tribromide (PTAB), in the presence of a tertiary amine base, such as triethylamine, diisopropylethylamine, or the like, in a solvent such as dimethylformamide (DMF), formamide, acetonitrile, dimethylsulfoxide (DMSO), tetrahydrofuran (THF), dichloromethane, or the like, at a temperature of from −20° C. to 80° C. for as long as it takes for the reaction to complete to provide the displacement product IV. When X=Y=O, only $R^3$ maybe —$OR^6$. Alternatively, when X=Y=O and $R^2$ is —$OR^6$, the requisite cyclization intermediate can be obtained by interchanging the ketone and bromide functionalities.

Intermediate IV can be reductively cyclized in the presence of an organic acid such as trifluoroacetic acid, triflic acid, or the like, or a Lewis acid such as boron trifluoride etherate, stannous chloride, or the like, and a reducing agent such as a trisubstituted silane, such triethylsilane, or the like, in a solvent such as dichloromethane, chloroform, THF, toluene, or the like at a temperature of from −40° C. to 100° C. for as long as it takes for the reaction to complete to provide the cyclized product V, in which the stereochemistry of the aryl substituent and $R^5$ in the newly created ring is exclusively cis. The formation of the intermediates with analogous trans stereochemistry is depicted in the next general Scheme II.

In product V, when $R^6$ is a protecting group, it can be removed in a manner consistent with its nature. Such methods are well documented in the literature which are incorporated in standard textbooks, such as Greene, T. W. and Wuts, P. G. M., *Protective Groups in Organic Synthesis*, Third Ed.,Wiley, New York (1999). Further, it is understood that it is possible to have any number of the substitutents $R^1$–$R^4$ be or contain —$OR^6$, or $R^5$ may contain —$OR^6$, where $R^6$ is a protecting group, and it is further understood that in these instances the protecting groups are chemically differentiable, ie., they maybe selectively removed when necessary.

The alcohol intermediate VI can then be reacted with a reagent such as $HO(CH_2)_nNZ_2$ in a Mitsunobu reaction protocol, in which they are combined with a trisubstituted phosphine, such as triphenylphosphine and a diazodicarboxylate, such as diisopropylazodicarboxylate, in a suitable solvent such as THF at from 0° C. to 80° C. for as long as it takes for the reaction to complete to provide the coupled product I. The variables for the Mitsunobu reaction have been well documented and are incorporated herein by reference: Mitsunobu, O. *Synthesis*, 1981, 1; Castro, B. R. *Org. React.* 1983,29, 1; Hughes, D. L. *Org. React.* 1992,42, 335.

Finally, after the Mitsunobu reaction, it is understood that in I if any R group is or contains —$OR^6$, wherein $R^6$ is a protecting group, it may be removed utilizing the appropriate method found in Green and Wuts to give the final deprotected product.

SCHEME II

General Synthesis for Trans-dihydroxbenzoxathiins and Benzodioxanes

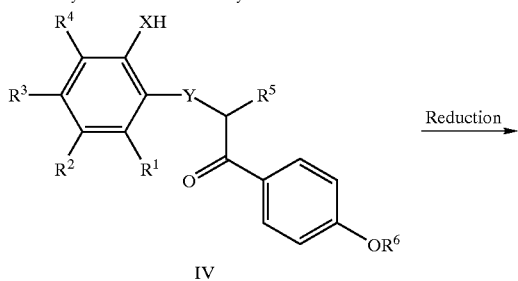

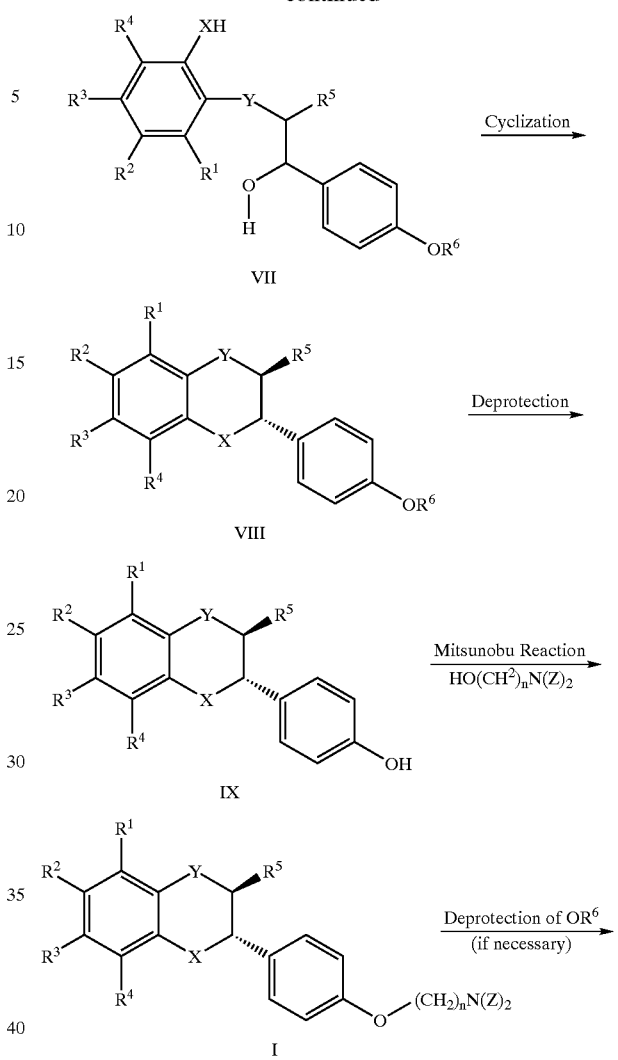

In words relative to the above scheme for the general preparation of the trans isomers of I, the ketone intermediate IV from Scheme I can be reduced with sodium borohydride, Super-Hydride® solution (lithium triethylborohydride in tetrahydrofuran), or the like, in a mixture of methanol and dichloromethane, or THF or the like at from 0° C. to ambient temperature to provide the analogous hydroxyl intermediate VII.

Cyclization of intermediate VII can be accomplished in the presence of an acid catalyst such as amberlyst 15, or triflic acid or the like, in a solvent such toluene, or dichloromethane or the like, at a temperature of from ambient to reflux to afford the trans compound VIII as the major isomer. The scheme outlined in Scheme I may then be used to afford trans I.

The compounds of the invention where X=O and Y=SO or $SO_2$ can be prepared as outlined in the general schemes that follow.

SCHEME III

Synthesis of Dihydrobenzoxathiin Dioxides

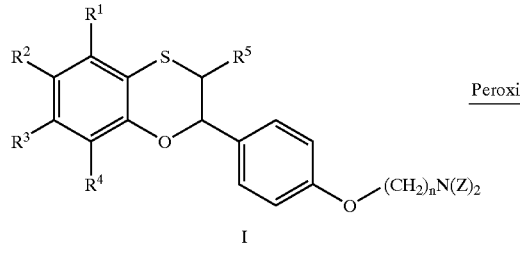

In words relative to Scheme III, the compounds I of the invention are peroxidized with an oxidant such as m-chloroperbenzoic acid, or per-trifluoroacetic acid, or the like, in a solvent such dichloromethane or the like, at a temperature of from 0° C. to reflux to produce the trioxide intermediate X. In turn X can be selectively deoxygenated at the nitrogen atom by treatment with a reducing agent such as sodium bisulfite or the like in a biphasic medium such as ethyl acetate and water, or the like, to provide I.

SCHEME IV

Synthesis of Dihydrobenzoxathiin Oxides

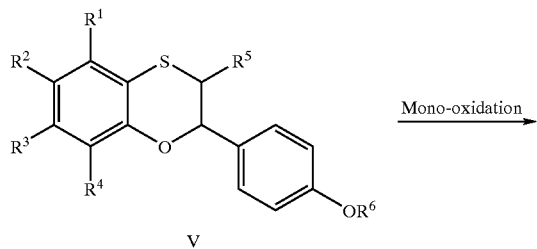

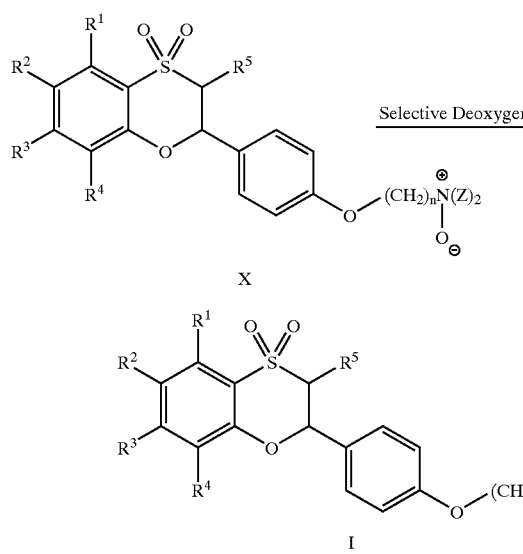

In words relevant to Scheme IV, the intermediate V of Scheme I can be mono-oxidized by careful treatment with one equivalent or a slight excess of an oxidant such as m-chloroperbenzoic acid, or dimethyldioxirane, or the like, in a solvent such as dichloromethane, ether, acetone, or the like, to give the corresponding sulfoxide intermediate XI. The scheme outlined in Scheme I may then be used to afford I.

SCHEME V

General Preparations of Thiophenols

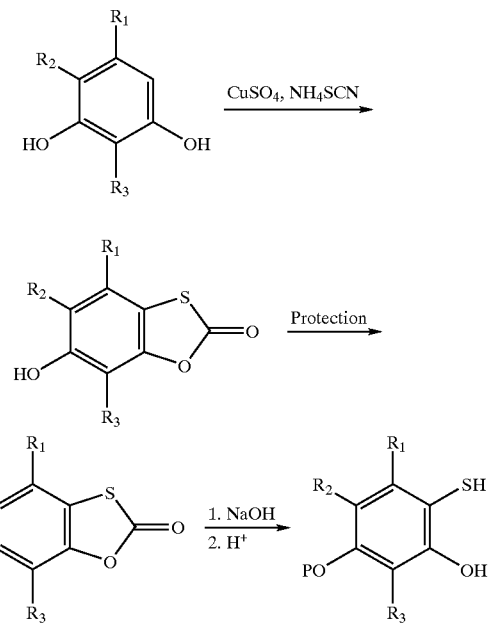

As depicted above, the various substituted 6-hydroxy-1, 3-benzoxathiol-2-ones were prepared by the known procedure decribed in Wermer, G.; Biebrich, W., U.S. Pat. Nos. 2,276,553 and 2,332,418, with minor modification:. After protection of the hydroxyl group, typically with a benzyl group, which is exemplified below, the analogous thiophenols were obtained by base hydrolysis and subsequent acidification as described in the prior reference.

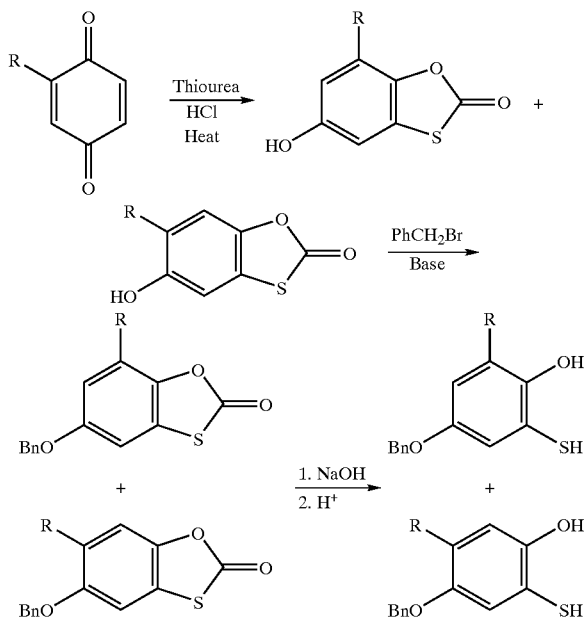

As depicted above, the various substituted 5-hydroxy-1,3-benzoxathiol-2-ones were prepared by the known procedures: Maxwell, S. J. Am. Chem. Soc. 1947, 69, 712; Lau, P. T. S., Kestner, M. J. Org. Chem. 1968, 33, 4426; Hanzlik, R. P. ibid, 1990, 55, 2736. After protection of the hydroxyl group, typically with a benzyl group, which is exemplified below, the analogous thiophenols were obtained by base hydrolysis and subsequent acidification as previously described.

General Protection Procedure

To a stirred solution of a mixture of the hydroxy-1,3-benzoxathiol-2-one and benzyl bromide (1.2 equivalents) in DMF at 0° C. was added a base, either sodium hydride or cesium carbonate (1.2 equivalents). The resulting mixture was stirred until a thin layer chromatogram indicated the reaction was complete.

The mixture was then partitioned between ethyl acetate, 2N HCl, and ice-water, and the organic phase was separated, washed thrice with water and then brine; dried over anhydrous sodium sulfate; filtered; and the filtrate evaporated.

The residue was purified by silica gel chromatography to give the corresponding benzyloxy-1,3-benzoxathiol-2-one.

ASSAYS

The utility of the compounds of the instant invention can be readily determined by methods well known to one of ordinary skill in the art. These methods may include, but are not limited to, the assays described in detail below. The compounds of the instant invention were tested in the following assays and found to have the relevant activity.

Estrogen Receptor Binding Assay

The estrogen receptor ligand binding assays are designed as scintillation proximity assays employing the use of tritiated estradiol and recombinant expressed estrogen receptors. The full length recombinant human ER-α and ER-β proteins are produced in a bacculoviral expression system. ERα or ERβ extracts are diluted 1:400 in phosphate buffered saline containing 6 mM α-monothiolglycerol. 200 µL aliquots of the diluted receptor preparation are added to each well of a 96-well Flashplate. Plates are covered with Saran Wrap and incubated at 4° C. overnight.

The following morning, a 20 ul aliquot of phosphate buffered saline containing 10% bovine serum albumin is added to each well of the 96 well plate and allowed to incubate at 4° C. for 2 hours. Then the plates are washed with 200 ul of buffer containing 20 mM Tris (pH 7.2), 1 mM EDTA, 10% Glycerol, 50 mM KCl, and 6 mM α-monothiolglycerol. To set up the assay in these receptor coated plates, add 178 ul of the same buffer to each well of the 96 well plate. Then add 20 ul of a 10 nM solution of $^3$H-estradiol to each well of the plate.

Test compounds are evaluated over a range of concentrations from 0.01 nM to 1000 nM. The test compound stock solutions should be made in 100% DMSO at 100×the final concentration desired for testing in the assay. The amount of DMSO in the test wells of the 96 well plate should not exceed 1%. The final addition to the assay plate is a 2 ul aliquot of the test compound which has been made up in 100% DMSO. Seal the plates and allow them to equilibrate at room temperature for 3 hours. Count the plates in a scintillation counter equipped for counting 96 well plates.

Ovariectomized Rat Assay

In the ovariectomized (OVX) Rat Assay, estrogen-deficiency is used to induce cancellous osteopenia (e.g. low bone mineral density [BMD; mg/cm$^2$]), associated with accelerated bone resorption and formation. Both the BMD and bone resorption/formation outcomes are used to model the changes in bone that occur as women pass through menopause. The OVX Rat Assay is the principal in vivo assay used by all major academic and industrial laboratories studying the efficacy of new chemical entities in preventing estrogen-deficiency bone loss.

Sprague-Dawley female rats aged 6–8 months are OVXd and, within 24 hours, started on treatment for 42 days with vehicle or multiple doses of test compound. Untreated sham-OVX and alendronate-treated (0.003 mg/kg s.c., q.d.) or 17β-estradiol-treated (0.004 mg/kg s.c., q.d.) groups are included as positive controls. Test compounds may be administered orally, subcutaneously, or by infusion through subcutaneously-implanted minipump. Before necropsy, in vivo dual labeling with calcein (8 mg/kg by subcutaneous injection), a bone seeking fluorochrome, is completed. At necropsy, blood, femurs, a vertebral body segment, and the uterus, are obtained.

The routine endpoints for the OVX Rat Assay include assessments of bone mass, bone resorption, and bone formation. For bone mass, the endpoint is BMD of the distal femoral metaphysis, a region that contains about 20% cancellous bone. The vertebral segment, a region with ~25% cancellous bone may also be used for BMD determination. The BMD measurement is made by dual energy x-ray absorptiometry (DXA, Hologic 4500A; Waltham, Mass.). For bone resorption, the endpoint is urinary deoxypyridinoline crosslinks, a bone collagen breakdown product (uDPD; expressed as nM DPD/nM creatinine). This measurement is made with a commercially available kit (Pyrilinks; Metra Biosystems, Mountain View, Calif.). For bone formation, the endpoints are mineralizing surface and mineral apposition rate, histomorphometric measures of osteoblast number and activity. This measurement is done on 5 µm sections of the non-decalcified proximal tibial metaphysis, using a semi-automated system (Bioquant; R&M Biometrics; Nashville, Tenn.). Similar endpoints and measuring techniques for each endpoint are commonly used in postmenopausal women.

Rat Cholesterol Lowering Assay Sprague-Dawley rats (5 per group) weighing about 250 g were subcutaneously dosed with compounds of the present invention dissolved in propylene glycol for 4 days. A group of 5 rats was dosed with vehicle only. On the fifth day, rats were euthanized with carbon dioxide and their blood samples were obtained. Plasma levels of cholesterol were assayed from these samples with commercially available cholesterol determination kits from Sigma.

MCF-7 Estrogen Dependent Proliferation Assay

MCF-7 cells (ATCC #HTB-22) are human mammary gland adenocarcinoma cells that require estrogen for growth. The growth media (GM) for the MCF-7 cells is Minimum Essential Media (without phenol red) supplemented with fetal bovine serum(FBS) to 10%. The FBS serves as the sole source of estrogen and this GM supports the full growth of the cells and is used for the routine growth of the cell cultures. When MCF-7 cells are placed in a media in which 10% Charcoal-Dextran treated fetal bovine serum (CD-FBS) is substituted for FBS, the cells will cease to divide but will remain viable. The CD-FBS does not contain detectable levels of estrogen and the media containing this sera is referred to as Estrogen Depleted Media (EDM). The addition of estradiol to EDM stimulates the growth of the MCF-7 cells in a dose dependent manner with an $EC_{50}$ of 2 pM.

Growing MCF-7 cells are washed several times with EDM and the cultures then maintained in EDM for a minimum of 6 days in order to deplete the cells of endogenous estrogen. On day 0 (at the startof the assay), these estrogen depleted cells are plated into 96-well cell culture plates at a density of 1000 cells/well in EDM in a volume of 180 ul/well. On day 1 test compounds are diluted in a 10-fold dilution series in EDM and 20 ul of these dilutions added to the 180 ul of media in the appropriate well of the cell plate resulting in a further 1:10 dilution of the test compounds. On days 4 and 7 of the assay, the culture supernatant is aspirated and replaced with fresh EDM and test compound dilutions as above. The assay is terminated at day 8–10 when the appropriate controls reach 80–90% confluency. At this point, the culture supernatants are aspirated, the cells washed 2×with PBS, the wash solution aspirated and the protein content of each well determined. Each drug dilution is evaluated on a minimum of 5 wells and the range of dilution of the test compounds in the assay is 0.00 nM to 1000 nM. The assay in the above format is employed to determine the estradiol agonist potential of a test compound.

In order to evaluate the antagonist activity of a test compound, the MCF-7 cells are maintained in EDM for a minimum of 6 days. Then on day 0 (at the start of the assay), these estrogen depleted cells are plated into 96-well cell culture plates at a density of 1000 cells/well in EDM in a volume of 180 ul/well. On day 1 the test compounds in fresh media containing 3 pM estradiol are applied to the cells. On days 4 and 7 of the assay, the culture supernatant is aspirated and replaced with fresh EDM containing 3 pM estradiol and the test compound. The assay is terminated at day 8–10 when the appropriate controls reach 80–90% confluency and the protein content of each well is determined as above.

Rat Endometriosis Model

Animals:
Species: Rattus norvegicus
Strain: Sprague-Dawley CD
Supplier: Charles River Laboratories, Raleigh, N.C.
Sex: Female Weight: 200–240 gram Rats are single-housed in polycarbonate cages and are provided Teklad Global Diet 2016 (Madison, Wis.) and bottled reverse osmosis purified H20 ad libitum. They are maintained on a12/12 light/dark cycle.

Rats are anesthetized with Telazol™ (20 mg/kg, ip) and oxymorphone (0.2 mg/kg sc) and positioned dorsoventrally on a sterile drape. Body temperature is maintained using a underlying circulating water blanket. The surgical sites are shaved with clippers and cleaned using three cycles of betadine/isopropyl alcohol or Duraprep® (3M). The incisional area is covered with a sterile drape.

Using aseptic technique, a 5 cm midline lower abdominal incision is made through the skin, subcutaneous and muscle layers. A bilateral ovariectomy is performed. The left uterine blood vessels are ligated and a 7 mm segment of the left uterine horn is excised. The uterus is closed with 4-0 gut suture. The myometrium is aseptically separated from the endometrium and trimmed to 5×5 mm. The trimmed section of the endometrium is transplanted to the ventral peritoneal wall with the epithelial lining of the segment opposed to the peritoneal wall. The explanted endometrial tissue is sutured at its four corners to the body wall using sterile 6-0 silk. The abdominal muscular layer is closed using sterile 4-0 chromic gut. The skin incision is closed using sterile stainless surgical clips. A sterile 90-day sustained release estrogen pellet (Innovative Research of America, 0.72 ng/pellet; circulating estrogen equivalent of 200–250 pg/mL) is implanted subcutaneously in the dorsal lateral scapular area. A sterile implantable programmable temperature transponder (IPTT) (BMDS, Seaford, Del.) is injected subcutaneously in the dorsoscapular region. The rats are observed until fully ambulatory, and allowed to recover from surgery undisturbed for 3 weeks.

Three weeks after transplantation of the endometrial tissue, the animals undergo a repeat laparotomy using aseptic surgical site preparation and technique. The explant is evaluated for graft acceptance, and the area is measured with calipers and recorded. The animals with rejected grafts are removed from the study. Animals are sorted to create similar average explant volume per group.

Drug or vehicle(control) treatment is initiated one day after the second laparotomy and continued for 14 days. Body temperature is recorded every other day at 10:00 am using the BMDS scanner.

At the end of the 14 day treatment period, the animals are euthanized by $CO_2$ overdose. Blood is collected by cardiocentesis for circulating estrogen levels. The abdomen is opened, the explant is examined, measured, excised, and wet weight is recorded. The right uterine horn is excised, and wet and dry weights are recorded.

EXAMPLES

Example 1

Preparation of Thiophenols

The following thiophenol derivatives were prepared according to the procedures outlined in Scheme V.

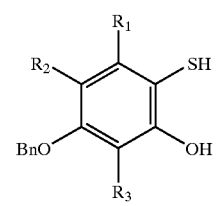

| COMPOUND NUMBER | THIOPHENOL | $^1$H NMR ppm (δ) |
|---|---|---|
| 1 | $R_1=R_2=R_3=H$ | 5.04 (s, 2H), 6.42 (bs, 1H), 6.54 (dd, 1H), 6.64 (d, 1H), 7.4 (m, 6H) |
| 2 | $R_1=R_3=H, R_2=CH_3$ | 2.2 (s, 3H), 4.78 (s, 1H), 5.5 (s, 2H), 6.65 (s, 1H), 7.3–7.5 (m, 5H) |
| 3 | $R_1=CH_3, R_2=R_3=H$ | — |
| 4 | $R_1=R_2=H, R_3=CH_3$ | — |
| 5 | $R_2=R_3=H, R_1=CH_3CH_2$ | — |
| 6 | $R_1=R_2=H, R_3=CH_3CH_2$ | 1.2 (t, 3H), 2.8 (q, 2H), 5.2 (s, 2H), 6.5 (d, 2H), 7.45 (m, 5H) |
| 7 | $R_1=R_3=H, R_2=Cl$ | 5.15 (s, 2H), 6.64 (s, 1H), 6.68 (s, 1H), 7.3–7.5 (m, 5H) |
| 8 | $R_2=R_3=H, R_1=Cl$ | 5.16 (s, 2H), 6.6 (dd, 1H), 6.82 dd, 1H), 7.34–7.44 (m, 5H) |
| 9 | $R_2=R_3=H, R_1=F$ | 5.05 (s, 2H), 6.4 (dd, 1H), 6.5 (d, 1H), 7.35–7.45 (m, 5H) |
| 10 | $R_2=R_3=H, R_1=OBn$ | 4.9 (s, 2H), 4.99 (s, 2H), 6.1 (d, 1H), 6.19 (d, 1H), 7.4 (m, 10H) |

Bn = benzyl

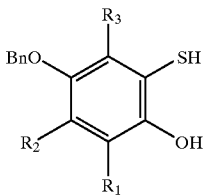

| COMPOUND NUMBER | THIOPHENOL | $^1$H NMR ppm (δ) |
|---|---|---|
| 11 | $R_1=R_2=R_3=H$ | 4.9 (s, 2H), 688 (d, 1H), 6.96 (d, 1H), 7.04 (dd, 1H), 7.3–7.4 (m, 5H) |
| 12 | $R_1=CH_3, R_2=R_3=H$ | 2.4 (s, 3H), 5.08 (s, 2H), 6.78 (dd, 1H), 6.85 (dd, 1H), 7.3–7.48 (m, 5H) |
| 13 | $R_1=R_3=H, R_2=Cl$ | 5.1 (s, 2H), 7.05 (s, 1H), 7.1 (s, 1H), 7.3–7.5 (m, 5H) |
| 14 | $R_1=R_2=H, R_3=Cl$ | 5.1 (s, 2H), 5.9 (d, 1H), 6.8 (d, 1H), 7.3–7.5 (m, 5H) |
| 15 | $R_2=R_3=H, R_1=Cl$ | 4.98 (s, 2H), 6.85 (d, 1H), 6.9 (d, 1H), 7.25–7.45 (m, 5H) |

Example 2

Preparation of 2-fluoro-3-mercapto-hydroquinone

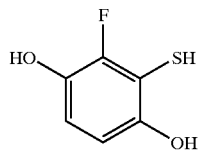

Step A:

A 3-neck 1-liter flask equipped with a low temperature thermometer, $N_2$ line, and dropping funnel was charged with 1,4-dimethoxy-2-fluorobenzene (20.42 g, 131 mmol). The solid was dissolved in distilled THF (450 mL) and cooled to an internal temperature of −74° C. A 2.5 M solution of n-BuLi in hexane (63 mL, 157 mmol) was subsequently added over 25 min. under $N_2$ via a dropping funnel. The reaction was maintained at −75° C. for 30 min., before adding solid sulfur (5.01 g, 157 mmol) in one portion. Nitrogen sparging of the reaction mixture was begun at this time and continued throughout the reaction. The internal temperature rose to −65° C. but quickly recooled to −75° C. The reaction temperature was maintained at −75° C. for 30 min. At this time, the excess dry ice in the dry ice/acetone bath was removed and the reaction was allowed to slowly warm to −20° C. over 1.5 h. The reaction was quenched with 2 N HCl with vigorous $N_2$ bubbling until the color of the reaction turned pale yellow. The internal temperature of the reaction rose to 10° C. The reaction was extracted with EtOAc. The organic layer was collected, washed with brine, dried over $MgSO_4$, filtered, and concentrated in vacuo. The yellow residue was purified by silica gel chromatography with 20% EtOAc/hexane as the eluant to give the desired product as a light yellow solid. $^1$H 600 MHz NMR(CDCl$_3$) ppm(δ): 3.84 (s, 3H), 3.86 (s, 3H), 6.56 (dd, J=1.8 Hz, J=8.9 Hz, 1H), 6.70 (t, 1H).

Step B:

To a solution of the thiophenol (10.66 g, 57 mmol) generated in Step A in $CH_2Cl_2$ (100 mL) at 0° C. under $N_2$ was added a 1 M solution of $BBr_3$ in $CH_2Cl_2$ (227 mL, 227 mmol) via a dropping funnel over 10 min. The reaction solution was continuously sparged with $N_2$. After stirring at 0° C. for 1 h, the reaction was quenched slowly with cold 2 N HCl. The resulting mixture was extracted with EtOAc. The organic layer was collected, washed with brine, dried over $Na_2SO_4$, filtered, and concentrated in vacuo. The resulting light purple solid was used without further purification. $^1$H 600 MHz NMR(CD$_3$OD) ppm(δ): 6.42 (dd, J=1.8 Hz, J=8.9 Hz, 1H), 6.51 (t, 1H).

Example 3

Preparation of 2-thiophene-4-methoxy-acetophenone

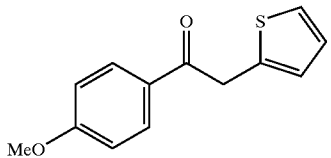

To a stirred solution of anisole (1.49 g, 13.8 mmol) in anhydrous dichloromethane (5 mL) was added AlCl$_3$ (1.2320 g, 9.2 mmol) followed by dropwise addition of 2-thiophene acetyl chloride (0.57 mL, 4.6 mmol) at 0° C. under $N_2$. The reaction was stirred for 1.5 h, then poured into a separatory funnel containing ice/brine/EtOAc. The organic layer was washed further with brine, dried over $Na_2SO_4$, and concentrated in vacuo. The resulting residue was purified by silica gel chromatography with 30% EtOAc/hexane as the eluant to afford the desired product as a yellow oil. $^1$H 500 MHz NMR(CDCl$_3$) ppm(δ): 3.89 (s, 3H), 4.46 (s, 2H), 6.98 (m, 4H), 7.24 (d, 1H), and 8.05 (d, 2H).

Example 4

Preparation of 2-thiophene-4-hydroxy-acetophenone

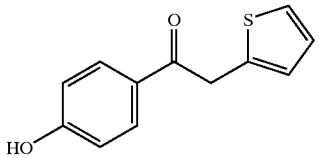

A mixture of 2-thophene-4-methoxy-benzophenone (0.8294 g, 3.5 mmol), generated in Example 3, and pyridine-HCl (4.0627 g, 35.2 mmol) was heated to 190° C. under $N_2$ for 6 h. The reaction was monitored by examining worked-up aliquots of the reaction by TLC (30% EtOAc/hexane). The reaction was cooled in an ice bath and ice/$H_2O$ was added. The resulting mixture was extracted with EtOAc. The organic extract was washed with 2 N HCl and brine, dried over $Na_2SO_4$, and concentrated in vacuo. The resulting brown residue was purified by silica gel chromatography with 30% EtOAc/hexane as the eluant to afford the desired product as a yellow/orange solid. $^1H$ 500 MHz NMR (CDCl$_3$)ppm($\delta$): 4.43 (s, 2H), 5.60 (bs, 1H), 6.90 (d, 2H), 6.92 (m, 1 H), 6.97 (m, 1H), 7.22 (d, 1 H) and 8.00 (d, 2H).

Example 5

Preparation of cycloalkyl-4-hydroxy-acetophenones

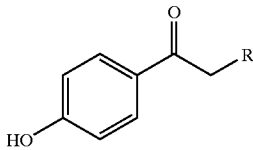

To a stirred solution of 2-cycloalkyl-1-(4-methoxyphenyl)-ethanone [prepared according to the method of Barrio, et al, *J. Med. Chem.,* 1971, 14, 898] in dry methylene chloride at 0° C. was added 3.6 equivalents of aluminum chloride and 3.0 equivalents of isopropyl mercaptan. The ice-water bath was removed and the reaction mixture was stirred further overnight under an inert atmosphere of nitrogen. The reaction mixture was poured onto a mixture of 2N HCl/ice and extracted with ethyl acetate. The ethyl acetate extract was washed with brine, dried over anhydrous sodium sulfate, filtered, and evaporated. Purification by silica gel chromatography afforded the corresponding 2-cycloalkyl-1-(4-hydroxy-phenyl)-ethanone.

Utilizing the foregoing experimental procedure the following compounds were prepared:

R=cyclohexyl: using methylene chloride-ethyl acetate (50:1) as the chromatography eluant. $^1H$ 500 MHz NMR(CDCl$_3$) ppm($\delta$):1–2.0 (m, 11H), 2.96 (d, 1H), 5.6 (bs, 1H) 6.92 (d, 2H), and 7.95 (d, 2H).

R=cyclopentyl: using methylene chloride-ethyl acetate (50:1) as the chromatography eluant. $^1H$ 500 MHz NMR(CDCl$_3$) ppm($\delta$):1.2–1.92 (m, 10H), 2.4 (m, 1H), 2.96 (d, 1H), 5.6 (bs, 1H), 6.91 (d, 2H), and 7.95 (d, 2H).

Example 6

Preparation of isopropyl-4-hydroxy-acetophenone

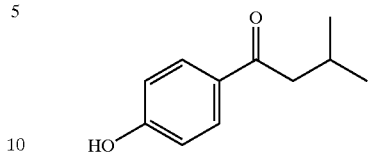

To a mixture of isovaleric acid (1.4 mL,13.0 mmol) and phenol (1.0253 g, 10.9 mmol) was added $BF_3OEt_2$ (15 mL) under nitrogen. The resulting mixture was heated to 80° C. for approximately 3.5 h. The reaction was poured into ice/2 N HCl and extracted with EtOAc. The organic extract was washed with brine, dried over $Na_2SO_4$, and concentrated in vacuo to give a yellow residue. The final product was isolated as a pale yellow oil after silica gel chromatography with 30% EtOAc/hexane as the eluant.

Upon standing at ambient temperature, the oil solidified to give a white solid. $^1H$ 500 MHz NMR(CDCl$_3$) ppm($\delta$): 1.01 (d, 6H), 2.27 (m, 1H), 2.81 (d, 2H), 6.99 (d, 2H) 7.93 (d, 2H).

Example 7

Preparation of 4-pyridyl-4-hydroxy-acetophenone

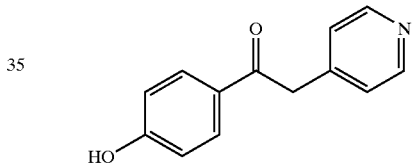

A dried flask equipped with a stirrer bar was charged with a 2.5 M solution of nBuLi in hexane (18 mL, 45.0 mmol) and cooled to 0° C. under $N_2$. A solution of diisopropylamine (6.4 mL, 45.7 mmol) in distilled THF (20 mL) was added slowly. After stirring for 25 min., a solution of 4-picoline (2.0 mL, 21.4 mmol) in distilled THF (8 mL) was added to the reaction. The resulting red solution was stirred for 25 min. before removing the ice bath. A solution of cyanophenol (2.5670 g, 21.4 mmol) in distilled THF (20 mL) was added via a dropping funnel over 30 min. After the further addition of THF, the reaction was allowed to stand at ambient temperature for 16 h, and was poured into a mixture of ice/sat. $NH_4Cl$/EtOAc. The intermediate enamine precipitated from the mixture as an insoluble yellow solid and was collected by vacuum filtration. The solid was redissolved in 2 N HCl. The EtOAc layer from the filtrate was also collected and extracted with 2 N HCl/ice. The acidic aqueous extract was combined with the enamine solution in 2 N HCl and stirred at ambient temperature for 16 h. The acidic solution was washed with EtOAc, cooled to 0° C., and neutralized to pH7 with sat. $NaHCO_3$. The desired product precipitated from the solution as a yellow solid and was collected, washed with cold water, and dried in vacuo. $^1H$ 500 MHz NMR(d-acetone) ppm($\delta$): 4.37 (s, 2H), 6.97 (d, 2H), 7.31 (d, 2H), 8.01 (d, 2H), 8.52 (bs, 2H).

Example 8

Preparation of 3-pyridyl-4-hydroxy-acetophenone

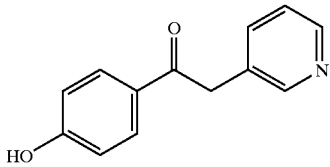

Following the procedure outlined in Example 7, with the exception that 1 equivalent of HMPA in THF was added to the reaction following addition of diisopropylamine, the 3-pyridyl-4-hydroxy-benzophenone was prepared from 3-picoline. The work-up differed slightly in that hydrolysis with 2 N HCl was unnecessary. Instead, the reaction was simply partitioned between ice/sat. $NH_4Cl$ and EtOAc. The organic layer was washed with brine, dried over $Na_2SO_4$, and concentrated in vacuo. The residue was triturated with $CH_2Cl_2$ and EtOAc to give the desired product as an orange solid. $^1H$ 500 MHz NMR($d_6$-acetone) ppm($\delta$): 4.39 (s, 2H), 6.97 (d, 2H), 7.31 (m, 1H), 7.68 (m, 1 H), 8.01 (d, 2H), 8.43 (m, 1H), 8.52 (m, 1H).

Example 9

Preparation of cycloalkyl-4-triisopropylsilyloxy-acetophenones

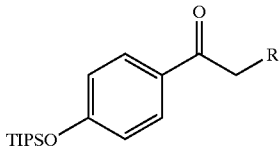

To a stirred solution of the 2-cycloalkyl-1-(4-hydroxy-phenyl)-ethanone, prepared in Example 5, in dry DMF at 0° C. was added 1.3 equivalents of diisopropylethylamine and 1.2 equivalents of triisopropylchlorosilane (TIPSCl). The ice-water bath was removed and the reaction mixture was stirred further until TLC showed the reaction to be complete (1–3 hours) under an inert atmosphere of nitrogen. The reaction mixture was partitioned between ether/2N HCl/ice and the organic phase was separated, washed twice with water, washed with brine, dried over anhydrous sodium sulfate, filtered, and evaporated. Purification by silica gel chromatography afforded the corresponding 2-cycloalkyl-1-(4-triisopropyloxy-phenyl)-ethanone.

Utilizing the foregoing experimental procedure the following compounds were prepared:

R=cyclohexyl: use methylene chloride-hexanes(1:1) as the chromatography eluant. $^1H$ 500 MHz NMR(CDCl$_3$) ppm($\delta$):1.13 (d, 18H), 1–1.99 (m, 14H), 2.78 (d, 1H), 6.9 (d, 2H), and 7.89 (d, 2H).

R=cyclopentyl: use methylene chloride-hexanes(1:1) as the chromatography eluant. $^1H$ 500 MHz NMR(CDCl$_3$) ppm($\delta$):1.12 (d, 18H), 1.2–1.91 (m, 13H), 2.4 (m, 1H) 2.95 (d, 1H), 6.92 (d, 2H), and 7.9 (d, 2H).

Example 10

Preparation of 2-heteroaryl-4-triisopropylsilyloxy-acetophenones

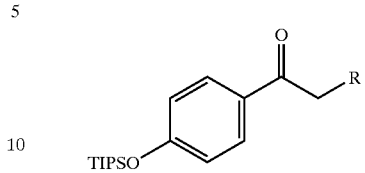

To a solution of the 2-heteroaryl-1-(4-hydroxy-phenyl)-ethanone, prepared in Examples 4, 7, and 8, in distilled THF, was added 1.3 equivalents of 60% NaH in mineral oil at 0° C. under $N_2$. After the gas evolution ceased, 1.1 equivalents of triisopropylchlorosilane (TIPSCl) was added dropwise and the resulting solution stirred for 30 min. The reaction was partitioned between ice/water and EtOAc. The organic layer was washed with brine, dried over $Na_2SO_4$, and concentrated in vacuo. Purification by silica gel chromatography afforded the corresponding 2-heteroaryl-1-(4-triisopropylsilyloxy-phenyl)-ethanones.

Utilizing the foregoing experimental procedure the following compounds were prepared:

R=2-thienyl: isolated as an orange/yellow solid using 15% EtOAc/hexane as the chromatography eluant. $^1H$ 500 MHz NMR(CDCl$_3$) ppm($\delta$):1.14 (d, 18H), 1.30 (m, 3H), 4.42 (s, 2H), and 6.93–7.98 (m, 7 H).

R=4-pyridyl: isolated as a yellow solid using 40% EtOAc/hexane as the chromatography eluant. $^1H$ 500 MHz NMR(CDCl$_3$) ppm($\delta$):1.14 (d, 18H), 1.30 (m, 3H), 4.28 (s, 2H), 6.97 (d, 2H), 7.35 (m, 1H), 7.69 (m, 1H), 7.97 (d, 2H), and 8.56 (bs, 2H).

R=3-pyridyl: isolated as a yellow solid using 40% EtOAc/hexane as the chromatography eluant. $^1H$ 500 MHz NMR(CDCl$_3$) ppm($\delta$):1.14 (d, 18H), 1.20 (m, 3H), 4.18 (s, 2H), 6.82 (d, 2H), 7.10 (d, 2H), 7.82 (d, 2H), and 8.43 (d, 2H).

Example 11

Bromination Procedure of Heteroaryl and Cycloalkyl-4-triisopropylsilyloxy-acetophenones

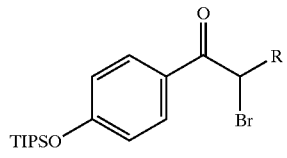

To a stirred solution of the 2-heteroaryl- and 2-cycloalkyl-1-(4-triisopropylsilyloxy-phenyl)-ethanones, prepared in Examples 9 and 10, in dry THF at 0° C. was added 1.0 equivalent of trimethylammoniumphenyl perbromide (PTAB). The ice-water bath was removed and the reaction mixture was stirred further for 1 hour under an inert atmosphere of nitrogen. The reaction mixture was partitioned between ethyl acetate/brine/ice/5%sodium thiosulfate/sodium bicarbonate and the organic phase was separated, washed with brine, dried over anhydrous sodium sulfate, filtered, and evaporated. Purification by silica gel chromatography afforded the corresponding 2-bromo-1-(4-triisopropylsilyloxy-phenyl)-ethanones.

Utilizing the foregoing experimental procedure the following compounds were prepared:

R=cyclohexyl: use methylene chloride-hexanes(1:1) as the chromatography eluant. $^1$H 500 MHz NMR(CDCl$_3$) ppm($\delta$): 1.14 (d, 18H), 0.98–2.27 (m, 15H), 4.91 (d, 1H), 6.94 (d, 2H), and 7.94 (d, 2H);

R=cyclopentyl: use methylene chloride-hexanes(1:1) as the chromatography eluant. $^1$H 500 MHz NMR(CDCl$_3$) ppm($\delta$):1.13 (d, 18H), 1.1–2.2 (m, 11H), 2.8 (m, 1H), 4.98 (d, 1H), 6.94 (d, 2H), and 7.96 (d, 2H);

R=2-thienyl: stirred at 0° C. for 40 min.; isolated as a dark brown oil and used in the next reaction without purification. $^1$H 500 MHz NMR(CDCl$_3$) ppm($\delta$):1.13 (d, 18H), 1.30 (m, 3H), 6.73 (s, 1H), 6.97 (d, 2H), 7.00 (m, 1H), 7.30 (m, 1H), 7.49 (d, 1H), and 8.00 (d, 2H);

R=4-pyridyl: added 2 equivalents of trimethylammoniumphenyl perbromide and stirred at 0° C. for 1 h; isolated as an orange/yellow oil and used in the next reaction without purification. $^1$H 500 MHz NMR (CDCl$_3$) ppm($\delta$):1.03 (d, 18H), 1.21 (m, 3H), 6.21 (s, 1H), 6.98 (d, 2H), 7.40 (d, 2H), 7.90 (d, 2H), and 8.57 (d, 2H);

R=3-pyridyl: added 2 equivalents of trimethylammoniumphenyl perbromide and stirred at 0° C. for 3 h; isolated as an orange/yellow oil and used in the next reaction without purification. $^1$H 500 MHz NMR (CDCl$_3$) ppm($\delta$):1.13 (d, 18H), 1.30 (m, 3H), 6.30 (s, 1H), 6.98 (d, 2H), and 7.39–8.75 (m, 6H).

Example 12

Preparation of 2-isopropyl-2-bromo-1-(4-hydroxyphenyl)-ethanone

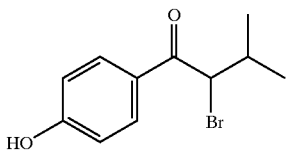

Following the procedure outlined in Example 11 and using the product obtained from Example 6,2-isopropyl-2-bromo-1-(4-hydroxyphenyl)-ethanone was isolated as a yellow oil and used in the next reaction without purification. $^1$H 500 MHz NMR(CDCl$_3$) ppm($\delta$): 1.01 (d, 3H), 1.21 (d, 3H), 2.46 (m, 1H), 4.93 (d, 1H), 6.96 (2H), and 7.96 (d, 2H).

Example 13

Preparation of 2-(3-methoxy-phenyl)-4-methoxy-acetophenone

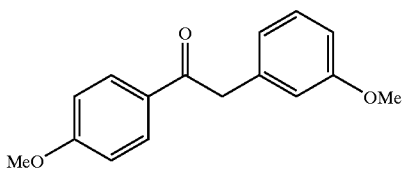

Following the procedure described in E. Napolitano, et al., *Gazz. Chim. Italia*, 1988, 118, 101, a mixture of anisole (70 g, 0.64 mol), 3-methoxyphenyl acetic acid (100 g, 0.6 mol), and 2 kg of PPA was mechanically stirred at 75° C. for 75 minutes under an atmosphere of nitrogen. The cooled, red reaction mixture was poured slowly into ice-water and then extracted with several portions of ethyl acetate. The combined extracts were washed with saturated sodium bicarbonate solution and brine, dried over anhydrous sodium sulfate, filtered, and the solvent removed in vacuo to give the crude product which was used without further purification. The material may be purified by column chromatography (Biotage) using hexanes-methylene chloride (2:1) as eluant. $^1$H 500 MHz NMR(CDCl$_3$) ppm($\delta$): 3.81 (s, 3H), 3.89 (s, 3H), 4.23 (s, 2H), 6.84 (dd, 1H), 6.88 (d, 1H), 6.89 (d, 1H), 6.95 (d, 2H), 7.26 (t, 1H), and 8.02 (d, 2H).

Example 14

Preparation of 2-(3-hydroxy-phenyl)-4-hydroxy-acetophenone

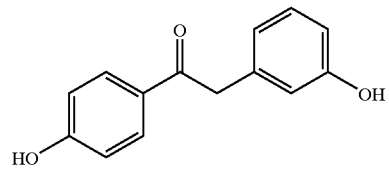

A mixture of 2-(3-methoxyphenyl)-4-methoxy-acetophenone (148.4 g, 0.6 mol), generated in Example 13, and pyridine-HCl (460 g, 3.98 mol) was heated to 184° C. under N$_2$ for 3.5 h. After this time, an additional 11 g of pyridine hydrochloride was added and the mixture and heated further for 1.8 h. Another 12.5 g of pyridine hydrochloride was added and after another 1.5 h, the reaction was cooled in an ice bath and ice/H$_2$O was added. The resulting mixture was extracted with EtOAc. The organic extract was washed with 2 N HCl and brine, dried over Na$_2$SO$_4$, and concentrated in vacuo. The resulting brown residue was purified by silica gel chromatography (Biotage) with 40% EtOAc/hexane as the eluant to afford the desired product as a yellow solid, and the of mono-methoxy product which could be recycled; $^1$H 500 MHz NMR(d$_6$-acetone) ppm($\delta$): 4.18 (s, 2H), 6.69 (dd, 1H), 6.78 (m, 2H), 6.91 (d, 2H), 7.1 (t, 1H), and 7.97 (d, 2H).

Example 15

Preparation of 4'-methoxymethyloxy-2-(4-Triisopropylsilyloxy-phenyl)acetophenone

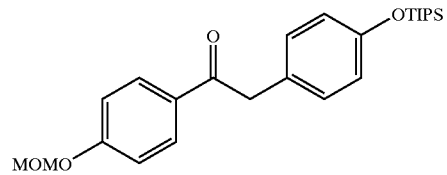

Step A

To a stirred solution of 3.0 g (13.2 mmol) of dry 4,4'-dihydroxy-desoxybenzoin (prepared as described by Poirier, D., etal, *J. Med. Chem.*, 1994, 37, 1115; and freshly azeotroped with toluene) in 25 mL of DMF at 0° C. was added 5.7 mL (5.7 mmol) of neat diisopropylethylamine. To this stirred solution was added slowly 1.25 mL (19.73 mmol) of chloromethylmethylether (MOMCl). The ice-water bath was removed and the mixture was stirred further under an atmosphere of nitrogen for 18 hours. The mixture was then poured into a saturated NaHCO$_3$ solution, extracted with EtOAc, and the extract washed with water, and dried over anhydrous MgSO$_4$. After evaporation of the solvent, the residue was purified by silica gel chromatography (EtOAc/Hexane=1:1) to provide the product, as a solid. 1H NMR (400 MHz, CDCl$_3$) δ (ppm): 8.0 (d, 2H), 7.19(d, 2H), 7.10 (d, 2H), 6.8 (d, 2H), 5.23 (s, 2H), 4.8 (s, 1H), 4.2 (s, 2H), 3.5 (s, 3H).

Step B

To a stirred solution of the product obtained from Step A (423 mg, 1.55 mmol) and imidazole (211 mg, 3.1 mmol) in 20 mL of dry DMF at 0° C. was added triisopropylsilyl chloride [TIPS-Cl] (3.1 mmol) and the reaction mixture was allowed to warm to room temperature and stirred further for 2–3 hours. The reaction was quenched by the addition of aqueous NaHCO$_3$ solution and extracted with EtOAc. The organic layer was washed with brine and dried with MgSO$_4$. Chromatography (10% EtOAc/hexane) yielded the desired product. $^1$H NMR (400 MHz, CDCl$_3$) δ (ppm): 8.0 (d, 2H), 7.12 (d, 2H), 7.08 (d, 2H). 6.82 (d, 2H), 5.21 (s, 2H), 4.18 (s, 2H), 3.5 (s, 3H), 1.24 (m, 3H), 1.1 (d, 18H).

Utilizing one or both of the foregoing experimental steps the following compounds were prepared:

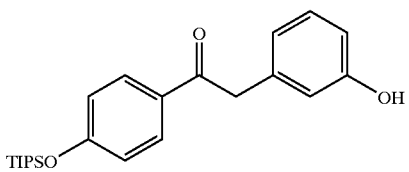

Using the ketone (8.7 g, 38 mmol) from Example 14 in anhydrous DMF (140 mL) at 0° C. under N$_2$ was added Hunig's base (8.0 mL, 46 mmol) followed by dropwise addition of TIPSCl (9.0 mL, 42 mmol). After stirring for 25 min. at 0° C., the reaction was partitioned between ice/2N HCl and EtOAc. The organic layer was collected, washed with brine, dried over Na$_2$SO$_4$, filtered, and concentrated in vacuo to give an oil. The residue was purified by silica gel chromatography with 20% EtOAc/hexane as the eluant to give the desired product as a yellow solid. $^1$H 500 MHz NMR(CDCl$_3$) ppm(δ): 1.13 (d, 18H), 1.30 (m, 3H), 4.20 (s, 2H), 6.77–6.82 (m, 3 H), 6.91 (d, 2H), 7.20 (t, 1 H), 7.99 (d, 2H).

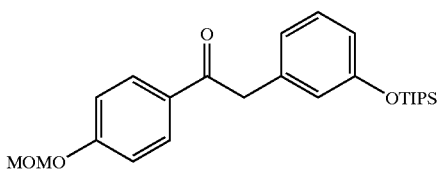

4'-methoxymethyloxy-2-(3-triisopropylsilyloxy-phenyl)-acetophenone: using the material from Example 14 and final chromatography (hexanes-ethyl acetate, 85:15) gave the product. $^1$H 500 MHz NMR(CDCl$_3$) ppm(δ): 1.07 (d, 18H), 1.2 (m, 3H), 3.5 (s, 3H), 4.19 (s, 2H), and 5.22 (s, 2H);

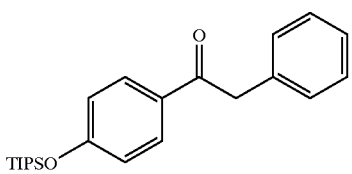

4-triisopropylsilyloxy-2-phenyl-acetophenone: using commercially available 4-hydroxy-2-phenyl-acetophenone and the Step B above. $^1$H 500 MHz NMR(CDCl$_3$) ppm(δ): 1.1 (d, 18H), 1.3 (m, 3H), 4.24 (s, 2H), 6.9 (d, 2H), 7.3 (m, 5H), 7.98 (d, 2H).

Example 16

Preparation of

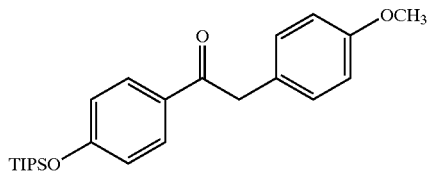

4'-triisopropylsilyloxy-2-(4-methoxy-phenyl) acetophenone was prepared according to the method of Gilman and Kirby, *J. Amer. Chem. Soc.*, 1932, 54, 345, using commercially available 4-methoxy-benzylmagnesium chloride and the triisopropylsilyl ether of 4-cyanophenol.

$^1$H 500 MHz NMR(CDCl$_3$) ppm(δ): 1.05 (d, 18H), 1.3 (m, 3H), 3.8 (s, 3H), 4.2 (s, 2H), 6.8 (d, 2H), 6.9 (d, 2H), 7.2 (d, 2H), 7.9 (d, 2H).

Example 17

Preparation of

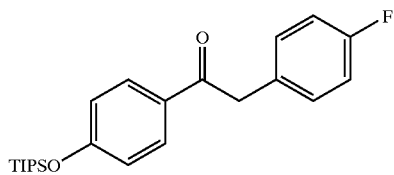

4'-triisopropylsilyloxy-2-(4-fluoro-phenyl)-acetophenone was prepared according to the method of Gilman and Kirby, *J. Amer. Chem. Soc.*, 1932, 54, 345, using commercially available 4-fluoro-benzylmagnesium chloride and the triisopropylsilyl ether of 4-cyanophenol.

$^1$H 500 MHz NMR(CDCl$_3$) ppm(δ): 1.1 (d, 18H), 1.3 (m, 3H), 4.2 (s, 2H), 6.9 (d, 2H), 7.0 (t, 2H), 7.2 (m, 2H), 7.98 (d, 2H).

Example 18

Preparation of

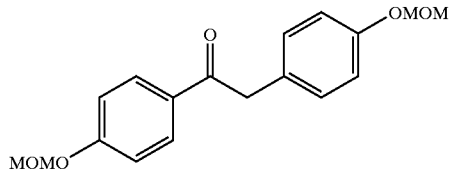

To a stirred solution of a mixture of the 0.1 g (0.37 mmol) mono-phenolic compound from Step A in Example 15 and diisopropylethylamine (0.13 mL, 2 eq) in 5 mL of DMF at room temperature was added slowly neat MOMCl (0.05 mL, 2 eq), and the mixture was heated at 85° C. under N$_2$ for three hours. The mixture was then poured into a saturated NaHCO$_3$ solution, extracted with EtOAc, washed with water, and dried over MgSO$_4$. After evaporation of the solvent, the residue was purified by silica gel chromatography (EtOAc/Hexane=1:1) to provide the pure bis-protected MOM product, as a solid. $^1$H NMR (400 MHz, CDCl$_3$) δ (ppm): 8.0 (d, 2H), 7.19(d, 2H), 7.10 (d, 2H), 7.02 (d, 2H), 5.23 (s, 2H), 5.2 (s, 2H), 4.2 (s, 2H), 3.5 (two s, 6H).

Example 19

Bromination Procedure of Phenyl-acetophenone Derivatives

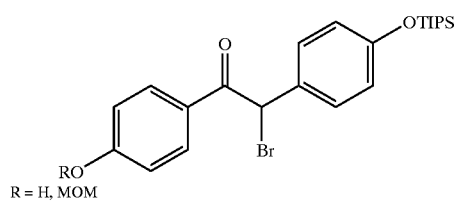

R = H, MOM

Preparation of 4'-Methoxymethyloxy- and 4'-Hydroxy-2-bromo-2-(4-triisopropylsilyoxy-phenyl)-acetophones To a stirred solution of 0.5 g (1.16 mmol) of the product from Step B of Example 15 in 100 mL of anhydrous THF was added 0.39 g (1.16 mmol) of trimethylphenylammonium perbromide (PTAB) at 0° C. The ice-water bath was removed, and the mixture was stirred further for one hour. The solution was then filtered and washed with water and brine and dried over MgSO$_4$. Removal of the solvent afforded the mixture of bromo-ketones (the MOM group was partially removed), which was used without further purification.

19a. Bromoketone with MOM group: $^1$H NMR (400 MHz, CDCl$_3$) δ (ppm): 8.0 (d, 2H), 7.4 (d, 2H), 6.88 (d, 2H), 6.86 (d, 2H), 6.36 (s, 1H), 1.24 (m, 3H), 1.1 (d, 18H)

19b. Bromoketone without MOM group: $^1$H NMR (400 MHz, CDCl$_3$) δ (ppm): 7.94 (d, 2H), 7.4 (d, 2H), 6.88 (d, 2H), 6.86 (d, 2H), 6.36 (s, 1H), 1.24 (m, 3H), 1.1 (d, 18H).

Alternatively, after the mixture was stirred for one hour, a few drops of 48% HBr was added to the mixture and it was stirred further until a thin layer chromatogram indicated that the removal of the methoxymethyl (MOM) group was complete, thus yielding only 4'-hydroxy-2-bromo-2-(4-triisopropylsilyloxy-phenyl)-acetophenone.

19c. Preparation of 4'-Hydroxy-2-bromo-2-(3-triisopropylsilyoxy-phenyl)-acetophones To a stirred solution of 40.7 g (0.095 mol) of 4'-methoxymethyloxy-2-(3-triisopropylsilyloxy-phenyl)-acetophenone, from Example 15, in 400 mL of dichloromethane at 0° C. was added all at once 37.5 g (0.099 mol) of solid trimethylammoniumphenyl perbromide. The ice-water bath was removed and the reaction mixture was stirred further for 4 h under an inert atmosphere of nitrogen. The reaction mixture was partitioned between ethyl acetate, ice, brine, 5% aqueous sodium thiosulfate, and saturated sodium bicarbonate. The organic phase was separated washed with brine; dried over anhydrous sodium sulfate, filtered, evaporated, and dried in vacuo to give 46 g of crude product which was used without further purification. $^1$H 500 MHz NMR(CDCl$_3$) ppm(δ): 1.07 (d, 18H), 1.2 (m, 3H), and 6.3 (s, 1H);

Utilizing the foregoing experimental procedures the following compounds were prepared:

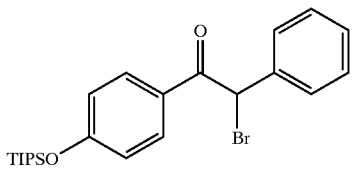

19d. Using 4-triisopropylsilyloxy-2-phenyl-acetophenone, prepared in Example 15, 4-triisopropylsilyoxy-2-bromo-2-phenyl-acetophenone was realized; $^1$H NMR (400 MHz, CDCl$_3$) δ (ppm) 7.94 (d, 2H), 7.56 (m, 2H), 7.38 (m, 3H), 6.9 (d, 2H), 6.36 (s, 2H), 1.28 (m, 3H), 1.1 (d, 18H);

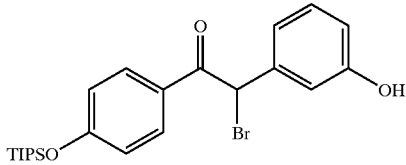

19e. Using 4-triisopropylsilyloxy-2-(3-hydroxyphenyl)-acetophenone (8.93 g, 23 mmol) from Example 15, crude 4-triisopropylsilyloxy-2-bromo-2-(3-hydroxyphenyl)-acetophenone was realized which was used without further purification. $^1$H 500 MHz NMR(CDCl$_3$) ppm(δ): 1.10 (d, 18H), 1.25 (m, 3H), 6.29 (s, 1H), 6.80–7.22 (m, 6 H), 7.90 (d, 2H);

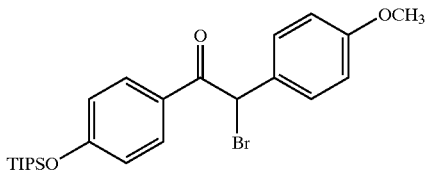

19f. Using 4-triisopropylsilyloxy-2-(4-methoxy-phenyl)-acetophenone, prepared in Example 16, 4-triisopropylsilyloxy-2-bromo-2-(4-methoxy-phenyl)-acetophenone was realized; $^1$H NMR (400 MHz, CDCl$_3$) δ (ppm) 7.9 (d, 2H), 7.5 (d, 2H), 6.9 (d & d, 4H), 6.4 (s, 1H), 3.8 (s, 3H), 1.28 (m, 3H), 1.1 (d, 18H);

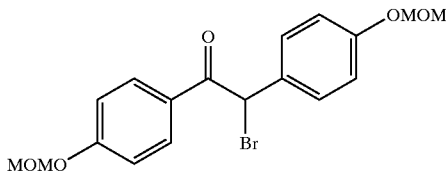

19g. Using the bis-MOM-phenyl-acetophenone, prepared in Example 18, the corresponding bromo-phenyl-acetophenone was realized. $^1$H NMR (400 MHz, CDCl$_3$) δ (ppm): 8.0 (d, 2H), 7.45(d, 2H), 7.10 (two d, 4H), 6.4 (s, 1H), 5.23 (two s, 4H), 3.5 (two s, 6H);

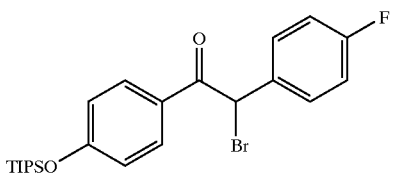

19h. Using 4'-triisopropylsilyloxy-2-(4-fluoro-phenyl)-acetophenone, prepared in Example 17, 4-triisopropylsilyloxy-2-bromo-2-(4-fluoro-phenyl)-acetophenone was realized. $^1$H NMR (400 MHz, CDCl$_3$) δ (ppm) 7.98 (d, 2H), 7.6 (m, 2H), 7.08 (t, 2H), 6.9 (d, 2H), 6.38 (s, 1H), 1.3 (m, 3H), 1.1 (d, 18H).

Example 20

Preparation of Thioketones

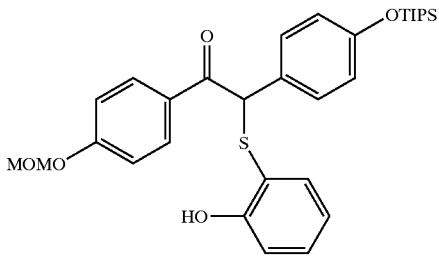

20a. Preparation of 4'-Methoxymethyloxy-2-(2-hydroxythiophenyl)-2-(3-triisopropylsilyoxy-phenyl)-acetophone To a stirred, freshly prepared solution of 2-thiophenol (0.2 g, 1.6 mmol) and Et$_3$N (0.34 mL, 2 eq) in 15 mL DMF at 0° C. was slowly added a solution of 0.627 g (1.232 mmol) of bromoketone 19a described in Example 19 in 13 mL of DMF. The reaction mixture was stirred for three hours at room temperature and was then partitioned between saturated NaHCO$_3$ and EtOAc, the layers were separated, and the aqueous layer was extracted again with EtOAc. The combined organic layers were dried (Na$_2$SO$_4$), filtered, and evaporated in vacuo. The resulting oil was purified by flash chromatography (EtOAc/Hex=1:4) to provide the desired product as an oil. $^1$H NMR (400 MHz, acetone-d$_6$) δ (ppm): 8.0 (d, 2H), 7.2–6.6 (m, 8H), 6.8 (d, 2H), 6.2 (s, 1H), 5.24 (s, 2H), 3.4 (s, 3H), 1.22 (m, 3H), 1.1 (d, 18H); MS m/z 575 (M$^+$+23).

Utilizing the foregoing experimental procedure the following compounds were prepared:

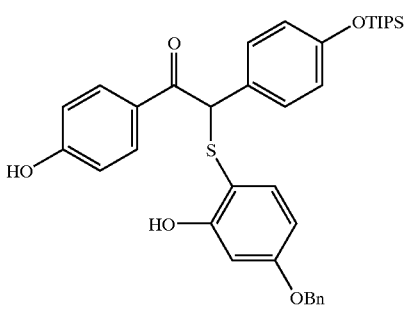

A

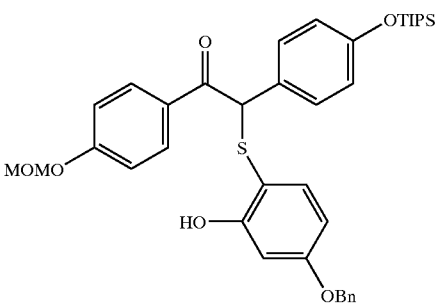

B

20b. Using 0.83 g (3.6 mmol) of 4-benzyloxy-thiophenol (compound 1 from Example 1) and the requisite amount of the mixture of bromides 19a,b from Example 19, product A and product B were obtained after silica gel chromatography using EtOAc/hexane (1:5) as the eluant;

A: $^1$H NMR (400 MHz, acetone-d$_6$) δ (ppm): 8.15 (s, 1H), 7.8 (d, 2H), 7.4 (m, 5H), 6.98 (d, 2H), 6.98 (d, 1H), 6.75 (d & d, 4H), 6.0 (s, 1H), 5.62 (s, 1H), 5.0 (s, 2H), 1.22 (m, 3H), 1.15 (d, 18H);

B: $^1$H NMR (400 MHz, acetone-d$_6$) δ (ppm): 8.0 (d, 2H), 7.5 (m, 5H), 7.18 (d, 2H), 7.04 (d, 2H), 6.96 (d, 1H), 6.8 (d, 2H), 6.56 (d, 1H), 6.32 (dd, 1H), 6.1 (s, 1H), 5.25 (s, 2H), 5.09 (s, 1H), 3.4 (s, 3H), 1.22 (m, 3H), 1.1 (d, 18H);

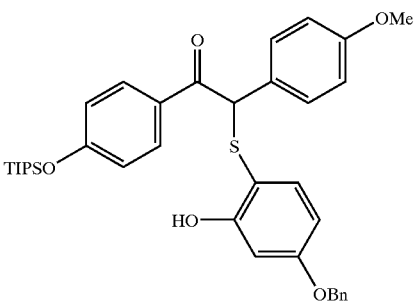

20c. Using 1.1 g (2.3 mmol) of the bromoketone 19f from Example 19 and the appropriate amount of compound 1 from Example 1, the corresponding thioketone was obtained after silica gel chromatography using EtOAc/hexane (1:5) as the eluant; $^1$H NMR (400 MHz, acetone-d$_6$) δ (ppm): 8.46 (br s, 1H), 7.98 (d, 2H), 7.48–7.3 (m, 5H), 7.24 (d, 2H), 7.4 (d, 1H), 6.92 (d, 2H), 6.82 (d, 2H), 6.56 (d, 1H), 6.38 (dd, 1H), 6.1 (s, 1H), 5.04 (s, 2H), 3.72 (s, 3H), 1.25 (m, 3H), 1.1 (d, 18H).

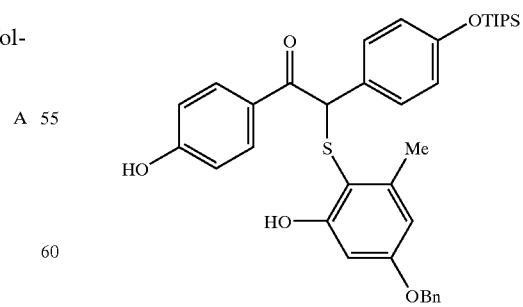

20d. Using 0.74 g (1.5 mmol) of the bromoketone 19b from Example 19 and the appropriate amount of compound 3 from Example 1, the desired product was obtained after silica gel chromatography using EtOAc/hexane (1:5) as the eluant. ¹H NMR (400 MHz, acetone-d₆) δ (ppm): 7.92 (d, 2H), 7.46–7.1 (m, 5H), 7.18 (d, 2H), 6.84 (d, 2H), 6.78 (d, 2H), 6.42 (d, 1H), 6.36 (d, 1H), 5.98 (s, 1H), 5.02 (s, 2H), 1.22 (m, 3H), 1.1 (d, 18H).

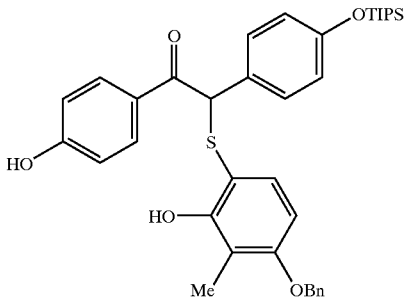

20e. Using 0.8 g (1.57 mmol) of the bromoketone 19b from Example 19 and the appropriate amount of compound 4 from Example 1, the desired product was obtained after silica gel chromatography using EtOAc/hexane (1:5) as the eluant. ¹H NMR (400 MHz, acetone-d₆) δ (ppm): 7.9 (d, 2H), 7.5–7.3 (m, 5H), 7.12 (d, 2H), 6.9 (d,1H), 6.84 (d, 2H), 6.79 (d, 2H), 6.4 (d, 1H), 6.0 (s, 1H), 5.1 (s, 2H), 2.1 (s, 3H), 1.25 (m, 3H), 1.1 (d, 18H).

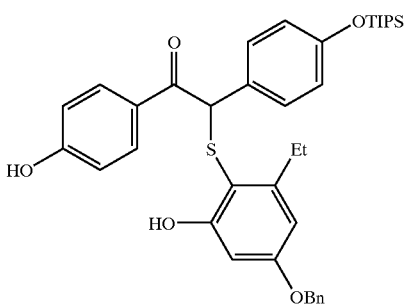

20f. Using 0.56 g (1.1 mmol) of the bromoketone 19b from Example 19 and 0.19 g (0.73 mmol) of compound 5 from Example 1, the desired product was obtained after silica gel chromatography using EtOAc/hexane (1:5) as the eluant. ¹H NMR (400 MHz, acetone-d₆) δ (ppm): 7.9 (d, 2H), 7.48–7.3 (m, 5H), 7.16 (d, 2H), 6.84 (d, 2H), 6.78 (d, 2H), 6.42 (d, 1H), 6.38 (d, 1H), 5.96 (s, 1H), 5.1 (s, 2H), 2.6 (q, 2H), 1.22 (m,

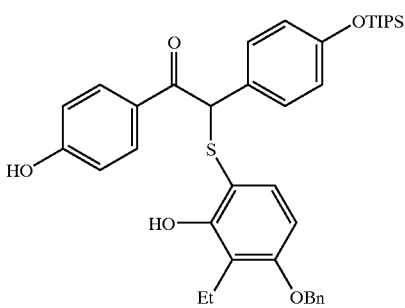

20g. Using 2.04 g (4.33 mmol) of the bromoketone 19b from Example 19 and the appropriate amount of compound 6 from Example 1, the desired product was obtained after silica gel chromatography using EtOAc/hexane (1:5) as the eluant. ¹H NMR (400 MHz, acetone-d₆) δ (ppm): 7.9 (d, 2H), 7.5–7.3 (m, 5H), 7.12 (d, 2H), 6.92 (d, 1H), 6.84 (d, 2H), 6.78 (d, 2H), 6.42 (d, 1H), 6.0 (s, 1H), 5.1 (s, 2H), 2.7 (q, 2H), 1.24 (m, 3H), 1.1 (d & t, 21H).

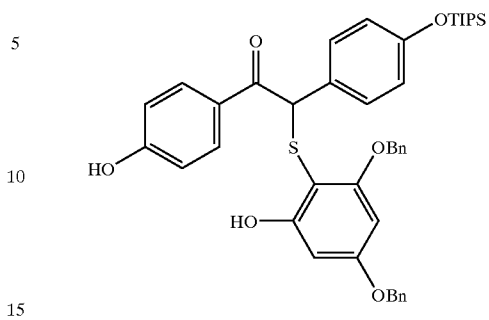

20h. Using 2.0 g (4.33 mmol) of the bromoketone 19b from Example 19 and the appropriate amount of compound 10 from Example 1, the desired product was obtained after silica gel chromatography using EtOAc/hexane (1:5) as the eluant. ¹H NMR (400 MHz, acetone-d₆) δ (ppm): 7.8 (d, 2H), 7.62 (d, 2H), 7.48–7.3 (m, 8H), 7.12 (d, 2H), 6.8 (d, 2H), 6.76 (2H, d), 6.28 (d, 1H), 6.18 (d, 1H), 6.0 (s, 1H), 5.24 (s, 2H), 5.05 (s, 2H), 1.22 (m, 3H), 1.1 (d, 18H).

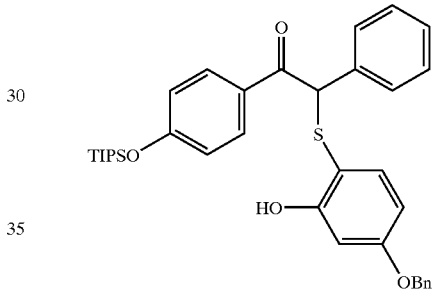

20i. Using 1.6 g (3.51 mmol) of the bromoketone 19d from Example 19 and the appropriate amount of compound 1 from Example 1, the desired product was obtained after silica gel chromatography using EtOAc/hexane (1:5) as the eluant. ¹H NMR (400 MHz, acetone-d₆) δ (ppm): 8.0 (d, 2H), 7.5–7.2 (m, 10H), 7.0 (d, 1H), 6.92 (d, 2H), 6.54 (d, 1H), 6.35 (dd, 1H), 6.12 (s, 1H), 5.06 (s, 2H), 1.22 (m, 3H), 1.1 (d, 18H).

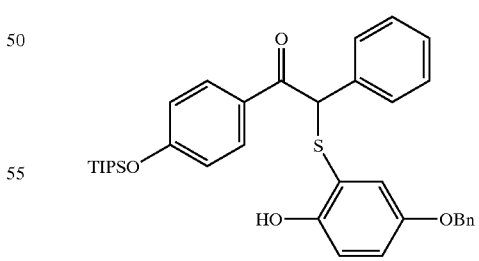

20j. Using 2.6 g (5.82 mmol) of the bromoketone 19d from Example 19 and the appropriate amount of compound 11 from Example 1, the desired product was obtained after silica gel chromatography using EtOAc/hexane (1:5) as the eluant. ¹H NMR (400 MHz, acetone-d₆) δ (ppm): 8.0 (d, 2H), 7.4–7.2 (m, 10H), 6.94 (d, 2H), 6.84–6.74 (m, 3H), 6.24 (s, 1H), 4.85 (s, 2H), 1.23 (m, 3H), 1.1 (d, 18H).

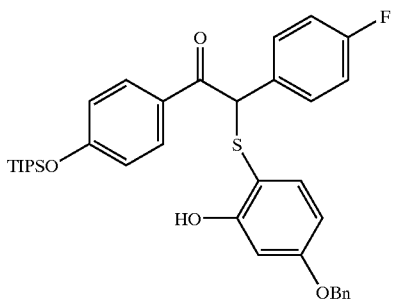

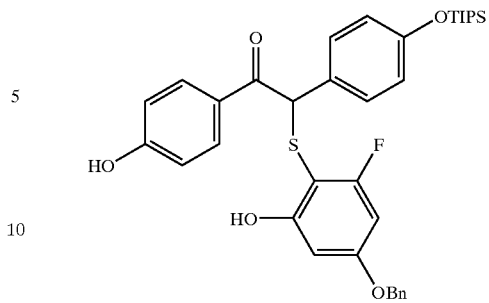

20k. Using the bromoketone 19h from Example 19 and the appropriate amount of compound 1 from Example 1, the desired product was obtained after silica gel chromatography using EtOAc/hexane (1:5) as the eluant. $^1$H NMR (400 MHz, acetone-$d_6$) δ (ppm): 8.0 (d, 2H), 7.4–7.2 (m, 7H), 7.0 (m, 5H), 6.54 (d, 1H), 6.28 (dd, 1H), 6.14 (s, 1H), 5.08 (s, 2H), 1.23 (m, 3H), 1.1 (d, 18H).

20n. Using the bromoketone 19b from Example 19 and compound 9 from Example 1, the desired product was obtained after silica gel chromatography using EtOAc/hexane (1:5) as the eluant. $^1$H NMR (500 MHz, CDCl$_3$) δ (ppm): 8.20 (s, 1H), 7.81 (d, 2H), 7.40 (m, 5H), 7.02 (d, 2H), 6.75 (d, 4H), 6.36 (d, 1H), 6.20 (dd, 1H), 5.78 (s, 1H), 4.95 (s, 2H), 1.23 (m, 3H), 1.10 (m, 18H).

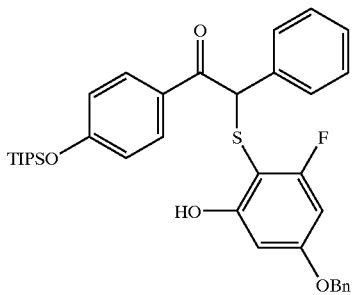

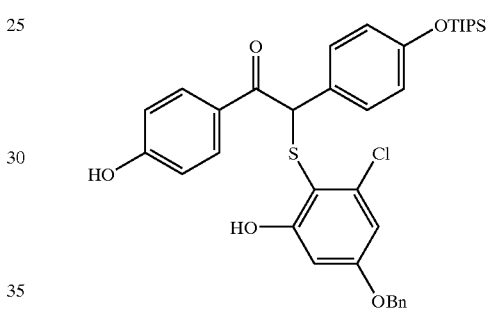

20l. Using the bromoketone 19d from Example 19 with the appropriate amount of compound 9 from Example 1, the desired product was obtained after silica gel chromatography using EtOAc/hexane (1:5) as the eluant. $^1$H NMR (500 MHz, CDCl$_3$) δ (ppm) 8.28 (s, 1H), 7.82 (d, 2H), 7.40 (m, 5H), 7.22 (m, 5H), 6.80 (d, 2H), 6.40 (d, 1H), 6.21 (dd, 1H), 5.80 (s, 1H), 5.00 (s, 2H), 1.24 (m, 3H), 1.10 (d, 18H).

20o. Using the bromoketone 19b from Example 19 and compound 8 from Example 1, the desired product was obtained after silica gel chromatography using EtOAc/hexane (1/5) as the eluant. $^1$H NMR (500 MHz, CDCl$_3$) δ (ppm): 8.24 (s, 1H), 7.80 (d, 2H), 7.40 (m, 5H), 7.10 (d, 2H), 6.78 (d, 4H), 6.62 (d, 1H), 6.42 (d, 1H), 5.84 (s, 1H), 4.98 (s, 2H), 1.23 (m, 3H), 1.10 (m, 18H); MS m/z 650 (M$^+$+1).

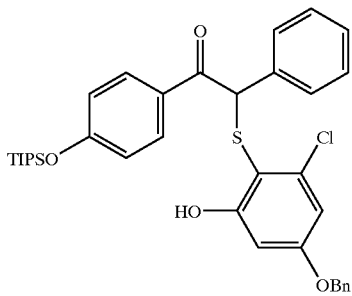

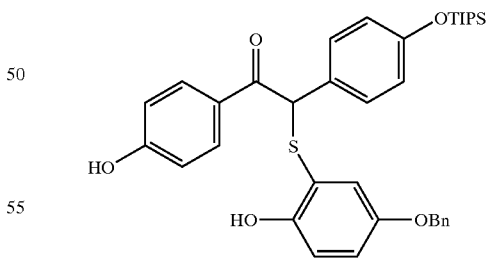

20m. Using the bromoketone 19d from Example 19 and compound 8 from Example 1, the desired product was obtained after silica gel chromatography using EtOAc/hexane (1:5) as the eluant. $^1$H NMR (500 MHz, CDCl$_3$) δ (ppm) 8.19 (s, 1H), 7.82 (d, 2H), 7.40 (m, 5H), 7.24 (m, 5H), 6.80 (d, 2H), 6.64 (d, 1H), 6.44 (d, 1H), 5.84 (s, 1H), 5.00 (s, 2H), 1.23 (m, 3H), 1.10 (m, 18H).

20p. Using the bromoketone 19b from Example 19 and compound 11 from Example 1, the desired product was obtained after silica gel chromatography using EtOAc/hexane (1:5) as the eluant. $^1$H NMR (500 MHz, acetone-$d_6$) δ (ppm): 7.95 (d, 2H), 7.40 (m, 5H), 7.20 (d, 2H), 6.80 (m, 7H), 6.20 (s, 1H), 4.85 (s, 2H), 1.23 (m,3H), 1.10 (m, 18H); MS m/z 616 (M$^+$+1).

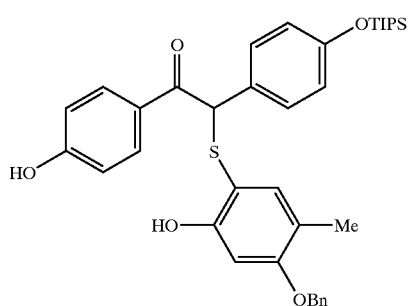

20q. Using the bromoketone 19b from Example 19 and compound 2 from Example 1, the desired product was obtained after silica gel chromatography using EtOAc/hexane (1:5) as the eluant. $^1$H NMR (500 MHz, CDCl$_3$) δ (ppm): 7.82 (d, 2H), 7.40 (m, 5H), 7.05 (d, 2H), 6.95 (s, 1H), 6.80 (d, 4H), 6.52 (s, 1H), 5.64 (s, 1H), 5.00 (s, 2H), 1.23 (m, 3H), 1.10 (m, 18H); MS m/z 629 (M$^+$+1).

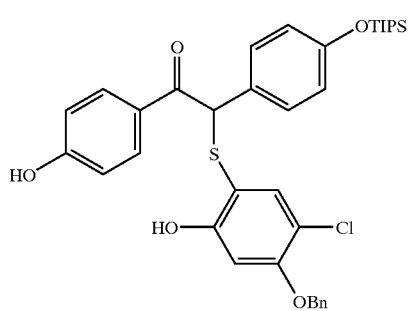

20r. Using the bromoketone 19b from Example 19 and compound 7 from Example 1, the desired product was obtained after silica gel chromatography using EtOAc/hexane (1:5) as the eluant. $^1$H NMR (500 MHz, CDCl$_3$) δ (ppm: 8.24 (s, 1H), 7.80 (d, 2H), 7.40 (m, 5H), 7.10 (d, 2H), 6.78 (d, 2H), 6.76 (d, 2H), 6.64 (d, 2H), 6.45 (d, 2H), 5.86 (s, 1H), 4.98 (s, 2H), 1.23 (m, 3H), 1.10 (m, 18H); MS m/z 650 (M$^+$+1).

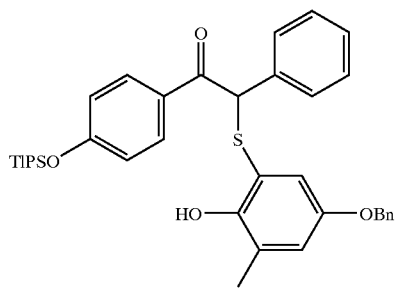

20s. Using the bromoketone 19d from Example 19 and compound 12 from Example 1, the desired product was obtained after silica gel chromatography using EtOAc/hexane (1:5) as the eluant. $^1$H NMR (500 MHz, CDCl$_3$) δ (ppm): 7.82 (d, 2H), 7.40 (m, 5H), 7.24 (m, 3H), 7.20 (d, 2H), 6.82 (d, 2H), 6.80 (d, 2H), 6.58 (d, 2H), 5.65 (s, 1H), 4.80 (d, 2H), 2.22 (s, 3H), 1.23 (m, 3H), 1.10 (m, 18H).

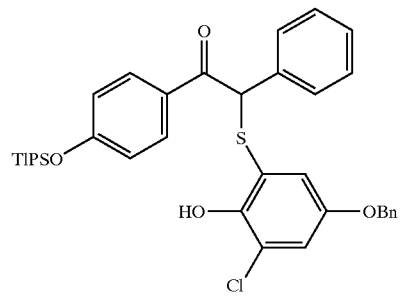

20t. Using the bromoketone 19d from Example 19 and compound 15 from Example 1, the desired product was obtained after silica gel chromatography using EtOAc/hexane (1:5) as the eluant. $^1$H NMR (500 MHz, CDCl$_3$) δ (ppm): 7.98 (s, 1H), 7.82 (d, 2H), 7.40 (m, 5H), 7.25 (m, 3H), 7.20 (d, 2H), 7.00 (d, 1H), 6.80 (d, 2H), 6.60 (d, 1H), 5.78 (s, 1H), 4.78 (d, 2H), 1.23 (m, 3H), 1.10 (m, 18H).

I

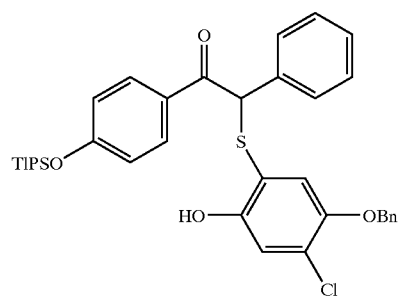

II

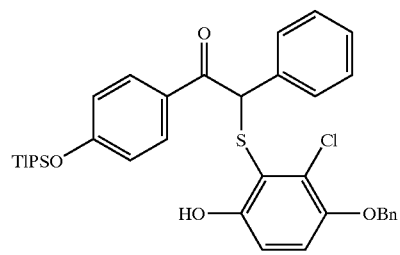

20u. Using the bromoketone 19d from Example 19 and the mixture of compounds 13 and 14 from Example 1, the two desired products I and II were obtained after silica gel chromatography using EtOAc/hexane (1:5) as the eluant.

I: $^1$H NMR (500 MHz, CDCl$_3$) ≠ (ppm): 7.80 (d, 2H), 7.40 (m, 5H), 7.25 (m, 3H), 7.16 (d, 2H), 7.04 (s, 1H), 6.80 (d, 2H), 6.60 (s, 1H), 5.78 (s, 1H), 4.80 (d, 2H), 1.23 (m, 3H), 1.10 (m, 18H).

II: $^1$H NMR (500 MHz, CDCl$_3$) δ (ppm): 7.80 (d, 2H), 7.65 (s, 1H), 7.44 (d, 1H), 7.40 (m, 5H), 7.25 (m, 5H), 6.96 (d, 1H), 6.80 (m, 3H), 6.00 (s, 1H), 5.15 (s, 2H), 1.23 (m, 3H), 1.10 (m, 18H).

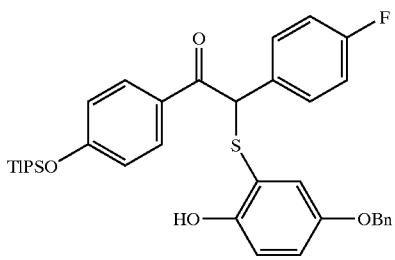

20v. Using the bromoketone 19h from Example 19 and compound 11 from Example 1, the desired product was obtained after silica gel chromatography using EtOAc/hexane (1:5) as the eluant. $^1$H NMR (500 MHz, CDCl$_3$) δ (ppm): 7.80 (d, 2H), 7.40 (m, 5H), 7.14 (m, 2H), 6.96 (m, 2H), 6.84 (m, 2H), 6.82 (d, 2H), 6.70 (d,1H), 5.68 (s, 1H), 4.86 d, 2H), 1.23 (m, 3H), 1.10 (m, 18H).

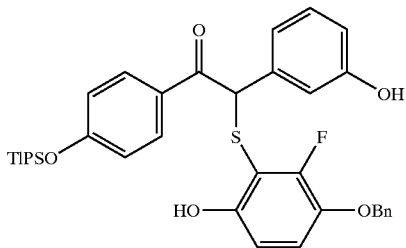

20w. Using the bromoketone 19c from Example 19 and compound 11 from Example 1, the desired product was obtained and used without further purification. $^1$H 500 MHz NMR(CDCl$_3$) ppm(δ): 1.07 (d, 18H), 1.2 (m, 3H), 4.84 (s, 2H), and 5.6 (s, 1H).

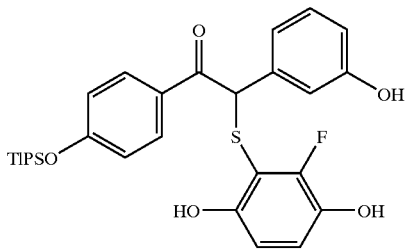

20x. Using a solution of the crude thiol (13.31 g, 83 mmol) from Example 2 and the crude bromoketone 19e (64 mmol) prepared in Example 19, the desired product was obtained as a yellow foam after silica gel chromatography with 30% EtOAc/hexane as the eluant.

$^1$H 500 MHz NMR(CDCl$_3$) ppm(δ): 1.09 (d, 18H), 1.28 (m, 3H), 4.65 (bd, 1H), 4.91 (bs, 1 H), 5.78 (s, 1H), 6.67–7.17 (m, 8H), 7.69 (s, 1H), 7.82 (d, 2H).

Utilizing the bromides prepared in Example 11 and compound 1 from Example 1 the following compounds were prepared:

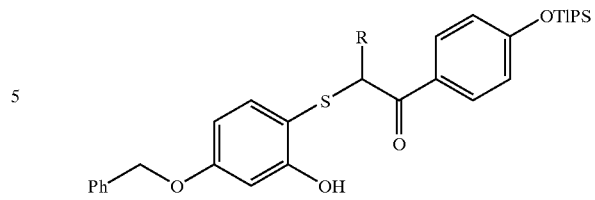

20y. R=Cyclohexyl: methylene chloride/hexanes (3:1) used as the chromatography eluant. $^1$H 500 MHz NMR (CDCl$_3$) ppm(δ): 1.12 (d, 18H), 1.11–2.34 (m, 15H), 4.19 (d, 1H), 5.0 (s, 2H), 6.44 (dd, 1H), 6.54 (d, 1H), 6.86 (m, 3H), 7.25–7.72 (m, 7H).

20z. R=Cyclopentyl: methylene chloride/hexanes (2:1) used as the chromatography eluant. $^1$H 500 MHz NMR (CDCl$_3$) ppm(δ):1.12 (d, 18H), 1.28–2.49 (m, 12H), 4.18 (d, 1H), 5.0 (s, 2H), 6.45–7.77 (m, 12H).

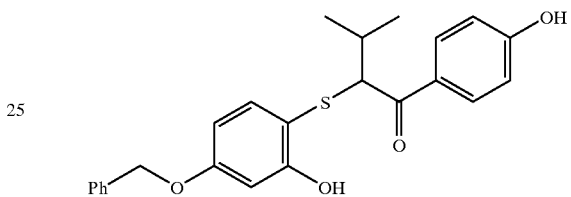

20aa. Utilizing the bromide prepared in Example 12 and compound 1 from Example 1, the desired product was obtained as a yellow oil after silica gel chromatography with 30% EtOAc/hexane as the eluant. $^1$H 500 MHz NMR (CDCl$_3$) ppm(δ): 1.00 (d, 3H), 1.21 (d, 3 H), 2.30 (m, 1H), 4.13 (d, 1H), 4.99 (s, 2H), 6.41–7.72 (m, 12H), 8.02 (bs, 1H), 8.80 (bs, 1H); MS m/z 409 (M$^+$).

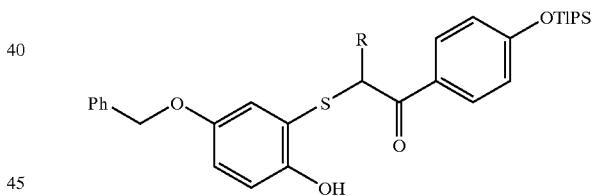

Utilizing the bromides prepared in Example 11 and compound 11 from Example 1, the following compounds were prepared:

20ab. R=Cyclohexyl: use methylene chloride/hexanes (3:1) as the chromatography eluant. $^1$H 500 MHz NMR (CDCl$_3$) ppm(δ): 1.12 (d, 18H), 1.11–2.3 (m, 15H), 4.24 (d, 1H), 4.89 (m, 2H), 6.8–7.6 (m, 12H).

20ac. R=Cyclopentyl: use methylene chloride/hexanes (2:1) as the chromatography eluant. $^1$H 500 MHz NMR (CDCl$_3$) ppm(δ):1.12 (d, 18H), 1.26–2.12 (m, 11H), 2.5 (m, 1H), 4.24 (d, 1H), 4.9 (m, 2H), 6.8–7.69 (m, 12H).

20ad. R=4-Pyridyl: isolated as a yellow oil using 30% EtOAc/hexane as the chromatography eluant. $^1$H 500 MHz NMR(CDCl$_3$) ppm(δ):1.12 (d, 18H), 1.28 (m, 3H), 4.84 (q, 2 H), 4.88 (s, 1H), 5.63 (s, 1H), and 6.69–8.50 (m, 16H).

20ae. R=3-Pyridyl: isolated as a yellow oil using 30% EtOAc/hexane as the chromatography eluant. $^1$H 500 MHz NMR(CDCl$_3$) ppm(δ):1.12 (d, 18H), 1.28-(m, 3H), 4.84 (q, 2H), 4.90 (s, 1H), 5.79 (s, 1H), and 6.70–8.50 (m, 16H).

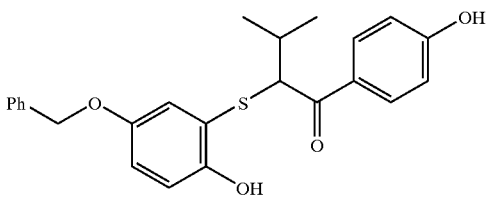

20af. Utilizing the bromide prepared in Example 12 and compound 11 from Example 1, the desired product was obtained as a yellow oil after silica gel chromatography with 30% EtOAc/hexane as the eluant. $^1$H 500 MHz NMR (CDCl$_3$) ppm(δ): 1.02 (d, 3H), 1.21 (d, 3 H), 2.34 (m, 1H), 4.13 (d, 1H), 4.90 (q, 2H), 6.25 (bs, 1H), 6.79–7.70 (m, 12H).

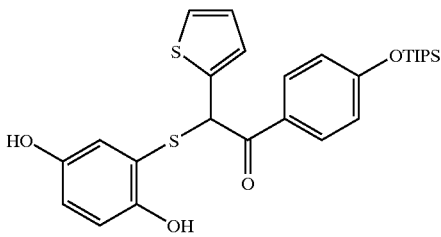

20ag. Utilizing the appropriate bromide prepared in Example 10 and the mercaptoquinol [prepared according to the method of Burton, etal, *J. Chem. Soc.*, 1952, 2193], the desired product was obtained as an orange/red oil after silica gel chromatography with 30% EtOAc/hexane as the eluant. $^1$H 500 MHz NMR(CDCl$_3$) ppm(δ): 1.10 (d, 18H), 1.27 (m, 3H), 6.00 (s, 1H), and 6.76–7.89 (m, 10H); MS m/z 515 (M$^+$).

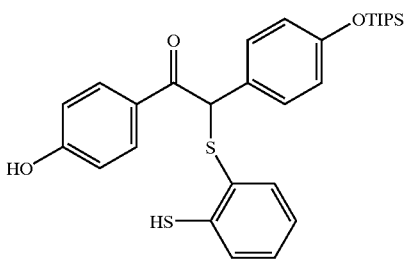

20ah. Using 0.36 g (2.5 mmol) of 1,2-benzenedithiol, purchased from the Aldrich Co., and the appropriate amount of the bromoketone 19b prepared in Example 19, the desired product was obtained after silica gel chromatography using EtOAc/hexane (1:5) as the eluant. $^1$H 500 MHz NMR (CDCl$_3$) ppm (δ): 7.82 (d, 2H), 7.38 (m, 2H), 7.1 (m, 2H), 7.1 (d, 2H), 6.79 (d, 2H), 6.75 (d, 2H), 5.84 (s, 1H), 1.2 (m, 3H), and 1.1 (d, 18H)

Example 21

Procedure for the Reductive-Cyclization Reaction for the Formation of Dihydro-Benzoxathiins

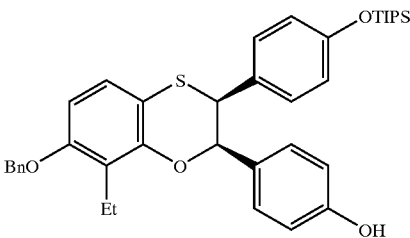

21a. Preparation of 7-Benzyloxy-8-ethyl-2-(4-hydroxyphenyl)-3-(4-triisopropylsilyoxyphenyl)-2,3-dihydro-1,4-benzoxathiin To a flask charged with 0.1 g (0.16 mmol) of thioketone 20 g, generated in Example 20, in dichloromethane (ca 0.04 M) was slowly added trifluoroacetic acid (TFA) (2×0.062 mL, 10 eq) under N$_2$ atmosphere at room temperature. To the stirred reaction mixture was slowly added triethylsilane (2×0.05 mL, 4 eq) and the resulting mixture stirred until starting material was consumed (approximately 5–6 hours, as monitored by TLC). The reaction mixture was poured into saturated NaHCO$_3$/ice water, stirred 10 minutes, and extracted with dichloromethane. The organic extract was washed with brine (2×50 mL), dried with Na$_2$SO$_4$, and concentrated in vacuo to afford a light yellow oil. Purification via flash chromatography (EtOAc/Hex=1:5) provided the desired compound as an oil. $^1$H NMR (400 MHz, CDCl$_3$) δ (ppm): 7.44 (m, 5H), 6.98 (d, 1H), 6.90 (d, 2H), 6.75 (d, 2H), 6.68 (d, 2H), 6.65 (d, 1H), 6.63 (d, 2H), 5.51 (d, J=2.3 Hz, 1H), 5.10 (s, 2H), 4.74 (brs, 1H), 4.32 (d, J=2.3 Hz, 1H), 2.77 (qd, 2H), 1.22 (m, 3H), 1.08 (d, 18H), 1.1 (m, 3H); MS m/z 628.5 (M++1).

Using the foregoing procedure, the following compounds were prepared:

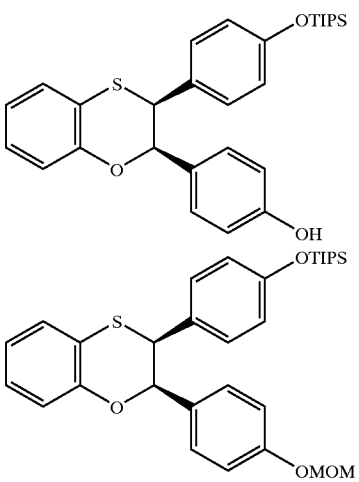

21b. Utilizing the thioketone 20a from Example 20, the desired dihydrobenzoxathiin without MOM protection was isolated after purification by silica gel chromatography with 10% EtOAc/hexane. $^1$H NMR (400 MHz, CDCl$_3$) δ (ppm): 7.2–6.98 (m, 4H), 6.85 (d, 2H), 6.78 (d, 2H), 6.66 (two d, 4H), 5.5 (d, J=2.2 Hz, 1H), 4.8 (s, 1H), 4.23 (d, J=2.1 Hz, 1H), 1.22 (m, 3H), 1.1 (d, 18H); MS m/z 515 (M⁺+23).

21c. The other dihydrobenzoxathiin with MOM protection was also isolated. ¹H NMR (400 MHz, CDCl₃) δ (ppm): 7.2–6.6 (m, 8H), 6.78 (d, 2H), 6.66 (d, 2H), 5.5 (d, J=2.4 Hz, 1H), 5.14 (s, 2H), 4.35 (d, J=2.1 Hz, 1H), 3.48 (s, 3H), 1.22 (m, 3H), 1.1 (d, 18H).

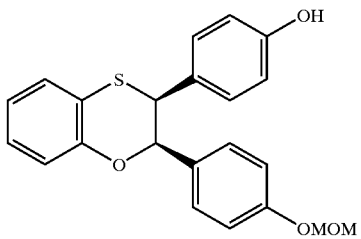

21d. The dihydrobenzoxathiin generated above, was desilylated using procedures described herein to give the product. ¹H NMR (400 MHz, CDCl₃) δ (ppm): 7.2–6.96 (m, 4H), 6.92 (two d, 4H), 6.82 (d, 2H), 6.6 (d, 2H), 5.52 (d, J=2.2 Hz, 1H), 5.16 (s, 2H), 4.68 (br s, 1H), 4.38 (d, J=2.2 Hz, 1H), 3.48 (s, 3H).

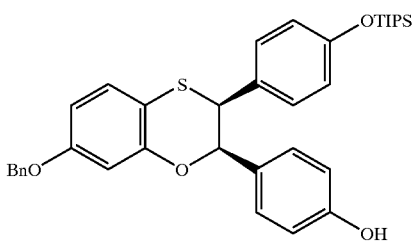

21e. The thioketone 20b generated in Example 20 was converted to the dihydrobenzoxathiin utilizing the above procedure with the exception that 20 equivalents of TFA and 15 equivalents of Et₃SiH were necessary to drive the reaction to completion. The desired product was isolated after purification by silica gel chromatography using 10% EtOAc/hexane as the eluant. ¹H NMR (400 MHz, CDCl₃) δ (ppm): 7.5–7.34 (m, 5H), 7.08 (d, 1H), 6.84 (d, 2H), 6.76 (d, 2H), 6.7 (dd,1H), 6.67 (d, 1H), 6.68 (two d, 4H), 5.5 (d, J=2.2 Hz, 1H), 5.04 (br q, 2H), 4.68 (s, 1H), 4.3 (d, J=2.2 Hz, 1H), 1.22 (m, 3H), 1.1 (d, 18H); MS m/z 515 (M⁺+23).

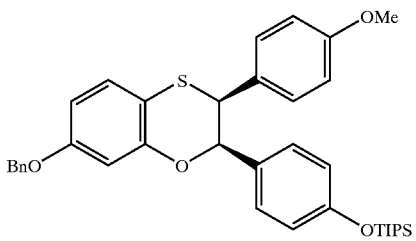

21f. The thioketone 20c generated in Example 20 was converted to the dihydrobenzoxathiin utilizing the above procedure with the exception that the reaction was run at −10° C. for 48 hours in the presence of 20 equivalents of TFA and 2 equivalents of Et₃SiH. The desired product was isolated after purification by silica gel chromatography using 10% EtOAc/hexane as the eluant. ¹H NMR (400 MHz, CDCl₃) δ (ppm): 7.5–7.3 (m, 5H), 7.1–6.6 (m, 11H), 5.54 (d, J=1.9 Hz, 1H), 5.06 (dd, 2H), 4.32 (d, 1H), 3.74 (s, 3H), 1.22 (m, 3H), 1.1 (d, 18H).

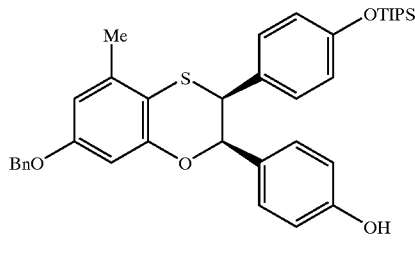

21g. Using the thioketone 20d from Example 20, the desired product was obtained after purification by silica gel chromatography using 5% EtOAc/hexane as the eluant. ¹H NMR (400 MHz, CDCl₃) δ (ppm): 7.46–7.32 (m, 5H), 6.84 (d, 2H), 6.78 (d, 2H), 6.66 (two d, 4H), 6.62 (d, 1H), 6.57 (d, 1H), 5.3 (d, J=2.2 Hz, 1H), 4.35 (d, 1H), 2.28 (s, 3H), 1.22 (m, 3H), 1.1 (d, 18H).

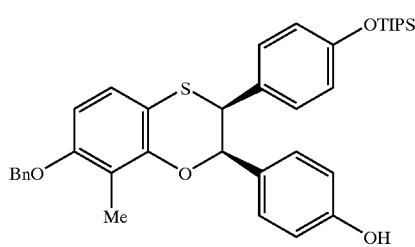

21h. Using the thioketone 20e from Example 20, the desired product was obtained after purification by silica gel chromatography using 5% EtOAc/hexane as the eluant. ¹H NMR (400 MHz, CDCl₃) δ (ppm): 7.5–7.3 (m, 5H), 6.98 (d, 1H), 6.9 (d, 1H), 6.76 (d, 2H), 6.6 (m, 5H), 5.51 (d, J=2.2 Hz, 1H), 5.1 (s, 2H), 4.8 (s, 1H), 4.32 (d, 1H), 2.4 (s, 3H), 1.22 (m, 3H), 1.1 (d, 18H).

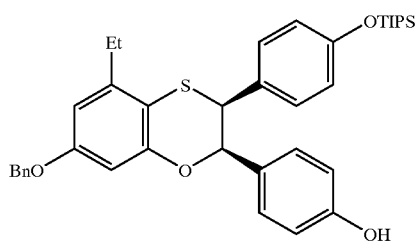

21i. Using the thioketone 20f from Example 20, the desired product was obtained after purification by silica gel chromatography using 5% EtOAc/hexane as the eluant. ¹H NMR (400 MHz, CDCl₃) δ (ppm): 7.5–7.3 (m, 5H), 6.85 (d, 2H), 6.78 (d, 2H), 6.66 (m, 5H), 6.56 (d, 1H), 5.48 (d, J=2.0 Hz, 1H), 5.04 (br q, 2H), 4.74 (br s, 1H), 4.34 (d, J=2.0 Hz, 1H), 2.64 (q, 2H), 1.3 (t, 3H), 1.24 (m, 3H), 1.1 (d, 18H).

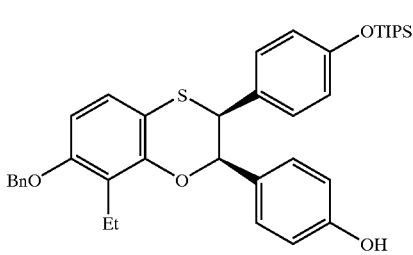

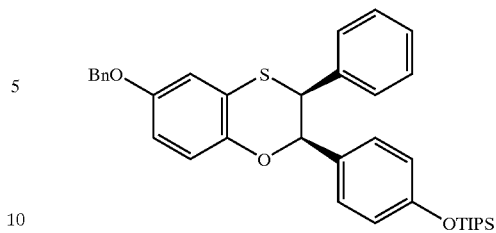

21j. Using the thioketone 20 g from Example 20, the desired product was obtained after purification by silica gel chromatography using 5% EtOAc/hexane as the eluant. $^1$H NMR (400 MHz, CDCl$_3$) δ (ppm: 7.5–7.3 (m, 5H), 6.98 (d, 1H), 6.9 (d, 2H) 6.74 (d, 2H), 6.7–6.6 (three d, 5H), 5.5 (d, J=2.3 Hz, 1H), 5.1 (s, 2H), 4.74 (br s, 1H), 4.32 (d, J=2.4 Hz, 1H), 2.79 (m, 2H), 1.22 (m, 3H), 1.1 (d & t, 21H); MS m/z 628.5 (M+1).

21m. Following the above procedure, with the exception that the reaction was run at 0° C. for three hours, and using 1.7 g (2.83 mmol) of the thioketone derivative 20j, obtained from Example 20, the desired product was obtained after purification by silica gel chromatography using 5% EtOAc/hexane as the eluant. $^1$H NMR (400 MHz, CDCl$_3$) δ (ppm): 7.5–7.34 (m, 5H), 7.2–7.1 (m, 3H), 6.94 (d, 1H), 6.9–6.82 (m, 5H), 6.4 (m, 3H), 5.48 (d, J=1.9 Hz, 1H), 5.05 (s, 2H), 4.36 (d, J=1.9 Hz, 1.22 (m, 3H), 1.1 (d, 18H).

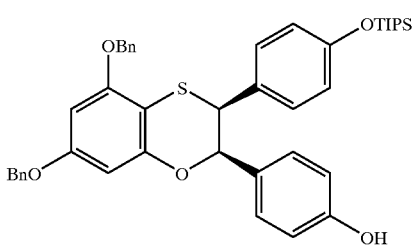

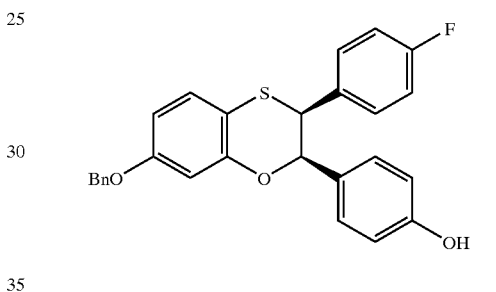

21k. Using the thioketone 20h from Example 20, the desired product was obtained after purification by silica gel chromatography using 5% EtOAc/hexane as the eluant. $^1$H NMR (400 MHz, CDCl$_3$) δ (ppm): 7.5–7.3 (m,10H), 6.84 (d, 2H), 6.78 (d, 2H), 6.66 (two d, 4H), 6.38 (s, 2H), 5.48 (d, J=2.1 Hz, 1H), 5.14 (s, 2H), 5.0 (q, 2H), 4.76 (br s, 1H), 4.32 (d, J=2.1 Hz, 1H), 1.22 (m, 3H), 1.1 (d, 18H).

21n. Using the thioketone 20k, obtained from Example 20, the desired product was obtained, which was subsequently desilylated using the procedure described herein. The desired product was obtained as an oil after purification by silica gel chromatography using 15% EtOAc/hexane as the eluant. $^1$H NMR (400 MHz, CDCl$_3$) δ (ppm): 7.5–7.32 (m, 5H), 7.09 (d, 1H), 6.9–6.8 (m, 6H), 6.73–6.7 (m, 4H), 5.52 (d, 1H), 5.04 (br q, 2H), 4.34 (d, 1H), 1.22 (m, 3H), 1.1 (d, 18H).

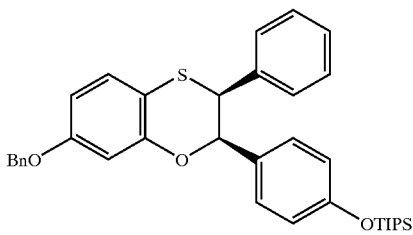

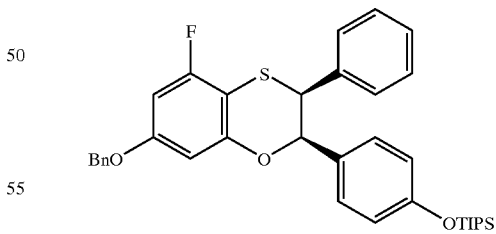

21l. Using the thioketone 20i, obtained from Example 20, the desired product was obtained after purification by silica gel chromatography using 5% EtOAc/hexane as the eluant. $^1$H NMR (400 MHz, CDCl$_3$) δ (ppm): 7.5–7.32 (m, 5H), 7.2–7.1 (m, 4H), 6.9–6.82 (m, 4H), 6.76–6.7 (m, 4H), 5.56 (d, 1H), 5.06 (br q, 2H), 4.36 (d, 1H), 1.22 (m, 3H), 1.1 (d, 18H).

21o. Using the thioketone 20l, from Example 20, the desired product was obtained after purification by silica gel chromatography using 5% EtOAc/hexane as the eluant. $^1$H NMR (500 MHz, CDCl$_3$) α (ppm): 7.5–7.3 (m, 5H), 7.22–7.10 (m, 3H), 6.90–6.80 (2d, 4H), 6.75 (d, 2H), 6.55 (d, 2H), 5.55 (d, J=2.1 Hz, 1H), 5.05 (d, 2H), 4.40 (d, J=2.1 Hz, 1H), 1.22 (m, 3H), 1.1 (d, 18H).

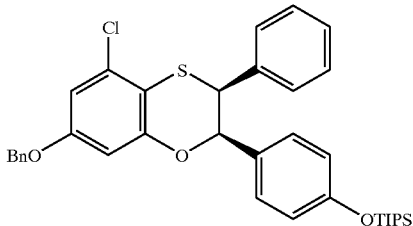

21p. Using the thioketone 20m, from Example 20, the desired product was obtained after purification by silica gel chromatography using 5% EtOAc/hexane as the eluant. ¹H NMR (500 MHz, CDCl$_3$) δ (ppm): 7.5–7.3 (m, 5H), 7.22–7.10 (m, 3H), 6.90–6.80 (2d, 4H), 6.73 (d, 2H), 6.64 (d, 2H), 5.50 (d, J=2.1 Hz, 1H), 5.05 (d, 2H), 4.43 (d, J=2.2 Hz, 1H), 1.23 (m, 3H), 1.10 (d, 18H).

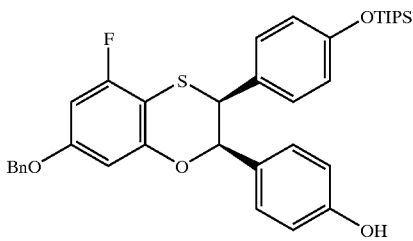

21q. Using the thioketone 20n, from Example 20, the desired product was obtained after purification by silica gel chromatography using 5% EtOAc/hexane as the eluant. ¹H NMR (500 MHz, CDCl$_3$) δ (ppm): 7.5–7.3 (m, 5H), 6.82 (d, 2H), 6.68 (d, 2H), 6.64 (d, 2H), 6.62 (d, 2H), 6.46 (d, 2H), 5.44 (d, J=1.9 Hz, 1H), 5.02 (d, 2H), 4.30 (d, J=2.0 Hz, 1H), 1.22 (m, 3H), 1.10 (d, 18H); MS m/z 618 (M$^+$+1).

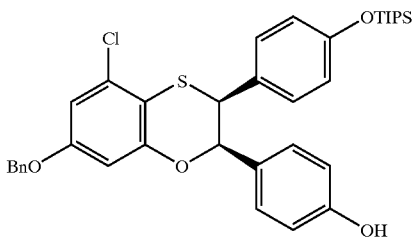

21r. Using the thioketone 20o, from Example 20, the desired product was obtained after purification by silica gel chromatography using 5% EtOAc/hexane as the eluant. ¹H NMR (400 MHz, CDCl$_3$) δ (ppm: 7.5–7.3 (m, 5H), 6.86 (d, 1H), 6.82 (d, 2H), 6.76 (d, 2H), 6.70 (d, 1H), 6.67(d, 2H), 6.65(d, 2H), 5.44 (d, J=2.0 Hz, 1H), 5.04 (s, 2H), 4.38 (d, J=1.9 Hz, 1H), 1.23 (m, 3H), 1.10 (d, 18H); MS m/z 634 (M$^+$+1).

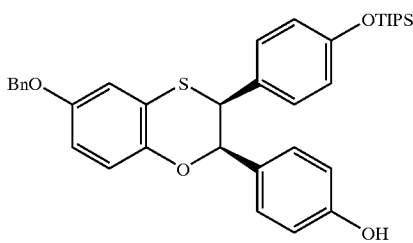

21s. Using the thioketone 20p, from Example 20, the desired product was obtained after purification by silica gel chromatography using 5% EtOAc/hexane as the eluant. ¹H NMR (500 MHz, CDCl$_3$) δ (ppm): 7.5–7.3 (m, 5H), 6.94 (d, 1H), 6.85 (d, 2H), 6.80 (d, 2H), 6.74 (dd, 2H), 6.65(m, 4H), 5.43 (d, J=2.1 Hz, 1H), 5.05 (d, 2H), 4.30 (d, J=2.1 Hz, 1H), 1.23 (m, 3H), 1.10 (d, 18H).

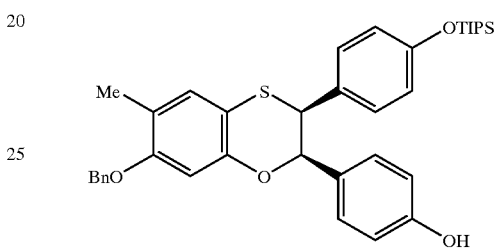

21t. Using the thioketone 20q, from Example 20, the desired product was obtained after purification by silica gel chromatography using 5% EtOAc/hexane as the eluant. ¹H NMR (500 MHz, CDCl$_3$) δ (ppm): 7.5–7.3 (m, 5H), 6.88 (s, 1H), 6.84 (d, 2H), 6.82 (d, 2H), 6.70 (d, 2H), 6.68 (d, 2H), 6.66 (s, 1H), 5.50 (d, 1H), 5.05 (s, 2H), 4.43 (d, 1H), 2.35 (s, 3H), 1.23 (m, 3H), 1.10 (d, 18H).

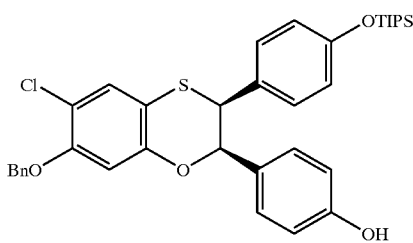

21u. Using the thioketone 20r, from Example 20, the desired product was obtained after purification by silica gel chromatography using 5% EtOAc/hexane as the eluant. ¹H NMR (500 MHz, CDCl$_3$) δ (ppm): 7.5–7.3 (m, 5H), 7.24 (s, 1H), 7.20 (s, 1H), 6.82 (d, 2H), 6.68 (d, 2H), 6.64 (m, 4H), 5.44 (d, J=2.0 Hz, 1H), 5.05 (d, 2H), 4.28 (d, J=2.3 Hz, 1H), 1.23 (m, 3H), 1.10 (d, 18H).

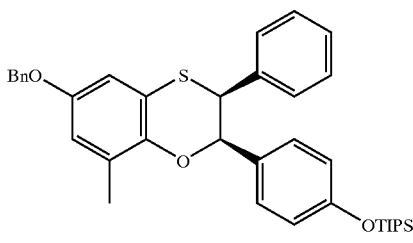

21v. Using the thioketone 20s, from Example 20, the desired product was obtained after purification silica gel chromatography using 5% EtOAc/hexane as the eluant. ¹H NMR (500 MHz, CDCl₃) δ (ppm): 7.5–7.3 (m, 5H), 7.05–7.20 (m, 4H), 6.90 (d, 2H) 6.88 (d, 2H), 6.78 (d, 2H), 6.70 (d, 1H), 6.65 (d, 1H), 5.30 (d, J=1.8 Hz, 1H), 5.05 (d, 2H), 4.20 (d, J=2.3 Hz, 1H), 1.23 (m, 3H), 1.10 (d, 18H).

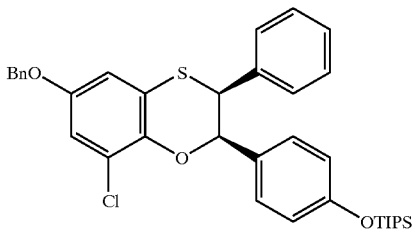

21w. Using the thioketone 20t, from Example 20, the desired product was obtained after purification by silica gel chromatography using 5% EtOAc/hexane as the eluant. ¹H NMR (500 MHz, CDCl₃) δ (ppm): 7.5–7.3 (m, 5H), 7.05–7.20 (m, 2H), 7.10 (m, 2H), 6.98 (d, 2H), 6.88 (m, 2H), 6.80 (m, 1H), 6.60 (d, 1H), 5.56 (d, J=1.8 Hz, 1H), 5.05 (d, 2H), 4.44 (d, J=2.3 Hz, 1H), 1.23 (m, 3H), 1.10 (d, 18H).

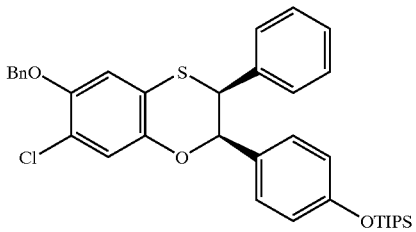

21x. Using the thioketone 20u-I, from Example 20, the desired product was obtained after purification by silica gel chromatography using 5% EtOAc/hexane as the eluant. ¹H NMR (500 MHz, CDCl₃) δ (ppm): 7.55 (d, 2H), 7.45 (t, 2H), 7.35 (t, 1H), 7.20 (d, 1H), 7.15 (m, 3H), 6.88 (d, 2H), 6.84 (d, 3H), 6.78 (d, 2H), 5.46 (d, J=2.1 Hz, 1H), 5.15 (s, 2H), 4.39 (d, J=2.1 Hz, 1H), 1.23 (m, 3H), 1.10 (d, 18H).

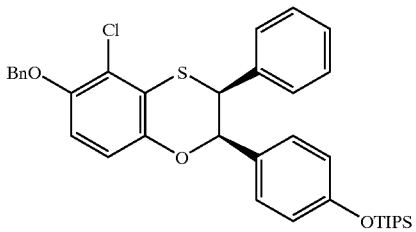

21y. Using the thioketone 20u-II, from Example 20, the desired product was obtained after purification by silica gel chromatography using 5% EtOAc/hexane as the eluant. ¹H NMR (500 MHz, CDCl₃) δ (ppm): 7.55 (d, 2H), 7.45 (t, 2H), 7.35 (t, 1H), 7.20 (d, 1H), 7.15 (t, 2H), 6.80–6.90 (m, 4H), 6.78 (d, 2H), 6.76 (d, 2H), 5.42 (d, J=2.1 Hz, 1H), 5.18 (s, 2H), 4.42 (d, J=2.1 Hz, 1H), 1.23 (m, 3H), 1.10 (d, 18H).

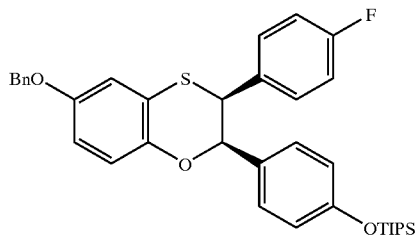

21z. Using the thioketone 20v, from Example 20, the desired product was obtained after purification by silica gel chromatography using 5% EtOAc/hexane as the eluant. ¹H NMR (500 MHz, CDCl₃) δ (ppm): 7.36–7.50 (m, 5H), 6.96 (d, 2H), 6.80–6.90 (m, 4H), 6.70–6.78 (m, 5H), 5.42 (d, J=2.1 Hz, 1H), 5.18 (s, 2H), 4.38 (d, J=2.1 Hz, 1H), 1.23 (m, 3H), 1.10 (d, 18H).

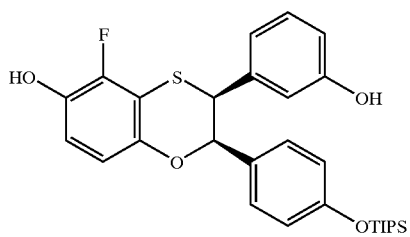

21aa. Using the thioketone 20x, from Example 20, the expected diol was realized as an off-white foam, after purification by silica gel chromatography with 30% EtOAc/hexane as the eluant. ¹H 500 MHz NMR(CDCl₃) ppm(δ): 1.11 (d, 18H), 1.25 (m, 3H), 4.33 (d, J=2.3 Hz, 1H), 5.42 (d, J=2.1 Hz, 1 H), 6.38–6.97 (m, 10H).

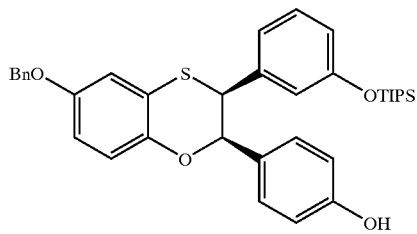

21ab. Using the thioketone 20w, from Example 20, the desired product was obtained after purification by silica gel chromatography using hexanes-ethyl acetate (85:15) as the eluant. ¹H 500 MHz NMR(CDCl₃) ppm(δ): 1.07 (d, 18H), 1.2 (m, 3H), 4.29 (d, 1H), 5.05 (s, 2H), and 5.49 (d, 1H).

Example 22

Chiral Separation of

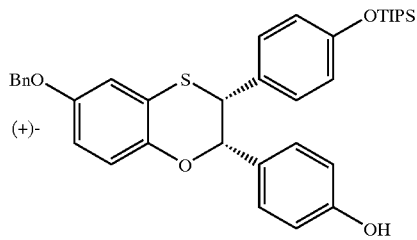

-continued

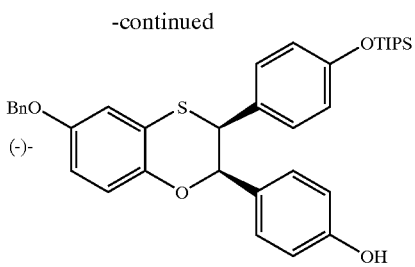

Each enantiomer of the racemic dihydrobenzoxathiin 21s, obtained from Example 21, was obtained via chiral chromatography using a Chiralpak® AD™ column, available from Daicel Chemical Industries, Ltd., with 30% isopropanol in hexane as the eluant.

The fast moving isomer: $[\alpha]_D=+184.4°$(c=0.725, MeOH).
The slow moving isomer: $[\alpha]_D=-188.5°$(c=0.74, MeOH).

Example 23

Chiral Separation of

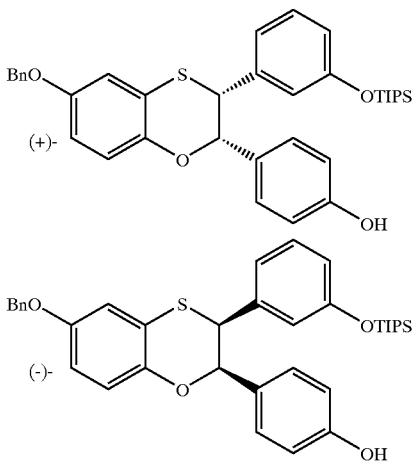

The positively rotating enantiomer of racemic 21ab, from Example 21, was obtained via chiral chromatography on a Chiralpak® AD™ 4.6×250 mm column, available from Daicel Chemical Industries, Ltd., using heptane-isopropanol (85:15) as the eluant, at a flow rate of 1 mL/min; retention time=5.2 min; $[\alpha]_D=+240.5°$(c=1.045, MeOH).

Example 24

Chiral Separation of

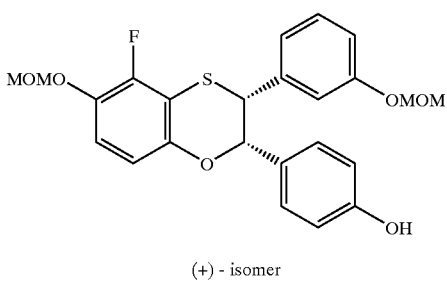

(+) - isomer

Step A:

To a solution of the product 21aa, obtained from Example 21, (5.38 g, 10 mmol) in distilled THF (60 mL) at 0° C. under $N_2$ was added MOMCl (1.9 mL, 26 mmol) followed by portion-wise addition of 95% NaH (0.6164 g, 22 mmol). The reaction became dark green but with time became yellow/brown. After stirring for 1 h, the reaction appeared mostly complete by TLC (30% EtOAc/hexane). Additional MOMCl (1 mL) was added to drive the reaction to completion. After 15 min., the reaction was partitioned between EtOAc and ice/water. The organic layer was collected, washed with brine, dried over $Na_2SO_4$, filtered, and concentrated in vacuo. The crude residue was used without further purification. $^1H$ 500 MHz NMR($CDCl_3$) ppm(δ): 1.10 (d, 18H), 1.25 (m, 3H), 3.39 (s, 3H), 3.58 (s, 3H), 4.36 (d, J=2.1 Hz, 1H), 5.00 (m, 2 H), 5.19 (s, 2H), 5.43 (d, J=1.9 Hz, 1 H), 6.57–7.03 (m, 10H).

Step B:

To a solution of the isolate from Step A (10 mmol) in distilled THF (60 mL) was added AcOH (0.76 mL, 13 mmol) at 0° C. under $N_2$ followed by a 1 M solution of TBAF in THF (11 mL, 11 mmol). After 5 min., the reaction was complete and the reaction was partitioned between saturated $NaHCO_3$ and EtOAc. The organic layer was collected, washed with brine, dried over $Na_2SO_4$, filtered, and concentrated in vacuo. The crude material was purified by silica gel chromatography with 40% EtOAc/hexane as the eluant to afford the desired product as a light yellow solid. $^1H$ 500 MHz NMR($CDCl_3$) ppm(δ): 3.39 (s, 3H), 3.59 (s, 3H), 4.37 (d, J=2.3 Hz,1H), 4.99 (s, 2 H), 5.20 (s, 2H), 5.44 (d, J=2.1 Hz, 1 H), 6.55–7.08 (m, 10H).

The racemic benzoxathiin was resolved via chiral chromatography on a Chiralcel OD column (150 mm diameter), using 20% iPrOH in heptane as the eluant (400 mL/min). The faster moving isomer was identified as the (+) enantiomer by a PDR-Chiral laser polarimeter.

Example 25

Preparation of Dihydrobenzoxathiin

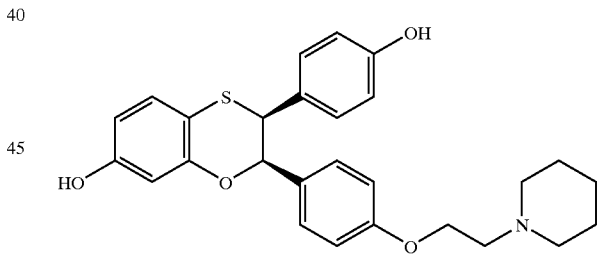

25a. Preparation of 3-(4-Hydroxyphenyl)-2-{4-[2-(1-piperidinyl)ethoxy]phenyl}-2,3-dihydro-1.4-benzoxathin-6-ol Step A To a stirred solution of a mixture of dihydrobenzoxathiin 21e (60 mg, 0.1 mmol), obtained from Example 21 (which was dried by the azeotropic method prior to use), triphenylphosphine (157 mg, 0.6 mmol), and 1-piperidineethanol (0.08 mL, 0.6 mmol) in 4 mL of anhydrous THF at 0° C. was added dropwise 0.118 mL (0.6 mmol)of diisopropyl azodicarboxylate (DIAD) over 0.2 hours. The resulting pale yellow solution was stirred at room temperature for 2–3 hours. The volatile components were removed in vacuo and the residue purified by flash chromatography (EtOAc/hexane=1:5, followed by 2–3% MeOH/dichloromethane) to give the desired product. $^1H$ NMR (400 MHz, $CDCl_3$) δ (ppm): 7.5–7.34 (m, 5H), 7.08 (d, 1H), 6.86 (d, 2H), 6.78–6.64 (m, 8H), 5.5 (d, 1H), 5.01 (br q, 2H), 4.3 (d, 1H), 4.2 (t, 2H), 275 (t, 2H), 2.5 (br s, 4H), 1.6 (m, 4H), 1.48 (m, 2H), 1.22 (m, 3H), 1.1 (d, 18H); MS m/z 712.4 (M⁺+1).

Step B

To a stirred solution of the adduct (71 mg, 0.098 mmol), generated in Step A, in 2 mL of EtOH/EtOAc/H₂O (7:2:1) was added 13 mg (1.2 eq) of palladium black and ammonium formate (62 mg, 10 eq). The resulting mixture was heated at 80° C. and monitored by TLC. After 3 hours, the reaction mixture was cooled to room temperature, filtered through a pad of Celite to remove the catalyst, and the filtrate was partitioned between water and EtOAc. The organic phase was separated, dried over MgSO₄ and concentrated in vacuo to give the desired product. ¹H NMR (400 MHz, CDCl₃) δ (ppm): 7.01 (d, 1H), 6.8 (d, 2H), 6.75 (d, 2H), 6.66 (two d, 4H), 6.54 (dd, 1H), 6.5 (d, 1H), 5.45 (d, J=2.3 Hz, 1H), 4.28 (d, J=2.3 Hz, 1H), 4.08 (t, 2H), 2.8 (t, 2H), 2.6 (br s, 4H), 1.68 (m, 4H), 1.5 (m, 2H), 1.22 (m, 3H), 1.1 (d, 18H).

Step C

To a stirred solution of a mixture of the debenzylated product generated in Step B and HOAc (10 eq) in THF was added a solution of tetrabutylammonium fluoride (3 eq) in THF at room temperature. The resulting solution was allowed to stir for two hours at room temperature and then poured into saturated aqueous NaHCO₃ and extracted with EtOAc. The organic layer was washed with brine, dried over MgSO₄, filtered, and evaporated. Purification by silica gel chromatography using 5–7% MeOH in methylene chloride as eluant afforded the desired product. ¹H NMR (400 MHz, CD₃OD) δ (ppm): 6.95 (d, 2H), 6.92 (d, 1H), 6.78 (d, 2H), 6.71 (d, 2H), 6.48 (d, 2H), 6.47 (d, 1H), 6.44 (dd, 1H), 5.47 (d, J=2.1 Hz, 1H), 4.37 (d, J=2.1 Hz, 1H), 4.1 (t, 2H), 2.85 (t, 2H), 2.65 (br s, 4H), 1.66 (m, 4H), 1.5 (m, 2H).

Using the above experimental procedures, the following compounds were prepared:

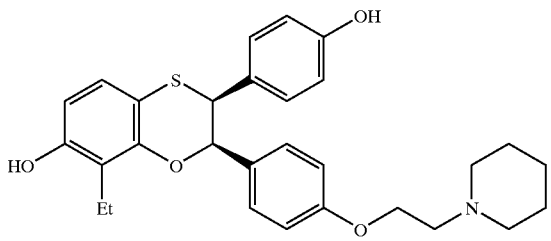

25b. Step A

The dihydrobenzoxathiin 21a, obtained from Example 21, was coupled with 1-piperidineethanol. After purification by silica gel chromatography, using 3% MeOH/CH₂Cl₂ as the eluant, the desired adduct was obtained. ¹H NMR (400 MHz, CDCl₃) δ (ppm): 6.98 (d, 1H), 6.92 (d, 2H), 6.74 (two d, 4H), 6.65 (d, 1H), 6.62 (d, 2H), 5.5 (d, 1H), 5.1 (s, 2H), 4.31 (d, 1H), 4.09 (m, 2H), 2.75 (t, 2H), 2.55 (m, 2H), 2.5 (m, 4H), 1.6 (m, 4H), 1.45 (m, 2H), 1.22 (m, 3H), 1.1 (m, 21H).

Step B

The adduct generated in Step A was debenzylated to give the desired product. ¹H NMR (400 MHz, CDCl₃) δ (ppm): 6.92 (d, 1H), 6.89 (d, 2H), 6.72 (d & d, 4H), 6.62 (d, 2H), 6.5 (d, 1H), 5.5 (d, J=2.2 Hz, 1H), 4.3 (d, J=2.2 Hz, 1H), 4.1 (m, 2H), 2.8 (t, 2H), 2.68 (m, 2H), 2.58 (br s, 4H), 1.64 (m, 4H), 1.48 (m, 2H), 1.2 (m, 3H), 1.09 (d & m, 21H).

Step C

The debenzylated product from Step B was desilylated. The desired product was obtained as a white solid. ¹H NMR (400 MHz, CD₃OD) δ (ppm): 7.0 (d, 2H), 6.79 (d, 2H), 6.76 (d, 1H), 6.71 (d, 2H), 6.47 (d, 3H), 5.46 (d, J=2.2 Hz, 1H), 4.38 (d, 1H), 4.08 (t, 2H), 2.8 (t, 2H), 2.5 (m, 2H), 2.6 (m, 4H), 1.62 (m, 4H), 1.5 (m, 2H), 1.1 (t, 3H); MS m/z 493.2 (M⁺+1).

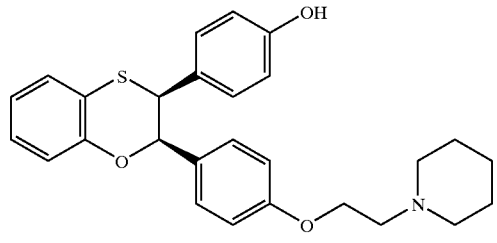

25c. Step A

The dihydrobenzoxathiin 21b, obtained from Example 21, was coupled with 1-piperidineethanol. After purification by silica gel chromatography using 3% MeOH/CH₂Cl₂ as eluant, the desired adduct was obtained. ₁H NMR (400 MHz, CDCl₃) δ (ppm): 7.14–6.92 (m, 4H), 6.8 (d, 2H), 6.76 (d, 2H), 6.72 (d, 2H), 6.64 (d, 2H), 5.48 (d, J=2.2 Hz, 1H), 4.34 (d, J=2.1 Hz, 1H), 4.1 (m, 2H), 2.85 (m, 2H), 2.6 (m, 4H), 1.65 (m, 4H), 1.5 (m, 2H), 1.22 (m, 3H), 1.1 (d, 18H).

Step B

The adduct from Step A was desilylated. The desired product was obtained as a white solid. ¹H NMR (400 MHz, CD₃OD) δ (ppm): 7.14–6.92 (m, 4H), 6.06 (d, 2H), 6.78 (d, 2H), 6.72 (d, 2H), 6.48 (d, 2H), 5.48 (d, J=2.1 Hz, 1H), 4.44 (d, 1H), 4.1 (t, 2H), 2.78 (t, 2H), 2.58 (br s, 4H), 1.64 (m, 4H), 1.5 (m, 2H); MS m/z 450.2 (M⁺+1)

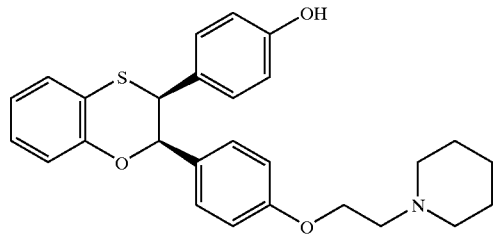

25d. Step A

The dihydrobenzoxathiin 21d, obtained from Example 21, was coupled with 1-piperidineethanol. After purification by silica gel chromatography with 3% MeOH/CH₂Cl₂, the desired adduct was obtained as an oil. ¹H NMR (400 MHz, CDCl₃) δ (ppm): 7.14–6.94 (m, 4H), 6.96 (d, 2H), 6.84 (two d, 4H), 6.66 (d, 2H), 5.5 (d, J=2.1 Hz, 1H), 5.12 (s, 2H), 4.5 (d, J=2.1 Hz, 1H), 4.04 (t, 2H), 3.42 (s, 3H), 2.75 (t, 2H), 2.55 (br s, 4H), 1.6 (m, 4H), 1.48 (m, 2H); MS m/z 495.2 (M⁺+1).

Step B

The adduct (10 mg, 0.02 mmol) from Step A was deprotected with TFA (10 eq) and MeOH (6 eq) in CH₂Cl₂ at room temperature to afford the desired product. ¹H NMR (400 MHz, CD₃OD) δ (ppm): 7.14–6.92 (m, 4H), 6.84 (two d, 4H), 6.66 (d, 2H), 6.6 (d, 2H), 5.45 (d, J=2.2 Hz, 1H), 4.45 (d, J=2.2 Hz, 1H), 4.05 (t, 2H), 2.8 (t, 2H), 2.6 (br s, 4H), 1.6 (m, 4H), 1.5 (m, 2H); MS m/z 450.2 (M⁺+1).

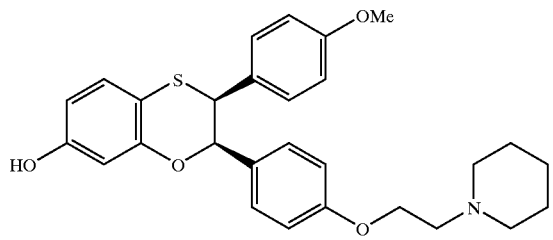

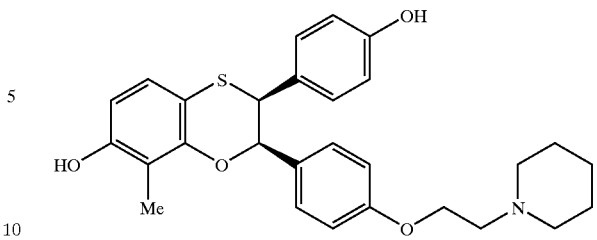

25e. Step A

The dihydrobenzoxathiin 21f, generated from Example 21, was desilylated using the procedure described above in Step C. The desired product was obtained as a white solid. $^1$H NMR (400 MHz, CDCl$_3$) δ (ppm): 7.5–7.3 (m, 5H), 7.2 (d, 1H), 6.9 (d, 2H), 6.88 (d, 2H), 6.68 (m, 6H), 5.53 (d, J=2.2 Hz, 1H), 4.33 (d, J=2.3 Hz, 1H), 3.75 (s, 3H).

Step B

The desilylated product obtained from Step A was coupled with 1-piperidineethanol. After purification by silica gel chromatography with 3% MeOH/CH$_2$Cl$_2$, the desired adduct was obtained. $^1$H NMR (400 MHz, CDCl$_3$) δ (ppm): 7.5–7.3 (m, 5H), 7.08 (d, 1H), 6.9 (d, 2H), 6.84 (d, 2H), 6.76 (d, 2H), 6.66 (m, 4H), 5.52 (d, 1H), 5.03 (s, 2H), 4.32 (d, 1H), 4.06 (t, 2H), 3.75 (s, 3H), 2.75 (t, 2H), 2.5 (br s, 4H), 1.6 (m, 4H), 1.45 (m, 2H).

Step C

The adduct generated in Step B was debenzylated to give the product. $^1$H NMR (400 MHz, CD$_3$OD) δ (ppm): 6.96 (d, 2H), 6.92 (d, 1H), 6.82 (d, 2H), 6.78 (d, 2H), 6.63 (d, 2H), 6.48 (dd, 1H), 6.44 (d, 1H), 5.5 (d, J=2.2 Hz, 1H), 4.42 (d, J=2.2 Hz, 1H), 4.08 (t, 2H), 3.68 (s, 3H), 2.78 (t, 2H), 2.59 (br s, 4H), 1.6 (m, 4H), 1.48 (m, 2H); MS m/z 479.4 (M$^+$+1).

25g. Step A

The dihydrobenzoxathiin 21h, obtained from Example 21, was coupled with 1-piperidineethanol. After purification by silica gel chromatography with 3% MeOH/CH$_2$Cl$_2$, the desired adduct was obtained.

Step B

The adduct generated in Step A was debenzylated. After purification by silica gel chromatography using 5% MeOH/CH$_2$Cl$_2$ as the eluant, the desired product was obtained as an oil. $^1$H NMR (400 MHz, CDCl$_3$) δ (ppm): 6.9 (d, 2H), 6.89 (d, 1H), 6.73 (m, 4H), 6.62 (d, 2H), 6.52 (d, 1H), 5.5 (d, 1H), 4.3 (d, 1H), 4.1 (br s 2H), 2.8 (br t, 2H), 2.6 (br s, 4H), 2.2 (s, 3H), 1.6 (m, 4H), 1.5 (m, 2H), 1.22 (m, 3H), 1.1 (d, 18H).

Step C

The debenzylated product from Step B was desilylated. The desired product was obtained as a white solid. $^1$H NMR (400 MHz, CD$_3$OD) δ (ppm): 7.02 (d, 2H), 6.76 (d, 2H), 6.7 (d, 2H), 6.47 (two d, 3H), 5.48 (d, J=2.3 Hz, 1H), 4.38 (d, J=2.3 Hz, 1H), 4.1 (t, 2H), 2.8 (t, 2H), 2.6 (br s, 4H), 2.1 (s, 3H), 1.6 (m, 4H), 1.5 (m, 2H), MS m/z 479.2 (M$^+$+1).

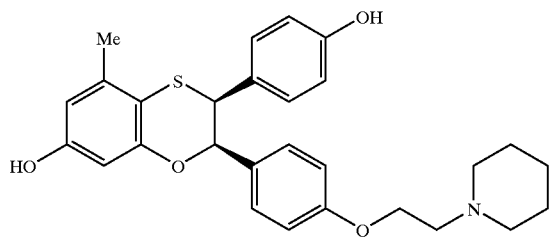

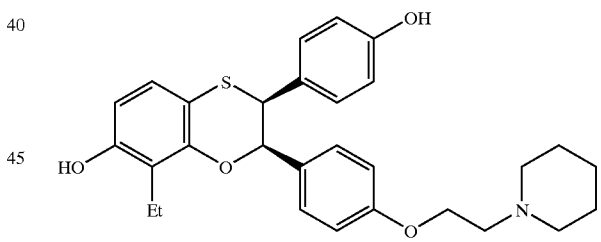

25f. Step A

The dihydrobenzoxathiin 21g, obtained from Example 21, was coupled with 1-piperidineethanol. After purification by silica gel chromatography with 3% MeOH/CH$_2$Cl$_2$, the desired adduct was obtained. $^1$H NMR (400 MHz, CDCl$_3$) δ (ppm): 6.83 (d, 2H), 6.75 (d, 2H), 6.69 (d, 2H), 6.62 (d, 2H), 6.5 (d, 1H), 6.48 (d, 1H), 5.42 (br s, 1H), 4.3 (br s, 1H), 4.06 (t, 2H), 2.78 (t, 2H), 2.5 (br s, 4H), 1.6 (m, 4H), 1.44 (m, 2H), 1.22 (m, 3H), 1.1 (d, 18H).

Step B and C

The adduct generated in Step A was debenzylated and desilylated. The desired product was obtained as a white solid. $^1$H NMR (400 MHz, CD$_3$OD) δ (ppm): 6.94 (d, 2H), 6.76 (d, 2H), 6.7 (d, 2H), 6.49 (d, 2H), 6.4 (d, 1H), 6.32 (d, 1H), 5.43 (d, J=2.3 Hz, 1H), 4.4 (d, J=2.3 Hz, 1H), 4.08 (t, 2H), 2.8 (t, 2H), 2.6 (br s, 4H), 2.18 (s, 3H), 1.64 (m, 4H), 1.5 (m, 2H); MS m/z 479.2 (M$^+$+1).

25h. Step A

The dihydrobenzoxathiin 21j, obtained from Example 21, was coupled with 1-piperidineethanol. After purification by silica gel chromatography with 3% MeOH/CH$_2$Cl$_2$, the desired adduct was obtained.

Step B and C

The adduct generated in Step A was debenzylated and desilylated. The desired product was obtained as a white solid after silical gel chromatography with 5% MeOH/CH$_2$Cl$_2$ as eluant. $^1$H NMR (400 MHz, CD$_3$OD) δ (ppm): 6.94 (d, 2H), 6.76 (d, 2H), 6.7 (2H, d), 6.48 (d, 2H), 6.41 (d, 1H), 6.3 (d, 1H), 5.44 (d, J=2.2 Hz, 1H), 4.4 (d, J=2.2 Hz, 1H), 4.08 (t, 2H), 2.8 (t, 2H), 2.62 (br s, 4H), 2.6 (q, 2H), 1.6 (m, 4H), 1.45 (m, 2H), 1.2 (t, 3H); MS m/z 493.2 (M$^+$+1).

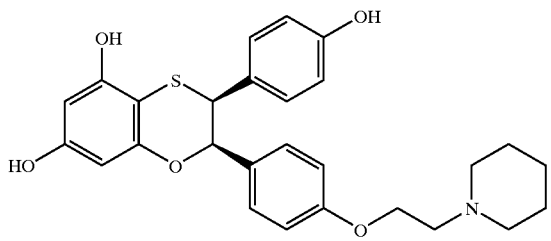

25i. Step A

The dihydrobenzoxathiin 21k, obtained from Example 21, was coupled with 1-piperidineethanol. After purification by silica gel chromatography with 3% MeOH/CH$_2$Cl$_2$, the desired adduct was obtained. $^1$H NMR (400 MHz, CDCl$_3$) δ (ppm): 7.5–7.3 (m, 10H), 6.86 (d, 2H), 6.78 (d, 2H), 6.74 (d, 2H), 6.64 (d, 2H), 6.38 (s, 2H), 5.48 (d, 1H), 5.14 (s, 2H), 5.02 (q, 2H), 4.32 (d, 1H), 4.08 (t, 2H), 2.8 (t, 2H), 2.5 (br s, 4H), 1.62 (m, 4H), 1.5 (m, 2H), 1.22 (m, 3H), 1.1 (d, 18H).

Step B

The adduct generated in Step A was debenzylated. After purification by silica gel chromatography using 5% MeOH/CH$_2$Cl$_2$ as eluant, the desired product was obtained as an oil.

Step C

The debenzylated product from Step B was desilylated. The desired product was obtained as a white solid. $^1$H NMR (400 MHz, CD$_3$OD) δ (ppm): 6.94 (d, 2H), 6.78 (d, 2H), 6.72 (d, 2H), 6.5 (d, 2H), 6.06 (d, 1H), 6.02 (d, 1H), 5.42 (d, J=2.2 Hz, 1H), 4.33 (d, J=2.2 Hz, 1H), 4.09 (t, 2H), 2.8 (t, 2H), 2.6 (br s, 4H), 1.64 (m, 4H), 1.5 (m, 2H); MS m/z 482.2 (M$^+$+1).

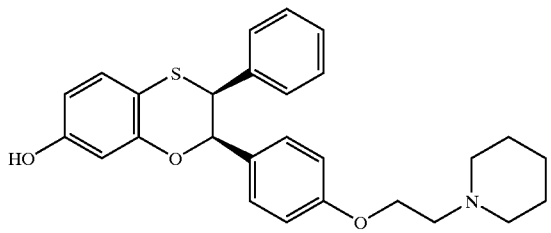

25j. Step A

The dihydrobenzoxathiin 21l, generated from Example 21, was desilylated. The desired product was obtained as a white solid. $^1$H NMR (400 MHz, CDCl$_3$) δ (ppm: 7.48–7.32 (m, 5H), 7.2–7.1 (m, 4H), 6.94–6.84 (two d, 4H), 6.7 (m, 4H), 5.56 (d, J=2.1 Hz, 1H), 5.04 (br q, 2H), 4.74 (s, 1H), 4.37 (d, J=2.1 Hz, 1H).

Step B

The desilylated product obtained from Step A was coupled with 1-piperidineethanol. After purification by silica gel chromatography with 3% MeOH/CH$_2$Cl$_2$, the desired adduct was obtained. $^1$H NMR (400 MHz, CDCl$_3$) δ (ppm): 7.5–7.32 (m, 5H), 7.2–7.04 (m, 4H), 6.94–6.86 (m, 4H), 6.76–6.66 (m, 4H), 5.54 (br s, 1H), 5.04 (br s, 2H), 4.38 (br s, 1H1), 4.06 (t, 2H), 2.76 (t, 2H), 2.5 (br s, 4H), 1.6 (m, 4H), 1.42 (m, 2H).

Step C

The adduct generated in Step B was debenzylated to afford the desired product. $^1$H NMR (400 MHz, CD$_3$OD) δ (ppm): 7.2–7.14 (m, 3H), 6.94 (m, 3H), 6.9 (d, 2l1), 6.74 (d, 2H), 6.48 (dd, 1H), 6.45 (d, 1H), 5.53 (d, J=2.3 Hz, 1H), 4.46 (d, 1H), 4.06 (t, 2H), 2.78 (t, 2H), 2.58 (br s, 4H), 1.62 (m, 4H), 1.5 (m, 2H); MS m/z 449.2 (M$^+$+1) The material was resolved via chiral chromatography on a Chiralpak® AD™ column, available from Daicel Chemical Industries, Ltd., using 20% EtOH in hexane as the eluant.

The fast moving isomer: $[\alpha]_D$=+334.3° (c=1.205, MeOH).

The slow moving isomer: $[\alpha]_D$=–342° (c=1.09, MeOH).

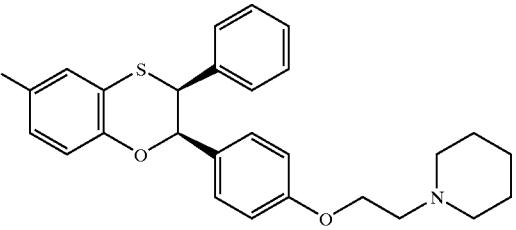

25k. Step A

The dihydrobenzoxathiin 21m, generated from Example 21, was desilylated. The desired product was obtained as a white solid. $^1$H NMR (400 MHz, CDCl$_3$) δ (ppm): 7.5–7.3 (m, 5H), 7.2–7.1 (m, 3H), 6.96 (m, 2H), 6.92 (d, 1H), 6.88 (d, 2H), 6.84 (d, 1H), 6.74 (dd, 1H), 6.66 (d, 2H), 5.48 (d, J=2.1 Hz, 1H), 5.04 (s, 2H), 4.37 (d, J=2.1 Hz, 1H); MS m/z 428.2 (M$^+$+1).

Step B

The desilylated product obtained from Step A was coupled with 1-piperidineethanol. After purification by silica gel chromatography with 3% MeOH/CH$_2$Cl$_2$, the desired adduct was obtained.

Step C

The adduct generated in Step B was debenzylated to afford the desired product. $^1$H NMR (400 MHz, CD$_3$OD) δ (ppm): 7.14–7.02 (m, 3H), 6.92 (m, 4H), 6.8 (d, 1H), 6.74 (d, 2H), 6.58 (d, 1H), 6.51 (dd, 1H), 5.42 (br s, 1H), 4.45 (br s, 1H), 4.06 (t,2H), 2.78 (t, 2H), 2.55 (br s, 4H), 1.6 (m, 4H), 1.5 (m, 2H); MS m/z 449.2 (M$^+$+1). The material was resolved via chiral chromatography on a Chiralpak® AD™ column, available from Daicel Chemical Industries, Ltd., using 20% EtOH in hexane as the eluant.

The fast moving isomer: $[\alpha]_D$=+324° (c=1.36, MeOH).

The slow moving isomer: $[\alpha]_D$=–313° (c=1.37, MeOH).

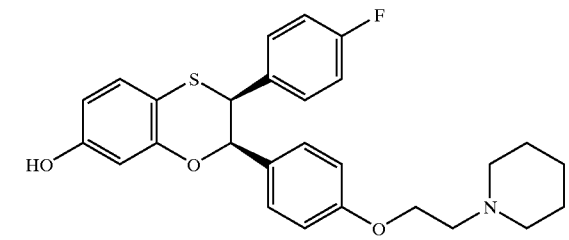

25l. Step A

The desilylated product 21n, obtained from Example 21, was coupled with 1-pieridineethanol. After purification by silica gel chromatography with 3% MeOH/CH$_2$Cl$_2$, the desired adduct was obtained.

Step B

The adduct generated in Step A was debenzylated to afford the desired product. $^1$H NMR (400 MHz, CD$_3$OD) δ (ppm): 6.98–6.76 (m, 9H), 6.5 (dd, 1H), 6.46 (d, 1H), 5.52 (d, J=2.3 Hz, 1H), 4.5 (d, 1H), 4.05 (t, 2H), 2.80 (t, 2H), 2.62 (br s, 4H), 1.62 (m, 4H), 1.5 (m, 2H); MS m/z 466.2 (M$^+$).

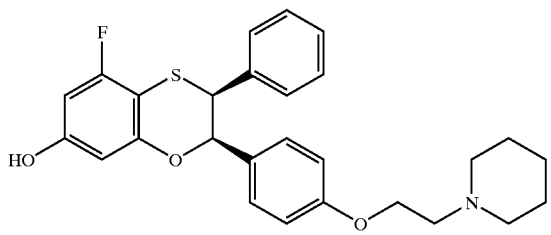

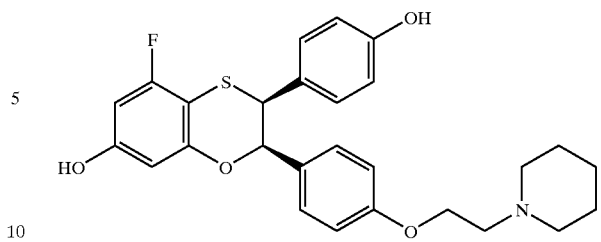

25m. Step A

The dihydrobenzoxathiin 21o, generated from Example 21, was desilylated. The desired product was obtained as a white solid. $^1$H NMR (500 MHz, CDCl$_3$) δ (ppm): 7.5–7.3 (m, 5H), 7.2–7.1 (m, 3H), 6.85 (2d, 4H), 6.68 (d, 2H), 6.55 (d, 1H), 5.04 (s, 2H), 4.40(d, 1H).

Step B

The desilylated product obtained from Step A was coupled with 1-piperidineethanol. After purification by silica gel chromatography with 3% MeOH/CH$_2$Cl$_2$, the desired adduct was obtained.

Step C

A mixture of the adduct (80 mg, 0.144 mmol), generated in Step B, 20 mg of palladium black, and 5 drops of AcOH in 4 mL of ethanol, was stirred under a balloon of hydrogen gas and monitored by TLC. After 18 hours, the reaction mixture was filtered through a pad of Celite to remove the catalyst, and the filtrate was neutralized by the addition of saturated, aqueous NaHCO$_3$ solution and extracted by EtOAc. The organic layer was separated, dried over MgSO$_4$ and concentrated in vacuo to give the desired product. $^1$H NMR (500 MHz, CD$_3$OD) δ (ppm): 7.20–7.02 (m, 3H), 6.92 (m, 4H), 6.78 (d, 2H), 6.30 (d, 2H), 5.55 (d, J=2.1 Hz, 1H), 4.50(d, J=2.3 Hz, 1H), 4.06 (t, 2H), 2.78 (t, 2M), 2.55 (br s, 4H), 1.6 (m, 4H), 1.5 (m, 2H); MS m/z 467 (M$^+$+1).

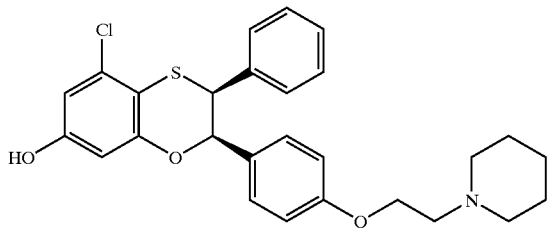

25n. Step A

The dihydrobenzoxathiin 21p, generated from Example 21, was desilylated using the. The desired product was obtained as a white solid. $^1$H NMR (500 MHz, CDCl$_3$) δ (ppm): 7.5–7.3 (m, 5H), 7.2–7.1 (m, 3H), 6.95 (d, 2H), 6.90 (d, 1H), 6.85 (d, 2H), 6.70 (d, 2H), 6.65 (d, 1H), 5.50 (d, 1H), 5.04 (s, 2H), 4.42 (d, 1H).

Step B

The desilylated product obtained from Step A was coupled with 1-piperidineethanol. After purification by silica gel chromatography with 3% MeOH/CH$_2$Cl$_2$, the desired adduct was obtained.

Step C

The adduct, generated in Step B, was debenzylated to afford the desired product. $^1$H NMR (500 MHz, CD$_3$)D) δ (ppm): 7.14–7.02 (m, 3H), 6.92 (d, 2H), 6.85 (d, 2H), 6.74 (d, 2H), 6.58 (d, 1H), 6.41 (d, 1H), 5.52 (d, J=2.3 Hz, 1H), 4.55 (d, J=2.3 Hz, 1H), 4.06 (t, 2H), 2.78 (t, 2H), 2.55 (br s, 4H), 1.6 (m, 4H), 1.5 (m, 2H); MS m/z 483 (M$^+$+1).

25o. Step A

The dihydrobenzoxathiin 21q, obtained from Example 21, was coupled with 1-piperidineethanol. After purification by silica gel chromatography with 3% MeOH/CH$_2$Cl$_2$ the desired adduct was obtained. $^1$H NMR (500 MHz, CDCl$_3$) δ (ppm): 7.5–7.3 (m, 5H), 6.80 (d, 2H), 6.70 (2d, 4H), 6.60 (d, 2H), 6.40 (2d, 2H), 5.40 (s, 1H), 4.90 (d, 2H), 4.20 (s, 1H), 4.08 (t, 2H), 2.8 (t, 2H), 2.5 (br s, 4H), 1.62 (m, 4H), 1.5 (m, 2H), 1.22 (m, 3H), 1.1 (d, 18H).

Step B and C

The adduct, generated in Step A, was debenzylated and desilylated. The desired product was obtained as a white solid. $^1$H NMR (500 MHz, CD$_3$OD) δ (ppm): 6.93 (d, 3H), 6.78 (d, 2H), 6.69 (d, 2H), 6.50 (d, 2H), 6.28 (m, 1H), 5.46 (d, J=1.8 Hz, 1H), 4.39 (d, J=2.2 Hz, 1H), 4.05 (t, 2H), 2.8 (t, 2H), 2.6 (br s, 4H), 1.64 (m, 4H), 1.5 (m, 2H); MS m/z 482.2 (M$^+$+1).

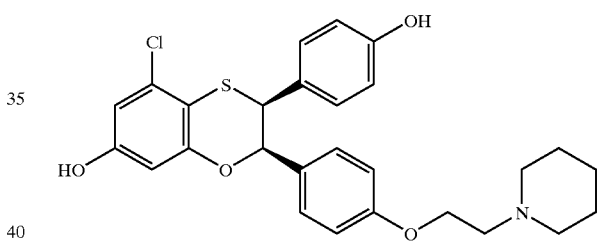

25p. Step A

The dihydrobenzoxathiin 21r, obtained from Example 21, was coupled with 1-piperidineethanol. After purification by silica gel chromatography with 3% MeOH/CH$_2$Cl$_2$ the desired adduct was obtained. $^1$H NMR (500 MHz, CDCl$_3$) δ (ppm): 7.5–7.3 (m, 5H), 6.85 (m, 3H), 6.70 (d, 4H), 6.63 (d, 2H), 6.60 (d, 1H), 5.42 (s, 1H), 5.02 (d, 2H), 4.40 (s, 1H), 4.08 (t, 2H), 2.8 (t, 2H), 2.5 (br s, 4H), 1.62 (m, 4H), 1.5 (m, 2H), 1.22 (m, 3H), 1.1 (d, 18H).

Step B

The adduct, generated in Step A, was debenzylated to afford the desired product. $^1$H NMR (500 MHz, CD$_3$OD) δ (ppm): 6.82 (d, 2H), 6.78 (d, H), 6.70 (2d, 4H), 6.62 (d, 2H), 6.58 (d, 1H), 5.40 (d, 1H), 4.30 (d, 1H), 4.06 (t, 2H), 2.78 (t, 2H), 2.55 (br s, 4H), 1.6 (m, 4H), 1.5 (m, 2H); MS m/z 655 (M$^+$+1).

Step C

The debenzylated product from Step B was desilylated. The desired product was obtained as a white solid. $^1$H NMR (500 MHz, CD$_3$OD) δ (ppm): 6.92 (d, 2H), 6.75 (d, 2H), 6.68(d, 2H), 6.60 (d, 1H), 6.50 (d, 2H), 6.42(d, 1H), 5.42 (d, J=2.2 Hz, 1H), 4.42 (d, J=2.3 Hz, 1H), 4.07 (t, 2H), 2.78 (t, 2H), 2.55 (brs, 4H), 1.62 (m, 4H), 1.48 (m, 2H); MS m/z 499 (M$^+$+1).

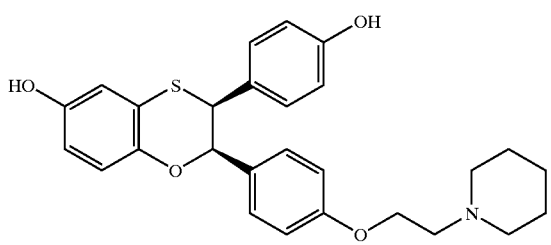

25q. Step A

The dihydrobenzoxathiin 21s, obtained from Example 21, was coupled with 1-piperidineethanol. After purification by silica gel chromatography with 3% MeOH/CH$_2$Cl$_2$ the desired adduct was obtained.

Step B and C

The adduct, generated in Step A, was debenzylated and desilylated. The desired product was obtained as a white solid after purification by silica gel chromatography with 5% MeOH/CH$_2$Cl$_2$ as eluant. $^1$H NMR (500 MHz, acetone-d$_6$) δ (ppm): 7.04 (d, 2H), 6.90 (dd, 3H), 6.72 (d, 2H), 6.64 (d, 1H), 6.59 (d, 2H), 6.57(dd, 1H), 5.44 (d, J=2.3 Hz, 1H), 4.52 (d, J=2.1 Hz, 1H), 4.08 (t, 2H), 2.8 (t, 2H), 2.62 (br s, 4H), 2.6 (q, 2H), 1.6 (m, 4H), 1.45 (m, 2H), 1.2 (t, 2H); MS m/z 465 (M$^+$+1).

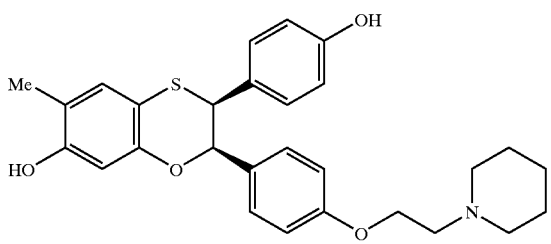

25r. Step A

The dihydrobenzoxathiin 21t, obtained from Example 21, was coupled with 1-piperidineethanol. After purification by silica gel chromatography with 3% MeOH/CH$_2$Cl$_2$ the desired adduct was obtained.

Step B and C

The adduct, generated in Step A, was debenzylated and desilylated. The desired product was obtained as a white solid after purification by silica gel chromatography with 5% MeOH/CH$_2$Cl$_2$ as eluant. $^1$H NMR (500 MHz, acetone-d$_6$) δ (ppm): 7.00 (d, 2H), 6.85 (s, 1H), 6.80 (d, 2H), 6.78 (d, 2H), 6.59 (d, 2H), 6.52 (s, 1H), 5.49 (d, J=2.3 Hz, 1H), 4.65(d, J=2.2 Hz, 1H), 4.08 (t, 2H), 2.8 (t, 2H), 2.62 (br s, 4H), 2.6 (q, 2H), 1.6 (m, 4H), 1.45 (m, 2H), 1.2 (t, 2H); MS m/z 479 (M$^+$+1).

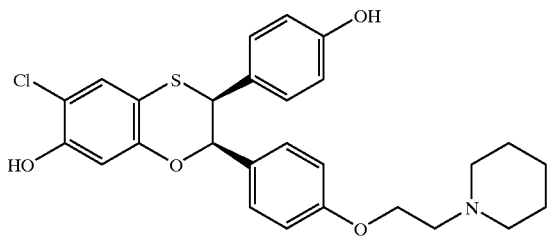

25s. Step A

The dihydrobenzoxathiin 21u, obtained from Example 21, was coupled with 1-piperidineethanol. After purification by silica gel chromatography with 3% MeOH/CH$_2$Cl$_2$ the desired adduct was obtained. $^1$H NMR (500 MHz, CDCl$_3$) δ (ppm): 7.5–7.3 (m, 5H), 7.20 (s, 1H), 6.85 (d, 2H), 6.70 (2d, 4H), 6.63 (d, 2H), 6.60 (s, 1H), 5.42 (s, 1H), 5.02 (q, 2H), 4.30 (s, 1H), 4.08 (t, 2H), 2.8 (t, 2H), 2.5 (br s, 4H), 1.62 (m, 4H), 1.5 (m, 2H), 1.22 (m, 3H), 1.1 (d, 18H).

Step B p The adduct, generated in Step A, was debenzylated to afford the desired product. $^1$H NMR (500 MHz, acetone-d$_6$) δ (ppm): 7.10 (s, 1H), 6.98 (d, 2H), 6.82 (d, 2H), 6.78 (d, 2H), 6.70 (d, 2H), 6.68 (s, 1H), 5.50 (d, 1H), 4.50 (d, 1H), 4.06 (t, 2H), 2.78 (t, 2H), 2.55 (br s, 4H), 1.6 (m, 4H), 1.5 (m, 2H).

Step C

The debenzylated product from Step B was desilylated. The desired product was obtained as a white solid. $^1$H NMR (500 MHz, acetone-d$_6$) δ (ppm): 7.12 (s, 1H), 7.02 (d, 2H), 6.80 (dd, 4H), 6.69 (s, 1H), 6.60 (d, 2H), 6.42 (d, 1H), 5.55 (d, J=2.3 Hz, 1H), 4.54 (d, J=2.1 Hz, 1H), 4.07 (t, 2H), 2.78 (t, 2H), 2.55 (brs, 4H), 1.62 (m, 4H), 1.48 (m, 2H); MS m/z 499 (M$^+$+1).

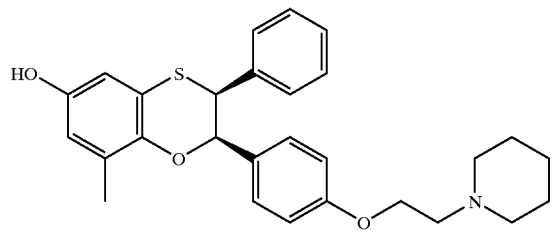

25t. Step A

The dihydrobenzoxathiin 21v, generated from Example 21, was desilylated. The desired product was obtained as a white solid. $^1$H NMR (500 MHz, CDCl$_3$) δ (ppm): 7.5–7.3 (m, 5H), 7.2–7.1 (m, 5H), 6.95 (m, 3H), 6.64–6.70 (m, 2H), 5.46 (d, J=1.8 Hz, 1H), 5.04 (s, 2H), 4.42 (d, J=2.0 Hz, 1H).

Step B

The desilylated product obtained from Step A was coupled with 1-piperidineethanol. After purification by silica gel chromatography with 3% MeOH/CH$_2$Cl$_2$, the desired adduct was obtained.

Step C

The adduct, generated in Step B, was debenzylated to afford the desired product. $^1$H NMR (500 MHz, CD$_3$OD) δ (ppm: 7.00–7.12 (m, 6H), 6.90 (d, 2H), 6.75 (d, 2H), 6.42 (s, 1H), 5.42 (d, J=2.1 Hz, 1H), 4.48 (d, J=2.3 Hz, 1H), 4.06 (t, 2H), 2.78 (t, 2H), 2.55 (br s, 4H), 1.6 (m, 4H), 1.5 (m, 2H); MS m/z 463 (M$^+$+1).

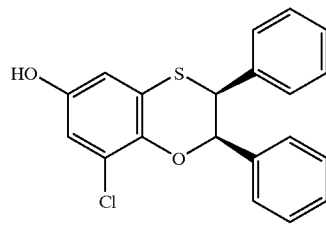

25u. Step A

The dihydrobenzoxathiin 21w, generated from Example 21, was desilylated. The desired product was obtained as a white solid. $^1$H NMR (500 MHz, CDCl$_3$) δ (ppm): 7.5–7.3 (m, 5H), 7.2–7.1 (m, 3H), 6.95 (d, 2H), 6.92 (d, 2H), 6.90 (d, 1H), 6.78 (d, 1H), 6.70 (d, 2H), 5.52 (d, J=2.1 Hz, 1H), 5.04 (s, 2H), 4.46 (d, J=2.2 Hz, 1H).

Step B

The desilylated product obtained from Step A was coupled with 1-piperidineethanol. After purification by silica gel chromatography with 3% MeOH/CH$_2$Cl$_2$, the desired adduct was obtained.

Step C

The adduct, generated in Step B, was debenzylated to afford the desired product. $^1$H NMR (500 MHz, CD$_3$OD) δ (ppm): 7.05–7.15 (m, 5H), 6.90 (d, 2H), 6.79 (d, 2H), 6.65 (d, 1H), 6.55 (d, 1H), 5.50 (d, J=2.1 Hz, 1H), 4.62 (d, J=2.3 Hz, 1H), 4.10 (t, 2H), 2.80 (t, 2H), 2.60 (br s, 4H), 1.6 (m, 4H), 1.5 (m, 2H); MS m/z 483 (M$^+$+1).

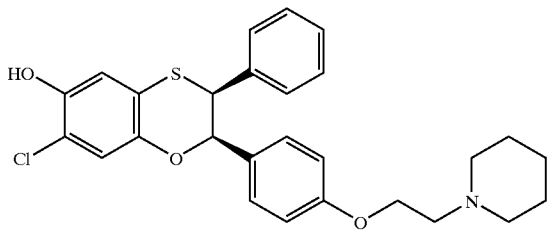

25v. Step A

The dihydrobenzoxathiin 21x, generated from Example 21, was desilylated. The desired product was obtained as a white solid. $^1$H NMR (500 MHz, CDCl$_3$) δ (ppm): 7.5–7.3 (m, 5H), 7.2–7.1 (m, 3H), 7.08 (s, 1H), 6.95 (d, 2H), 6.86 (m, 3H), 6.70 (d, 2H), 5.42 (d, J=2.1 Hz, 1H), 5.14 (s, 2H), 4.40 (d, J=2.0 Hz, 1H).

Step B

The desilylated product obtained from Step A was coupled with 1-piperidineethanol. After purification by silica gel chromatography with 3% MeOH/CH$_2$Cl$_2$, the desired adduct was obtained.

Step C

The adduct, generated in Step B, was debenzylated to afford the desired product. $^1$H NMR (500 MHz, CD$_3$OD) δ (ppm): 7.05–7.15 (m,. 3H), 6.95 (m, 3H), 6.90 (d, 2H), 6.75 (d, 2H), 6.72 (s, 1H), 5.45 (d, J=2.0 Hz, 1H), 4.52 (d, J=2.3 Hz, 1H), 4.10 (t, 2H), 2.80 (t, 2H), 2.60 (br s, 4H), 1.6 (m, 4H), 1.5 (m, 2H); MS m/z 483 (M$^+$+1).

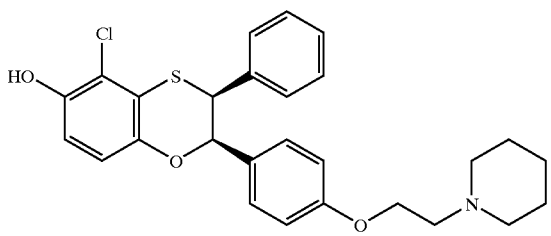

25w. Step A

The dihydrobenzoxathiin 21y, generated from Example 21, was desilylated. The desired product was obtained as a white solid. $^1$H NMR (500 MHz, CDCl$_3$) δ (ppm): 7.5–7.3 (m, 5H), 7.2–7.1 (m, 3H), 6.92–6.80 (m, 5H), 6.78 (d, 2H), 6.70 (d, 2H), 5.40 (d, J=2.1 Hz, 1H), 5.20 (s, 2H), 4.46 (d, J=2.0 Hz, 1H).

Step B

The desilylated product obtained from Step A was coupled with 1-piperidineethanol. After purification by silica gel chromatography with 3% MeOH/CH$_2$Cl$_2$, the desired adduct was obtained.

Step C

The adduct, generated in Step B, was debenzylated to afford the desired product. $^1$H NMR (500 MHz, CD$_3$OD) δ (ppm): 7.05–7.15 (m, 3H), 6.95 (d, 2H), 6.90 (d, 2H), 6.80 (d, 1H), 6.75 (d, 2H), 6.70 (d, 1H), 5.38 (d, J=1.8 Hz, 1H), 4.56 (d, J=2.1 Hz, 1H), 4.06 (t, 2H), 2.78 (t, 2H), 2.60 (br s, 4H), 1.6 (m, 4H), 1.5 (m, 2H); MS m/z 483 (M$^+$+1).

The material was resolved via chiral chromatography on a Chiralpak® AD™ column, available from Daicel Chemical Industries, Ltd., using 20% EtOH in hexane as the eluant.

The fast moving isomer: [α]$_D$=+260.9° (c=1.025, MeOH).

The slow moving isomer: [α]$_D$=−254.4° (c=0.95, MeOH).

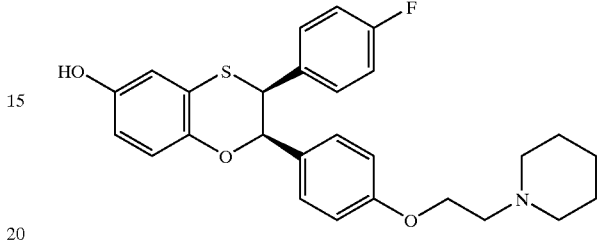

25x. Step A

The dihydrobenzoxathiin 21z, generated from Example 21, was desilylated. The desired product was obtained as a white solid. $^1$H NMR (500 MHz, CDCl$_3$) δ (ppm): 7.5–7.3 (m, 5H), 6.95 (d, 2H), 6.90(m, 3H), 6.85 (m, 3H), 6.74 (dd, 1H), 6.70 (d, 2H), 5.45 (d, J=1.9 Hz, 1H), 5.05 (s, 2H), 4.35 (d, J=2.1 Hz, 1H).

Step B

The desilylated product obtained from Step A was coupled with 1-piperidineethanol. After purification by silica gel chromatography with 3% MeOH/CH$_2$Cl$_2$, the desired adduct was obtained, which was used without further purification.

Step C

The adduct, generated in Step B, was debenzylated to afford the desired product. $^1$H NMR (500 MHz, CD$_3$OD) δ (ppm): 6.98 (d, 2H), 6.94 (m, 2H), 6.80 (m, 5H), 6.60 (d, 1H), 6.75 (dd, 1H), 5.40 (d, J=1.8 Hz, 1H), 4.50 (d, J=2.1 Hz, 1H), 4.08 (t, 2H), 2.78 (t, 2H), 2.60 (br s, 4H), 1.6 (m, 4H), 1.5 (m, 2H); MS m/z 466 (M$^+$+1).

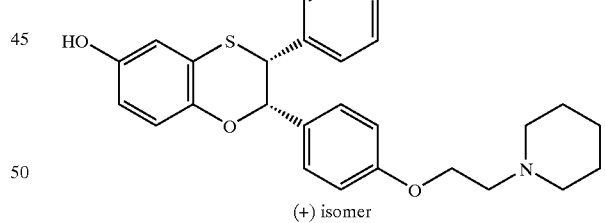

(+) isomer

25y. Step A

The fast moving (+)-dihydrobenzoxathiin obtained from Example 22 was coupled with 1-piperidineethanol. After purification by silica gel chromatography with 3% MeOH/CH$_2$Cl$_2$, the desired adduct was obtained.

Step B and Step C

The adduct, generated in Step A, was debenzylated and desilylated. The desired product was obtained as a white solid after purification by silica gel chromatography with 5% MeOH/CH$_2$Cl$_2$ as eluant. $^1$H NMR (500 MHz, acetone-d$_6$) δ (ppm): 6.90 (d, 2H), 6.78 (d, 1H), 6.72 (d, 2H), 6.70 (d, 2H), 6.60 (d, 1H), 6.50 (d, 1H), 6.48 (d, 2H), 5.38 (d, J=2.0 Hz, 1H), 4.38 (d, J=2.3 Hz, 1H), 4.08 (t, 2H), 2.8 (t, 2H), 2.62 (br s, 4H), 2.6 (q, 2H), 1.6 (m, 4H), 1.45 (m, 2H), 1.2

(t, 2H); MS m/z 465 (M$^+$+1); [α]$_D$=+276.80 (c=0.49, MeOH).

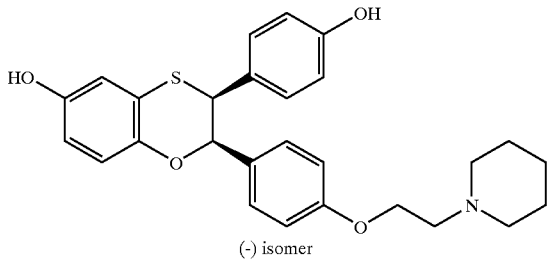

(−) isomer

25z. Step A

The slow moving (−)-dihydrobenzoxathiin obtained from Example 22 was coupled with 1-piperidineethanol. After purification by silica gel chromatography with 3% MeOH/CH$_2$Cl$_2$, the desired adduct was obtained.

Step B and Step C

The adduct, generated in Step A, was debenzylated and desilylated. The desired product was obtained as a white solid after purification by silica gel chromatography with 5% MeOH/CH$_2$Cl$_2$ as eluant. $^1$H NMR (500 MHz, acetone-d$_6$) δ (ppm): 6.90 (d, 2H), 6.78 (d, 1H), 6.72 (d, 2H), 6.70 (d, 2H), 6.60 (d, 1H), 6.50 (d, 1H), 6,48 (d, 2H), 5.38 (d, J=2.0 Hz, 1H), 4.38 (d, J=2.3 Hz, 1H), 4.08 (t, 2H), 2.8 (t, 2H), 2.62 (br s, 4H), 2.6 (q, 2H), 1.6 (m, 4H), 1.45 (m, 2H), 1.2 (t, 2H); MS m/z 465 (M$^+$+1); [α]$_D$=−263.3° (c=0.515, MeOH).

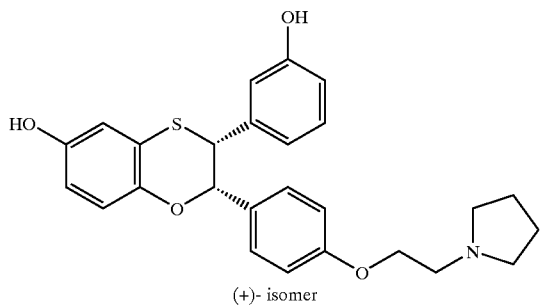

(+)- isomer

25aa. Step A

To a stirred solution of a mixture of chiral (+)-dihydrobenzoxathiin (9.2 g, 15.6 mmol), obtained from Example 23, triphenylphosphine (28.2 g, 107.5 mmol), and 1-pyrrolidineethanol (12.6 mL, 107.5 mmol) in 300 mL of anhydrous THF at 0° C. was added dropwise 21.1 mL (107.5 mmol) of diisopropyl azodicarboxylate (DIAD). The resulting solution was stirred further for 15 min, then at room temperature for 20 min, and finally at 40° C. for 2 h. The mixture was concentrated in vacuo and the residue was partitioned between ethyl acetate/2N HCl, and the organic phase separated and washed twice more with 2N HCl, then twice with saturated sodium bicarbonate, and finally with brine; dried magnesium sulfate; filtered, and evaporated. The residue was taken up in ether and the insoluble triphenylphosphine oxide removed by filtration. The filtrate was evaporated and the process of removing the triphenylphosphine oxide was repeated twice more. The final residue was purified by silica gel chromatography (Biotage) using 5% MeOH/dichloromethane as eluant to give the desired product containing a some triphenylphoshine oxide, which was used without further purification. $^1$H NMR (500 MHz, CDCl$_3$) δ (ppm): 7.5–7.34 (m, 5H), 6.9–6.7 (m, 10H), 6.26 (d, 1H), 5.46 (d, 1H), 5.01 (s, 2H), 4.26 (d, 1H), 4.05 (t, 2H), 2.87 (t, 2H), 2.6 (m, 4H), 1.8 (m, 4H), 1.22 (m, 3H), 0.97 (d, 18H); MS m/z 700 (M$^+$+1).

Step B

A mixture of the adduct (~13 g, 18.7 mmol) generated Step A, 3 g (28 mmol) of palladium black and ammonium formate (30 g, 476 mmol) in 300 mL of EtOH/EtOAc/H$_2$O (7:2: 1) was heated at 80° C. for 1 h. The reaction mixture was filtered through a pad of Celite to remove the catalyst, washed thoroughly with hot EtOAc, and the filtrate was partitioned between water and EtOAc. The organic phase was separated, dried over MgSO$_4$, filtered, and concentrated in vacuo to give the crude product which was used without purification. $^1$H NMR (500 MHz, CD$_3$OD) δ (ppm): 7.09–6.52 (m, 10H), 6.19 (d, 1H), 5.44 (d, 1H), 4.38(d, 1H), 4.1 (t, 2H), 2.9 (t, 2H), 2.6 (m, 4H), 1.8 (m, 4H), 1.22 (m, 3H), 0.97 (d, 18H); MS m/z 610 (M$^+$1).

Step C

To a stirred solution of a mixture of the debenzylated product (~13 g, 18.7 mmol), generated in Step B, and 21 mL (374 mmol) of HOAc in 200 mL of THF was added 56 mL (56 mmol) a 1M solution of tetrabutylammonium fluoride in THF at room temperature. The resulting solution was allowed to stir for two hours at room temperature and then concentrated in vacuo. The concentrate was diluted with EtOAc and washed thrice with saturated aqueous NaHCO$_3$ and then twice with water. The organic layer was dried over MgSO$_4$, filtered, and evaporated. Purification by silica gel chromatography using 4–11% MeOH in methylene chloride as eluant afforded the desired product. $^1$H NMR (500 MHz, methanol-d$_4$) δ (ppm): 7.00 (d, 2H), 6.86 (t, 1H), 6.80 (d, 1H), 6.75 (d, 2H), 6.60 (d, 1H), 6.58 (dd, 1H), 6.54 (d, 1H), 6.50 (d, 1H), 6.35 (d, 1H), 5.38 (d, J=1.9 Hz, 1H), 4.38 (d, J=2.2 Hz, 1H), 4.05 (t, 2H), 2.90 (t, 1H), 2.70 (m, 4H), 1.85 (m, 4H); MS m/z 450 (M$^+$+1); [α]$_D$=+315.9° (c=1.1, MeOH).

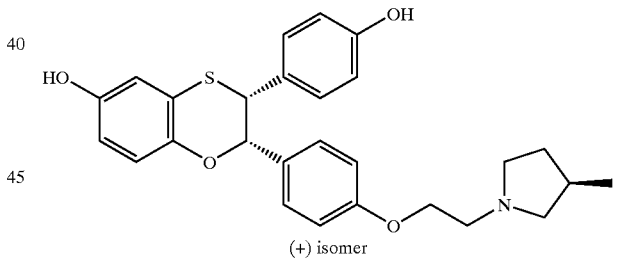

(+) isomer

25ab. Step A

The fast moving (+)-dihydrobenzoxathiin obtained from Example 22 was coupled with 2-[(3R)-3-methylpyrrolidin-1-yl]ethanol, synthesized in Example 36. After purification by silica gel chromatography with 5% MeOH/CH$_2$Cl$_2$, the desired adduct was obtained.

Step B and Step C

The adduct from Step A was debenzylated and desilylated to give the desired product, as a white solid, after purification by silica gel chromatography with 10% MeOH/CH$_2$Cl$_2$ as eluant. $^1$H NMR (500 MHz, methanol-d4) δ (ppm): 6.94 (d, 2H), 6.78 (d, 1H), 6.75 (d, 2H), 6.72 (d, 2H), 6.58 (d, 1H), 6.50 (d, 1H), 6.48 (d, 2H), 5.38 (d, J=1.8 Hz, 1H), 4.36 (d, J=1.9 Hz, 1H), 4.05 (t, 2H), 2.98 (t, 1H), 2.85 (m, 2H), 2.60 (q, 1H), 2.50 (m, 1H), 2.28 (m, 1H), 2.15 (t, 1H), 1.50(m, 2H), 1.05(d, 3H); MS m/z 465 (M$^+$+1); [α]$_D$=+274° (c=0.47, MeOH).

89

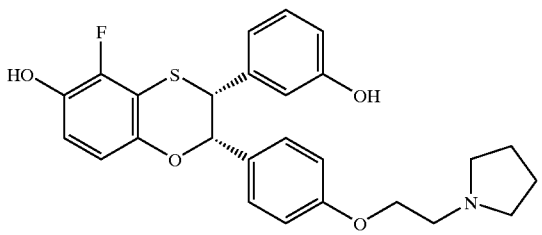

25ac. Step A:

Using the chiral material (0.1230 g, 0.27 mmol) generated in Example 24, and 1-(2-hydroxyethyl)pyrrolidine (0.094 mL, 0.80 mmol) the desired product was obtained as a pale yellow oil after purification by silica gel chromatography using 10% MeOH/CH$_2$Cl$_2$ as the eluant. $^1$H 500 MHz NMR(CDCl$_3$) ppm(δ): 1.83 (m, 4H), 2.64 (m, 4H), 2.90 (t, 2H), 3.39 (s, 3H), 3.59 (s, 3H), 4.08 (t, 2H), 4.38 (d, J=2.3 Hz, 1H), 4.99 (s, 2H), 5.19 (s, 2H), 5.45 (d, J=2.0 Hz, 1H), 6.57–7.09 (m, 10H).

Step B:

To a solution of the product (0.058 g, 0.10 mmol) obtained from Step A in MeOH (1 mL) was added 2N HCl (0.21 mL, 0.41 mmol) and the resulting solution was heated to 80° C. under N$_2$ for 45 min. The reaction was partitioned between EtOAc and ice/saturated NaHCO$_3$. The organic layer was collected, washed with brine, dried over Na$_2$SO$_4$, filtered, and concentrated in vacuo to give the desired product as a yellow foam.

$^1$H 500 MHz NMR(d$_6$-acetone) ppm(δ): 1.72 (m, 4H), 2.57 (m, 4H), 2.82 (t, 2H), 4.08 (t, 2H), 4.62 (d, J=2.3 Hz, 1 H), 5.47 (d, J=2.0 Hz, 1H), 6.41–7.10 (m, 10H); MS m/z 468 (M$^+$).

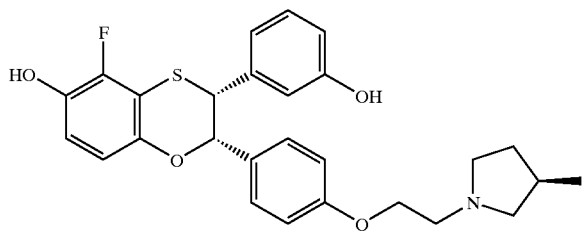

25ad. Step A:

Using the chiral material (0.6315 g, 1.4 mmol), generated in Example 24, and 2-[(3R)-3-methylpyrrolidin-1-yl]ethanol (0.5400 g, 4.1 mmol), generated in Example 36, the desired product was obtained as a pale yellow oil, after purification by silica gel chromatography using 5% MeOH/CH$_2$Cl$_2$ as the eluant. $^1$H 500 MHz NMR(CDCl$_3$) ppm(δ): 1.01 (d, 3H), 1.24 (m, 1 H), 2.02–2.09 (m, 2H), 2.25 (m, 1H), 2.52 (m, 1H), 2.77–2.94 (m, 4H), 3.34 (s, 3H), 3.54 (s, 3H), 4.09 (t, 2H), 4.34 (d, J=2.2 Hz, 1 H), 4.95 (s, 2H), 5.15 (s, 2H), 5.41 (d, J=1.9 Hz, 1H), 6.53–7.03 (m, 10H).

Step B:

Following the procedure detailed above (Step B), the material (0.6454 g, 1.1 mmol) obtained from Step A was deprotected with 2 N HCl (2.3 mL, 4.5 mmol) to give the desired product as a tan foam. $^1$H 600 MHz NMR(d$_6$-acetone) ppm(δ): 0.99 (d, 3H), 1.29 (m, 1 H), 1.96–2.84 (m, 8H), 4.03 (t, 2H), 4.59 (d, J=2.2 Hz, 1 H), 5.45 (d, J=1.9 Hz, 1H), 6.39–7.08 (m, 10H); MS m/z 482 (M$^+$); [α]$_D$=+271 (c=1.01; MeOH).

90

Example 26

Preparation of

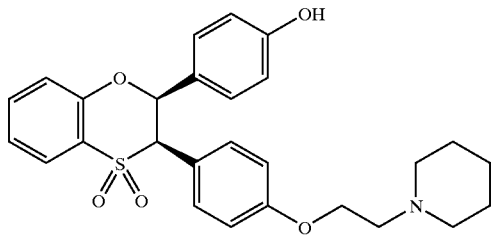

Step A

To a well stirred solution of the dihydrobenzoxathiin 25d (Step B) (30 mg, 0.061 mmol), prepared from Example 25, was added 5 equivalents of meta-chloroperbenzoic acid (m-CPBA) in methylene chloride at 0° C. The ice bath was removed and the reaction mixture was stirred at room temperature for three hours. The reaction mixture was quenched with a saturated solution of NaHSO$_3$ and stirred for additional 30 minutes. The aqueous layer was extracted with EtOAc and the organic layer was washed with brine, dried with MgSO$_4$, and evaporated to give a residue which was used in the next step without further purification. $^1$H NMR (400 MHz, CD$_3$OD) δ (ppm): 7.82 (dd, 1H), 7.67 (dt, 1H), 7.28 (m, 2H), 7.2 (d, 2H), 7.3 (d, 2H), 6.92 (d, 2H), 6.82 (d, 2H), 6.32 (d, 1H), 5.12 (s, 2H), 4.84 (d, 1H), 4.2 (br t, 2H), 3.40 (s, 3H), 3.2 (m, 2H), 3.0 (m, 4H), 1.75 (m, 4H), 1.6 (m, 2H).

Step B

The MOM protecting group was removed following the procedure outlined above. The desired product was isolated after purification by silica gel chromatography using 5% MeOH/CH$_2$Cl$_2$ as the eluant. $^1$H NMR (400 MHz, CD$_3$OD) δ (ppm): 7.82 (dd, 1H), 7.64 (dt, 1H), 7.26 (m, 2H), 7.04 (d, 2H), 6.06 (d, 2H), 6.76 (d, 2H), 6.65 (d, 2H), 6.24 (d, J=1.9 Hz, 1H), 4.71 (d, 1H), 4.1 (t, 2H), 2.72 (t, 2H), 2.5 (br s, 4H), 1.6 (m, 4H), 1.45 (m, 2H); MS m/z 481.1 (M$^+$+1).

Example 27

Preparation of

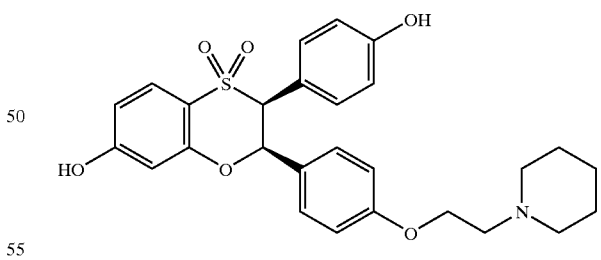

Step A

Utilizing the procedure from Example 26 (Step A), the dihydrobenzoxathiin 25a (20 mg, 0.028 mmol), obtained from Example 25 (Step A), was oxidized by m-CPBA at room temperature. The crude material was used in the next step without further purification. $^1$H NMR (400 MHz, CDCl$_3$) δ (ppm): 7.84 (d, 1H), 7.7–7.4 (m, 5H), 7.02 (d, 2H), 6.88 (dd, 1H), 6.82 (d, 2H), 6.76 (two d, 4H), 6.72 (d, 1H), 6.22 (d, J=2.2 Hz, 1H), 5.18 (q, 2H), 4.28 (d, J=2.1 Hz, 1H), 4.09 (t, 2H), 2.8 (t, 2H), 2.55 (br s, 4H), 1.63 (m, 4H), 1.48 (m, 2H), 1.22 (m, 3H), 1.1 (d, 18H).

Step B

The product from Step A was deblocked using the standard procedure described in Example 25 (Step B) to afford the debenzylated product, which was used without further purification.

Step C

The silyl protecting group was removed following the procedure outlined in Example 25 (Step C). The final product was isolated after purification by silica gel chromatography using 5% MeOH/CH$_2$Cl$_2$ as the eluant. $^1$H NMR (400 MHz, CD$_3$OD) δ (ppm): 7.62 (d, 1H), 7.14 (d, 2H), 6.84 (two d, 4H), 6.68 (dd, 1H), 6.6 (d, 2H), 6.55 (d, 1H), 6.22 (d, 1H), 4.55 (d, J=2.1 Hz, 1H), 4.1 (t, 2H), 2.8 (t, 2H), 2.6 (br s, 4H), 1.64 (M, 4H), 1.5 (M, 2H); MS m/z 496.1 (M$^+$+1).

Example 28

Preparation of

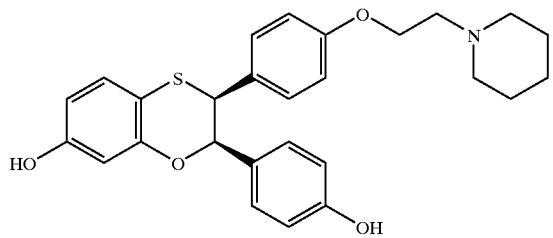

Step A

To a solution of dihydrobenzoxathiin 21e (100 mg, 0.167 mmol), generated from Example 21, in CH$_2$Cl$_2$ was added triethylamine (0.07 mL), a catalytic amount of N,N-dimethylaminopyridine (DMAP) and acetic anhydride (0.034 mL, 2 eq) at room temperature. The resultant mixture was stirred for 30 minutes and then poured into saturated NaHCO$_3$. The aqueous layer was extracted with CH$_2$Cl$_2$ and then dried over anhydrous Na$_2$SO$_4$. The solvent was evaporated to give an oil, which was subjected to silica gel chromatography with 10% EtOAc/hexane as eluant to give the product. $^1$H NMR (400 MHz, CDCl$_3$) δ (ppm): 7.48–7.34 (m, 5H), 7.08 (d, 1H), 6.99 (d, 2H), 6.94 (d, 2H), 6.76 (d, 2H), 6.72–6.67 (m, 4H), 5.56 (d, 1H), 5.06 (br q, 2H), 4.34 (d, 1H), 2.3 (d, 3H), 1.22 (m, 3H), 1.1 (d, 18 H).

Step B

The silyl protecting group was removed following the procedure outlined in Example 25 (Step C). The desired product was isolated after purification by silica gel chromatography using 5% MeOH/CH$_2$Cl$_2$ as the eluant. $^1$H NMR (400 MHz, CDCl$_3$) δ (ppm): 7.48–7.34 (m, 5H), 7.09 (d, 1H), 7.04 (d, 2H), 6.98 (d, 2H), 6.78 (d, 2H), 6.7 (m, 2H), 6.59 (d, 2H), 5.56 (d, 1H), 5.06 (br q, 2H), 4.74 (s, 1H), 4.36 (d, 1H), 2.2 (s, 3H).

Step C

The desilylated product (80 mg, 0.165 mmol) obtained from Step B was coupled with 1-piperidineethanol using the procedure described in Example 25 (Step A). After purification by silica gel chromatography with 3% MeOH/CH$_2$Cl$_2$, the desired adduct was obtained. $^1$H NMR (400 MHz, CDCl$_3$) δ (ppm): 7.48–7.34 (m, 5H), 7.08 (d, 1H), 7.04 (d, 2H), 6.98 (d, 2H), 6.82 (d, 2H), 6.7 (dd, 1H), 6.68 (d, 1H), 6.68 (d, 2H), 5.58 (d, J=2.2 Hz, 1H), 5.05 (br q, 2H), 4.36 (d, J=2.2 Hz, 1H), 4.05 (t, 2H), 2.68 (t, 2H), 2.5 (br s, 4H), 2.25 (s, 3H), 1.6 (m, 4H), 1.45 (m, 2H); MS m/z 597.3 (M$^+$+1.

Step D

To a solution of 10 mg (0.017 mmol) of the adduct, generated from Step C, in anhydrous THF was added four equivalents of a 1.0M Super-Hydride® solution (lithium triethylborohydride in THF). The resulting mixture was stirred for 2 hours at 0° C. and then allowed to warm to room temperature (30 minutes). The reaction mixture was hydrolyzed with H$_2$O/NaHCO$_3$. The aqueous layer was extracted with EtOAc, the organic layer separated, dried, and evaporated to give an oil, which was used in the next step without further purification.

Step E

The crude product from Step D was deblocked using the standard procedure described in Example 25 (Step B) to afford the final product, after purification by silica gel chromatography using 5% MeOH/CH$_2$Cl$_2$ as the eluant. $^1$H NMR (400 MHz, CD$_3$OD) δ (ppm): 6.92 (d, 1H), 6.83 (d, 2H), 6.82 (d, 2H), 6.65 (d, 2H), 6.58 (d, 2H), 6.46 (dd, 1H), 6.42 (d, 1H), 5.44 (d, J=2.1 Hz, 1H), 4.38 (d, 1H, J=2.3 Hz, 1), 4.04 (t, 2H), 2.78 (t, 2H), 2.6 (br s, 4H), 1.6 (m, 4H), 1.5 (m, 2H); MS m/z 465 (M$^+$+1).

Example 29

Preparation of CIS-3-Substituted Dihydrobenzoxathiins

Preparation of

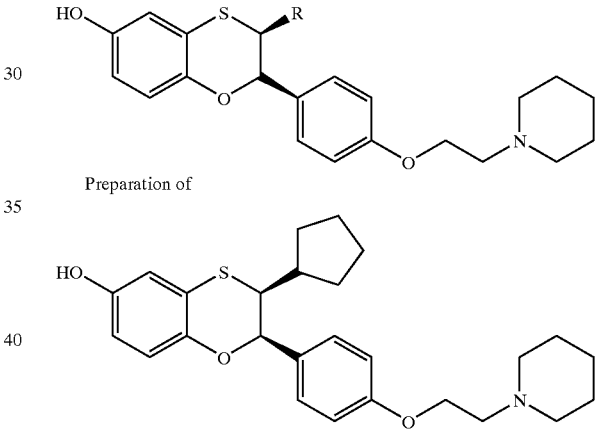

Preparation of

29a. Step A: Reductive Cyclization

To a stirred solution of 102.2 mg (0.17 mmol) of the cyclopentyl-thioketone 20ac, generated in Example 20, in 1 mL of dichloromethane at −23° C. under an N$_2$ atmosphere was added 68 μL (0.087 mmol) of neat trifluoroacetic acid (TFA). To the stirred reaction mixture at −23° C. was slowly added 41.4 μL (0.259 mmol) of neat triethylsilane and the resulting mixture was stirred further for three hours. The reaction mixture was partitioned between ethyl acetate/saturated NaHCO$_3$/ice/brine, and the organic phase was separated, washed with brine, dried over anhydrous sodium sulfate, filtered, and evaporated. The residue was purified by silica gel chromatography using methylene chloride/hexanes (1:1) as eluant to provide the cis-cyclopentyl-dihydrobenzoxathiin derivative. $^1$H 500 MHz NMR(CDCl$_3$) ppm(δ):1.12 (d, 18H), 1.26–2.12 (m, 12H), 2.5 (m, 1H), 4.24 (d, 1H), 4.9 (m, 2H), 6.8–7.69 (m, 12H).

Step B: Desilylation

To a stirred solution of 89.6 mg (0.156 mmol) of the cis-cyclopentyl derivative prepared in Step A above in 1 mL of THF at 0° C. was added sequentially 13.3 μL (0.234 mmol) of acetic acid and then 171 μL (0.171 mmol) of a 1M solution of tetrabutylammonium fluoride in THF. The mixture was stirred at 0° C. for 0.5 hour and then partitioned between ethyl acetate/2N HCl/ice/brine, and the organic phase was separated, washed with brine, dried over anhydrous sodium sulfate, filtered, and evaporated. The residue was purified by silica gel chromatography using methylene chloride-ethyl acetate (50:1) as eluant to provide the phenolic derivative. $^1$H 500 MHz NMR(CDCl$_3$) ppm(δ):1.32–1.94 (m, 9H), 3.51 (dd, J=5.5, 2.5 Hz, 1H), 5.03 (s, 2H), 5.42 (d, J=2.3 Hz, 1H), 6.67–7.47 (m, 12H).

Step C: Mitsunobu Reaction

To a stirred solution of a mixture of 56.3 mg (0.135 mmol) of the cis-cyclopentyl derivative prepared in Step B above, 53.6 μL (0.404 mmol) of 1-piperidineethanol, and 123.5 mg (0.47 mmol) of triphenylphosphine in 1 mL of anhydrous THF at 0° C. was added 87.4 μL (0.444 mmol) of neat diisopropylazodicarboxylate (DIAD). The ice-water bath was removed and the mixture was stirred further for six hours. The mixture was partitioned between ethyl acetate/2N HCl/ice/brine, and the organic phase was separated, washed with brine, dried over anhydrous sodium sulfate, filtered, and evaporated. The residue was purified by silica gel chromatography using ethyl acetate-methanol (9:1) as eluant to provide the adduct. $^1$H 500 MHz NMR(CDCl$_3$) ppm(δ):1.33–2.0 (m, 1SH), 2.56 (m, 4H), 2.82 (t, J=6 Hz, 2H), 3.51 (dd, J=5.4, 2.4 Hz, 1H), 4.16 (t, J=6 Hz, 2H), 5.02 (s, 2H), 5.42 (d, J=2.3 Hz, 1H), 6.66–7.46 (m, 12H).

Step D: Debenzylation:

A stirred mixture of 36.6 mg (0.0069 mmol) of the cis-cyclopentyl derivative prepared in Step C above, 14.7 mg (0.014 mmol) of palladium black, and 87.1 mg (0.138 mmol) of ammonium formate in 2 mL of ethanol-ethyl acetate-water (7:2:1) was heated at 80° C. for two hours. The mixture was filtered through celite, washed well with ethyl acetate and the filtrate was partitioned between ethyl acetate/saturated sodium bicarbonate/brine, and the organic phase was separated, washed with brine, dried over anhydrous sodium sulfate, filtered, and evaporated. The residue was purified by silica gel chromatography using ethyl acetate-methanol (9:1) as eluant to provide the final product. $^1$H 500 MHz NMR(CDCl$_3$) ppm(δ):1.33–2.0 (m, 15H), 2.6 (m, 4H), 2.88 (m, 2H), 3.48 (t, J=2.3 Hz, 1H), 4.18 (m, 2H), 5.38 (d, J=2.3 Hz, 1H), 6.5 (m, 1H), 6.63 (d, 2.9 Hz, 1H) 6.74 (d, J=8.7 Hz, 1H), 6.89 (d, J=8.7 Hz, 2H), and 7.34 (d, J=8.7 Hz, 2H).

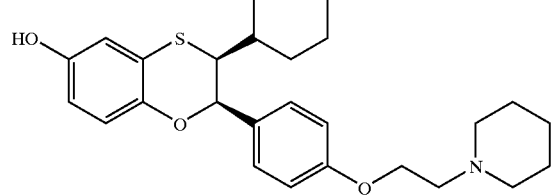

29b. Step A

Starting with the cyclohexyl derivative 20ab, prepared in Example 20, the corresponding cis-cyclohexyl-benzoxathiin was prepared after purification by silica gel chromatography using methylene chloride-hexanes (1:1). $^1$H 500 MHz NMR (CDCl$_3$) ppm(δ): 1.14 (d, 18H), 1.11–1.9 (m, 14H), 3.2 (t, 1H), 5.03 (s, 2H), 5.44 (d, J=2.5 Hz, 1H), 6.66–7.47 (m, 12H).

Step B:

Starting with the cyclohexyl derivative prepared in the previous step, the corresponding cis-cyclohexyl-benzoxathiin phenol was prepared. $^1$H 500 MHz NMR (CDCl$_3$) ppm(δ):1.11–1.93 (m, 11H), 3.23 (t, J=3 Hz, 1H), 5.03 (s, 2H), 5.44 (d, J=2.3 Hz, 1H), 6.66–7.47 (m, 12H).

Step C:

Starting with the cyclohexyl derivative prepared in the previous step the corresponding cis-cyclohexyl-benzoxathiin adduct was prepared. $^1$H 500 MHz NMR (CDCl$_3$) ppm(δ):1.11–1.93 (m, 17H), 2.6 (m, 4H), 2.87 (m, 2H), 3.2 (d, J=2.5 Hz, 1H), 4.2 (m, 2H), 5.02 (s, 2H), 5.44 (d, J=2.1 Hz, 1H), 6.65–7.46 (m, 12H).

Step D:

Starting with the cyclohexyl derivative prepared in the previous step, the final product was prepared. $^1$H 500 MHz NMR(CDCl$_3$) ppm(δ):1.00–1.90 (m, 18H), 2.6 (m, 4H), 2.81 (t, 2H), 3.19 (t, J=3.0 Hz,1H), 4.18 (m, 2H), 5.38 (d, J=2.3 Hz, 1H), 6.43 (m, 1H), 6.62 (d, J=3.0 Hz, 1H), 6.68 (d, J=8.7 Hz, 1H), 6.87 (d, J=8.7 Hz, 2 H), and 7.34 (d, J=8.7 Hz, 2H); MS m/z 454 (M$^+$).

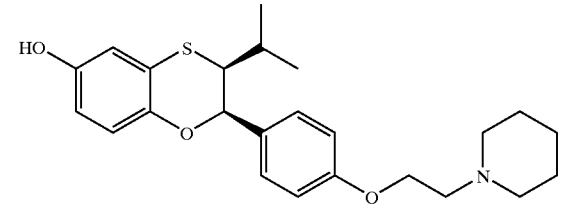

29c. Step A:

Starting with the isopropyl adduct 20af (0.0208 g, 0.049 mmol), prepared in Example 20, the crude product was isolated after stirring at −23° C. for 6 h 20 min. Purification by silica gel chromatography with 30% EtOAc/hexane as the eluant afforded the desired product as a yellow oil. $^1$H 500 MHz NMR(CDCl$_3$) ppm(□): 0.95 (d, 3H), 0.98 (d, 3H), 1.95 (m, 1H), 3.30 (t, J=3 Hz, 1H), 5.03 (s, 2H), 5.42 (d, J=2.6 Hz, 1H), 6.66–7.47 (m, 12H).

Step B:

The dihydrobenzoxathiin prepared in Step A above was coupled with 1-piperidineethanol with the exception that the reaction was allowed to slowly warm from 0° C. to ambient temperature over 3.5 h. Purification by silica gel chromatography with 10% MeOH/CH$_2$Cl$_2$ as the eluant afforded the desired product as a pale yellow oil. $^1$H 500 MHz NMR (CDCl$_3$) ppm(δ): 0.95 (d, 3H), 0.98 (d, 3H), 1.50–1.68 (m, 6H), 1.95 (m, 1H), 2.60 (m, 4H), 2.86 (t, 2H), 3.30 (t, J=3 Hz, 1H), 4.20 (t, 2H), 5.03 (s, 2H), 5.42 (d, J=2.6 Hz, 1H), 6.66–7.49 (m, 12H).

Step C:

Starting with the compound prepared in Step B above, the corresponding cis-isopropyl-benzoxathiin adduct was prepared after silica gel chromatography with 10% MeOH/CH$_2$Cl$_2$ as the eluant. $^1$H 500 MHz NMR(CDCl$_3$) ppm(δ): 0.95 (d, 3H), 0.98 (d, 3H), 1.50–1.68 (m, 6H), 1.95 (m, 1H), 2.60 (m, 4H), 2.86 (t, 2H), 3.26 (t, J=3.0 Hz, 1H), 4.20 (t, 2H), 5.37 (d, J=2.5 Hz, 1H), 6.47 (dd, 1H), 6.65 (d, J=3 Hz, 1H), 6.72 (d, J=8.6 Hz, 2H), and 7.35 (d, J=8.7 Hz, 2H); MS m/z 414 (M$^+$).

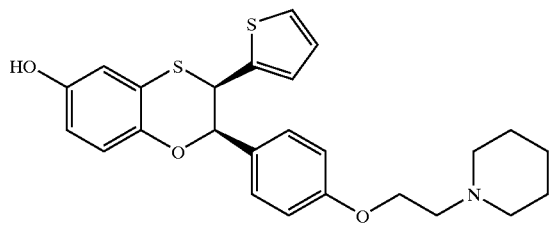
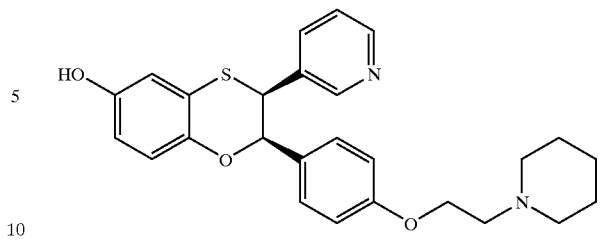

29d. Step A:

Starting with the 2-thiophene adduct 20ag (0.0208 g, 0.049 mmol), prepared in Example 20, and slightly modifying the procedure, the crude product was isolated after stirring at 0° C. to ambient temperature for 1 h 40 min. Purification by silica gel chromatography with 30% EtOAc/hexane as the eluant afforded the desired product as a red oil. $^1$H 500 MHz NMR(CDCl$_3$) ppm($\delta$): 1.11 (d, 18H), 1.24 (m, 3H), 4.67 (d, J=2.0 Hz, 1H), 5.50 (d, J=1.8 Hz, 1H), 6.60–7.12 (m, 10H).

Step B: Protection with MOM

To a solution of the dihydrobenzoxathiin (0.0629 g, 0.13 mmol) prepared in Step A above in distilled THF (1 mL) was added 60% NaH in mineral oil (0.0090 g, 0.19 mmol) at 0° C. under N$_2$. After the gas evolution had ceased, MOMCl (0.013 mL, 0.16 mmol) was added dropwise to the reaction. After 30 min., another 1.3 equivalents of MOMCl was added to the reaction. Within 5 min., the reaction was complete by TLC. The resulting dark red solution was partitioned between EtOAc and ice/H$_2$O. The organic layer was washed with brine, dried over Na$_2$SO$_4$, and concentrated in vacuo. The desired product was used in the next reaction without purification. $^1$H 500 MHz NMR(CDCl$_3$) ppm($\delta$): 1.11 (d, 18H), 1.24 (m, 3H), 3.52 (s, 3H), 4.67 (d, J=2.1 Hz, 1H), 5.14 (m, 2H), 5.50 (d, J=1.8 Hz, 1H), 6.60–7.12 (m, 10H).

Step C: Desilylation

The dihydrobenzoxathiin prepared in Step B above was desilylated to afford the desired product as a colorless oil after silica gel chromatography with 30% EtOAc/hexane as the eluant. $^1$H 500 MHz NMR(CDCl$_3$) ppm($\delta$): 3.52 (s, 3H), 4.69 (d, J=1.8 Hz, 1H), 5.15 (m, 2H), 5.51 (d, J=1.8 Hz, 1H), 6.60–7.15 (m, 10H).

Step D: Mitsunobu Reaction

The material prepared in the previous step was converted to the desired product following the procedure detailed, with the exception that the reaction was allowed to warm from 0° C. to ambient temperature over 4 h. The product was purified by silica gel chromatography (one elution with 30% EtOAc/hexane followed by a second elution with 10% MeOH/CH$_2$Cl$_2$). $^1$H 500 MHz NMR(CDCl$_3$) ppm($\delta$): 1.40–2.60 (m, 10H), 2.79 (t, 2H), 3.52 (s, 3H), 4.10 (t, 2H), 4.69 (d, J=1.8 Hz, 1H), 5.15 (m, 2H), 5.51 (d, J=1.8 Hz, 1H), 6.60–7.15 (m, 10H).

Step E: Deprotection of MOM

A mixture of the material (0.0401 g, 0.080 mmol) prepared in Step D above and 2 N HCl (0.20 mL, 0.40 mmol) in MeOH (1.0 mL) was heated to 60° C. under N$_2$ for 2.5 h. The reaction was partitioned between EtOAc and ice/sat. NaHCO$_3$. The organic layer was washed with brine, dried over Na$_2$SO$_4$, and concentrated in vacuo. The residue was triturated with Et$_2$O and desired product was obtained as a white solid. $^1$H 500 MHz NMR(d$_6$-acetone+CD$_3$OD) ppm ($\delta$): 1.50–3.19 (m, 10H), 3.23 (t, 2H), 4.30 (t, 2H), 5.00 (d, J=1.8 Hz, 1H), 5.51 (d, J=1.8 Hz, 1H), 6.57–7.25 (m, 10H); MS m/z 454 (M$^+$)

29e. Step A: Reductive Cyclization 0.0792 g of the 3-pyridyl derivative 20ae, prepared in Example 20, was converted to its corresponding benzoxathiin after stirring at ambient temperature for 5 h. The desired product was isolated from the reaction mixture after silica gel chromatography using 30% EtOAc/hexane as the eluant. $^1$H 500 MHz NMR(CDCl$_3$) ppm($\delta$): 1.11 (d, 18H), 1.24 (m, 3H), 4.36 (d, J=2.1 Hz, 1H), 5.05 (s, 2H), 5.50 (d, J=1.6 Hz, 1H), 6.77–8.43 (m, 16H).

Step B: Desilylation

The dihydrobenzoxathiin generated in Step A above was desilylated to afford the desired product after silica gel chromatography (one elution with 50% EtOAc/hexane followed by a second elution with 30% EtOAc/hexane). $^1$H 500 MHz NMR(CDCl$_3$) ppm($\delta$): 4.42 (d, J=2.1 Hz, 1H), 5.07 (s, 2H), 5.50 (d, J=1.6 Hz, 1H), 6.77–8.43 (m, 16H).

Step C: Mitsunobu Reaction

The material prepared in the previous step was converted to the desired product, with the exception that the reaction was allowed to warm from 0° C. to ambient temperature over 4 h. Purification was accomplished by silica gel chromatography using 10% MeOH/CH$_2$Cl$_2$ as the eluant. $^1$H 500 MHz NMR(CDCl$_3$) ppm($\delta$): 1.40–2.60 (m, 10H), 2.80 (t, 2H), 4.10 (t, 2H), 4.38 (d, J=1.8 Hz, 1H), 5.07 (s, 2H), 5.50 (d, J=1.8 Hz, 1H), 6.77–8.43 (m, 16H).

Step D: Debenzylation

Starting with the material prepared in Step C above, the corresponding cis-3-pyridyl-dihydrobenzoxathiin adduct was prepared after silica gel chromatography with 10% MeOH/CH$_2$Cl$_2$ as the eluant. $^1$H 500 MHz NMR(CDCl$_3$) ppm($\delta$):1.40–2.60 (m, 10H), 2.80 (t, 2H), 4.10 (t, 2H), 4.36 (d, J=2.1 Hz, 1H), 5.45 (d, J=1.9 Hz, 1H), 6.59–8.8.43 (m, 11H); MS m/z 449 (M$^+$).

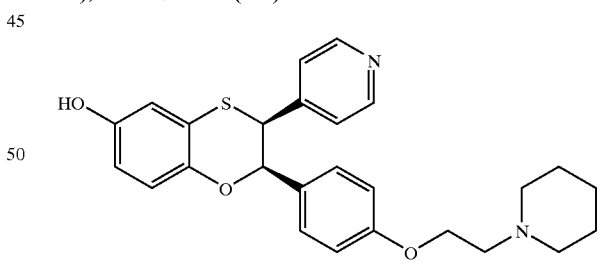

29f. Step A: Reductive Cyclization 0.1871 g of the 4-pyridyl derivative 20ad, prepared in Example 20, was converted to its corresponding dihydrobenzoxathiin after stirring at ambient temperature for 30 h. The desired product was isolated from the reaction mixture after silica gel chromatography using 30% EtOAc/hexane as the eluant. $^1$H 500 MHz NMR(CDCl$_3$) ppm($\delta$):1.11 (d, 18H), 1.24 (m, 3H), 4.32 (d, 1H), 5.08 (s, 2H), 5.50 (d, 1H), 6.60–8.39 (m, 16H).

Step B: Desilylation

The dihydrobenzoxathiin generated in Step A above was desilylated to afford the desired product after silica gel chromatography (one elution with 50% EtOAc/hexane followed by a second elution with 30% EtOAc/hexane). ¹H 500 MHz NMR(CDCl₃) ppm(δ): 4.33 (d, 1H), 5.07 (s, 2H), 5.46 (d, 1H), 6.63–8.37 (m, 16H).

Step C: Mitsunobu Reaction

The material prepared in the previous step was converted to the desired product, with the exception that the reaction was allowed to warm from 0° C. to ambient temperature over 5 h. Purification was accomplished by silica gel chromatography (one elution with 10% MeOH/CH₂Cl₂ followed by a second elution with 20% EtOAc/CH₂Cl₂). ¹H 500 MHz NMR(CDCl₃) ppm(δ):1.40–2.60 (m, 10H), 2.80 (t, 2H), 4.14 (t, 2H), 4.32 (d, J=3.0 Hz, 1H), 5.06 (s, 2H), 5.49 (d, J=2.1 Hz, 1H), 6.79–8.38 (m, 16H).

Step D: Debenzylation

Starting with the material prepared in Step C above, the desired product was obtained as a 4:1 cis/trans mixture after silica gel chromatography (one elution with 30% EtOAc/hexane followed by a second elution with 10% MeOH/CH₂Cl₂). Cis isomer: ¹H 500 MHz NMR(CDCl₃) ppm(δ) :1.40–2.70 (m, 10H), 2.80 (t, 2H), 4.10 (t, 2H), 4.30 (d, J=2.0 Hz, 1H), 5.44 (d, J=1.8 Hz, 1H), 6.59–8.40 (m, 11H). Trans isomer: ¹H 500 MHz NMR(CDCl₃) ppm(δ): 1.40–2.70 (m, 10H), 2.80 (t, 2H), 4.15 (t, 2H), 4.38 (d, J=8.7 Hz, 1H), 4.92 (d, J=8.7 Hz, 1H), 6.59–8.46 (m, 11H); MS m/z 449 (M⁺).

Example 30

Preparation of Trans-3-Substituted Dihydrobenzoxathiins

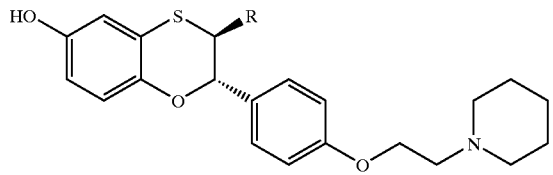

Preparation of

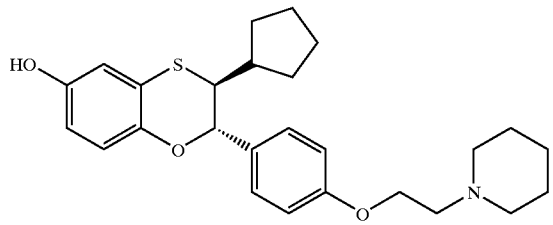

30a. Step A: Reduction

To a stirred solution of 265.1 mg (0.449 mmol) of the cyclopentyl-thioketone 20ac, generated in Example 20, in 3 mL of methanol-dichloromethane (1:1) at 0° C. to room temperature was added portion-wise sufficient sodium borohydride to complete the reduction. The reaction mixture was partitioned between ethyl acetate/2N HCl/ice/brine, and the organic phase was separated, washed with brine, dried over anhydrous sodium sulfate, filtered, and evaporated to provide crude cyclopentyl-thio-carbinols, which was used without further purification in the next step.

Step B: Cyclization

A mixture of 266 mg (0.449 mmol) of the crude product, prepared in Step A above, and 89 mg of amberlyst 15 in 3 mL of toluene was stirred at ambient temperature for two hours. The resin was removed by filtration and washed well with ethyl acetate. The filtrate was evaporated and the residue obtained was purified by silica gel chromatography using dichloromethane-hexanes(1:1) as eluant to provide the trans-dihydro-benzoxathiin derivative. ¹H 500 MHz NMR (CDCl₃) ppm(δ):1.13 (d, 18H), 1.26–1.94 (m, 12H), 3.64 (dd, J=7.8 Hz, 5.5 Hz, 1H), 4.78 (d, J=7.8 Hz, 1H), 5.02 (s, 2H), 6.6–7.45 (m, 12H).

Step C: Desilylation

Following the procedure outlined in Step B of Example 29, 228.5 mg (0.397 mmol) of material prepared in the previous step was desilylated to give the corresponding phenol.

Step D: Mitsunobu reaction

Following the procedure detailed in Step C of Example 29, the material prepared in the previous step was converted to the corresponding trans-cyclopentyl-dihydrobenzoxathiin adduct. ¹H 500 MHz NMR(CDCl₃) ppm(δ):1.39–2.0 (m, 15H), 2.6 (m, 4H), 2.88 (m, 2H), 3.66 (dd, J=7.8 Hz, 5.5 Hz, 1H), 4.21 (m, 2H), 4.81 (t, J=7.8 Hz, 2H), 5.01 (s, 2H), 6.64–7.49 (m, 12H).

Step E: Debenzylation

Following the procedure detailed in Step D of Example 29, the material prepared in the previous step was converted to the corresponding trans-cyclopentyl-dihydrobenzoxathiin product. ¹H 500 MHz NMR(CDCl₃) ppm(δ):1.29–2.0 (m, 15H), 2.6 (m, 4H), 2.88 (m, 2H), 3.67 (dd, J=8 Hz, 5 Hz, 1H), 4.18 (m, 2H), 4.77 (t, J=8 Hz, 2H), 6.5 (dd. J=2.7 Hz, 8.7 Hz, 1H), 6.65 (d, 2.7 Hz, 1H) 6.77 (d, J=8.7 Hz, 1H), 6.88 (d, J=7.5 Hz, 2H), and 7.27 (d, J=7.5 Hz, 2H).

Utilizing the above series of experimental procedures, the following compounds were prepared:

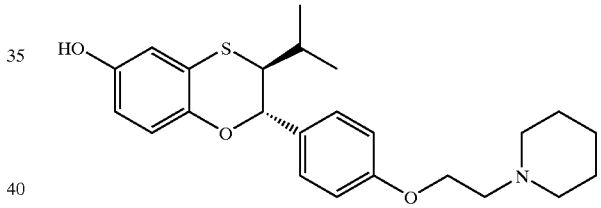

30b. Step A: Silylation

To a stirred solution of the isopropyl-thioketone 20af (0.0395 g, 0.097 mmol), generated in Example 20, in distilled THF (1 mL) at 0° C. was added 60% NaH in mineral oil (0.0183 g, 0.20 mmol) followed by TIPSCl (0.048 mL, 0.22 mmol). After 35 min., another equivalent of TIPSCl was added to drive the reaction to completion. The reaction was partitioned between EtOAc and ice/H₂O, and the organic layer was washed with brine, dried over Na₂SO₄, and concentrated in vacuo to afford the desired product. The crude material was used in the next step without further purification.

Step B: Reduction

To a solution of the crude product (0.097 mmol) prepared in Step A above in distilled THF (1 mL) was added a 1 M solution of Super-Hydride® solution (lithium triethylborohydride in tetrahydrofuran), (0.15 mL, 0.15 mmol) at 0° C. under N₂. The reaction mixture was stirred for 20 min. before partitioning between EtOAc and ice/H₂O. The organic layer was further washed with brine, dried over Na₂SO₄, and concentrated in vacuo to give the desired product. The crude material was used in the next step without further purification. ¹H 500 MHz NMR(CDCl₃) ppm(δ): 0.90–1.40 (m, 49H), 1.69 (m, 1H), 3.10 (dd, 1H), 4.60 (d, 1H), 5.05 (s, 2 H), 6.70–7.50 (m, 12H).

Step C: Desilylation

To a solution of the material (0.097 mmol) prepared in the previous step in distilled THF (1 mL) was added AcOH (0.018 mL, 0.32 mmol) at 0° C. under $N_2$ followed by the addition of a 1 M solution of TBAF in THF (0.29 mL, 0.29 mmol). After 15 min., the reaction was partitioned between EtOAc and ice/sat. $NaHCO_3$. The organic layer was washed with brine, dried over $Na_2SO_4$, and concentrated in vacuo. Purification by silica gel chromatography using 40% EtOAc/hexane as the eluant afforded the desired product as a yellow foam. $^1H$ 500 MHz $NMR(CDCl_3)$ ppm(δ): 0.92 (d, 3H), 0.98 (d, 3H), 1.59 (m, 1H), 2.86 (dd, 1H), 4.62 (d, 1H), 5.02 (q, 2 H), 6.77–7.45 (m, 12H).

Step D: Cyclization

The material (0.0366 g, 0.089 mmol) generated in the previous step was converted to its corresponding trans-dihydrobenzoxathiin after stirring for 5 h 15 min. at ambient temperature. Purification by silica gel chromatography using 30% EtOAc/hexane as the eluant afforded the desired product as a white solid. $^1H$ 500 MHz $NMR(CDCl_3)$ ppm(δ): 0.98 (d, 3H), 1.03 (d, 3H), 1.78 (m, 1H), 3.57 (dd, J=3.7 Hz, J=8.5 Hz, 1H), 4.82 (d, J=8.4 Hz, 1H), 5.02 (s, 2 H), 6.63–7.46 (m, 12H).

Step E: Mitsunobu Reaction

The material (0.0266 g, 0.068 mmol) generated in the previous step was converted to its corresponding trans-isopropyl-dihydrobenzoxathiin adduct after warming from 0° C. to ambient temperature over 4 h 20 min. Purification by silica gel chromatography (one elution with 10% MeOH/$CH_2Cl_2$ followed by a second elution with 30% EtOAc/hexane) afforded the desired product as a white solid. $^1H$ 500 MHz $NMR(CDCl_3)$ ppm(δ): 0.98 (d, 3H), 1.02 (d, 3H), 1.29–1.67 (m, 6H), 1.78 (m, 1H) 2.58 (m, 4H), 2.85 (t, 2H), 3.57 (dd, J=3.7 Hz, J=8.5 Hz, 1H), 4.18 (t, 2H), 4.83 (d, J=8.4 Hz, 1H), 5.02 (s, 2 H), 6.63–7.46 (m, 12H).

Step F: Debenzylation

The material (0.0395 g, 0.068 mmol) generated in the previous step was converted to its corresponding trans-isopropyl-dihydrobenzoxathiin product. Purification was accomplished by silica gel chromatography using 10% MeOH/$CH_2Cl_2$ as the eluant. $^1H$ 500 MHz $NMR(CDCl_3)$ ppm(δ): 0.98 (d, 3H), 1.02 (d, 3H), 1.29–1.67 (m, 6H), 1.78 (m, 1H), 2.58 (m, 4H), 2.85 (t, 2H), 3.57 (dd, J=3.7 Hz, J=8.5 Hz, 1H), 4.18 (t, 2H), 4.83 (d, J=8.4 Hz, 1H), 6.48–7.29 (m, 7H); MS m/z 414 ($M^+$).

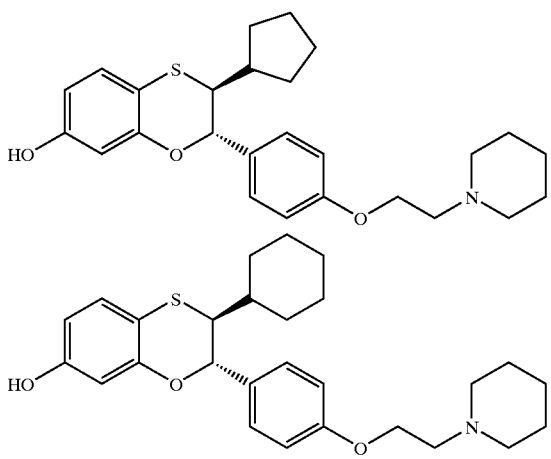

30c and 30d. Steps A and B: Reduction and Cyclization

Utilizing the thioketones 20y and 20z respectively, prepared in Example 20, and employing the procedures outlined above in Step A and B, the following compounds were prepared:

Trans-cyclopentyl derivative: $^1H$ 500 MHz $NMR(CDCl_3)$ ppm(δ):1.14 (d, 18H), 1.28–1.9 (m, 12H), 4.53 (m, 1H), 4.93 (d,1H), 5.01 (s, 2H), 6.6–7.43 (m, 12H).

Trans-cyclohexyl derivative: $^1H$ 500 MHz $NMR(CDCl_3)$ ppm(δ): 1.14 (d, 18H), 0.98–1.8 (m, 14H), 3.37 (dd, J=2.5 Hz, 8.1 Hz, 1H), 5.01 (s, 2H), 5.05 (d, J=8.1 Hz, 1H), 6.6–7.44 (m, 12H).

Step C: Desilylation

Utilizing the trans-dihydrobenzoxathiiins prepared in the previous step and employing the procedure outlined above in Step B of Example 29, the following compounds were prepared:

Trans-cyclohexyl phenol: $^1H$ 500 MHz $NM(CDCl_3)$ ppm (δ): 1.0–1.8 (m, 11H), 3.3 (m, 1H), 5.05 (s, 2H), 5.1 (d, 1H), 6.6–7.44 (m, 12H).

Trans-cyclopentyl phenol: $^1H$ 500 MHz $NMR(CDCl_3)$ ppm(δ):1.29–2.0 (m, 9H), 3.55 (dd, J=5.7 Hz, 7.6 Hz, 1H), 4.95 (d, J=7.6 Hz, 1H), 5.02 (s, 2H), 6.6–7.45 (m, 12H), Step D: Mitsunobu Reaction:

Utilizing the trans-dihydrobenzoxathiin phenols prepared in the previous step and employing the procedure outlined above in Step C of Example 29, the following compounds were prepared:

Trans-cyclohexyl adduct: $^1H$ 500 MHz $NMR(CDCl_3)$ ppm(δ):1.0–1.8 (m, 17H), 2.58 (m, 4H), 2.84 (m, 2H), 3.37 (m, 1H), 4.17 (t, J=6 Hz, 2H), 5.0 (s, 2H), 5.08 (d, J=7.8 Hz, 1H), 6.6–7.43 (m, 12H).

Trans-cyclopentyl adduct: $^1H$ 500 MHz $NMR(CDCl_3)$ ppm(δ):1.29–2.0 (m, 15H), 2.58 (m, 4H), 2.84 (m, 2H), 3.55 (m, 1H), 4.17 (m, 2H), 4.94 (d, J=7.3 Hz, 1H), 5.0 (s, 2H), 6.6–7.72 (m, 12H).

Step E: Debenzylation:

Utilizing the trans-dihydrobenzoxathiin adducts prepared in the previous step and employing the procedure outlined above in Step D of Example 29, the following compounds were prepared:

Trans-cyclohexyl adduct: $^1H$ 500 MHz $NMR(CDCl_3)$ ppm(δ):1.0–1.8 (m, 17H), 2.58 (m, 4H), 2.86 (m, 2H), 3.33 (m, 1H), 4.16 (m, 2H), 5.08 (d, J=7.8 Hz, 1H), 6.4–7.23 (m, 7H).

Trans-cyclopentyl adduct: $^1H$ 500 MHz $NMR(CDCl_3)$ ppm(δ):1.29–2.0 (m, 15H), 2.68 (m, 4H), 2.94 (m, 2H), 3.51 (m, 1H), 4.2 (m, 2H), 4.95 (d, J=7.4 Hz, 1H), 6.45–7.31 (m, 7H).

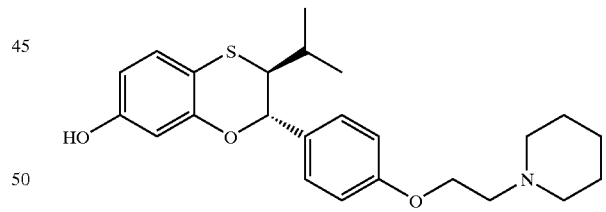

30e. Step A: Silylation

The isopropyl-thioketone 20aa (0.6314 g, 1.5 mmol), generated in Example 20, was silylated as described above. Purification by silica gel chromatography using 30% EtOAc/hexane as the eluant afforded the desired product as a yellow oil. $^1H$ 500 MHz $NMR(CDCl_3)$ ppm(δ): 0.98–1.30 (m, 49H), 2.35 (m, 1H), 4.38 (d, 1H), 4.99 (q, 2H), 6.33–7.79 (m, 12H).

Step B: Reduction

The material (0.8009 g, 1.1 mmol) isolated in Step A above was reduced to its corresponding alcohol and used without further purification in the next step. $^1H$ 500 MHz $NMR(CDCl_3)$ ppm(δ): 0.98–1.30 (m, 49H), 1.90 (m, 1H), 2.92 (dd, 1H), 4.59 (d, 1H), 5.05 (q, 2 H), 6.47–7.43 (m, 12H).

Step C: Desilylation

The material (0.022 mmol) isolated in Step B above was deprotected to afford the desired product which was used in the next step without purification.

Step D: Cyclization

The material generated in the previous step was converted to its corresponding trans-dihydrobenzoxathiin after stirring for 22 h at ambient temperature. Purification by silica gel chromatography using 30% EtOAc/hexane as the eluant afforded the desired product as a colorless oil. $^1$H 500 MHz NMR(CDCl$_3$) ppm(δ): 0.98 (d, 3H), 1.03 (d, 3H), 1.79 (m, 1H), 3.45 (dd, 1H), 4.98 (d, 1H), 5.02 (s, 2 H), 6.59–7.46 (m, 12H), MS m/z 393 (M$^+$).

Step E: Mitsunobu Reaction

The material (0.008 g, 0.020 mmol) generated in the previous step was converted to its corresponding trans-isopropyl-dihydrobenzoxathiin adduct after warming from 0° C. to ambient temperature over 6 h. Purification by silica gel chromatography using 10% MeOH/CH$_2$Cl$_2$ as the eluant afforded the desired product as a pale yellow oil. $^1$H 500 MHz NMR(CDCl$_3$) ppm(δ): 0.98 (d, 3H), 1.02 (d, 3H), 1.29–1.67 (m, 6H), 1.79 (m, 1H), 2.58 (m, 4H), 2.81 (t, 2H), 3.50 (dd, J=3.8 Hz, J=8.3 Hz, 1H), 4.18 (t, 2H), 4.97 (d, J=8.2 Hz, 1H), 5.01 (s, 2 H), 6.59–7.46 (m, 12H).

Step F: Debenzylation

The material (0.0085 g, 0.017 mmol) generated in the previous step was converted to its corresponding trans-isopropyl-dihydrobenzoxathiin product. Purification was accomplished by silica gel chromatography using 10% MeOH/CH$_2$Cl$_2$ as the eluant. $^1$H 500 MHz NMR(CDCl$_3$) ppm (δ): 0.98 (d, 3H), 1.02 (d, 3H), 1.49–1.70 (m, 6H), 1.75 (m, 1H), 2.61 (m, 4H), 2.85 (t, 2H), 3.41 (dd, J=3.8 Hz, J=8.3 Hz, 1H), 4.18 (t, 2H), 4.96 (d, J=8.2 Hz, 1H), 6.43–7.26 (m, 7H); MS m/z 414 (M$^+$).

Example 31

Preparation of Dihydro-Benzodithiins

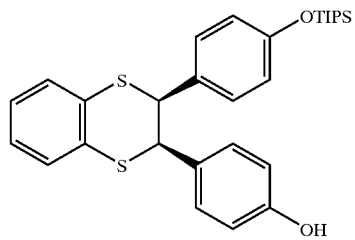

A

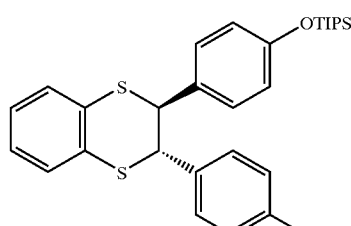

B

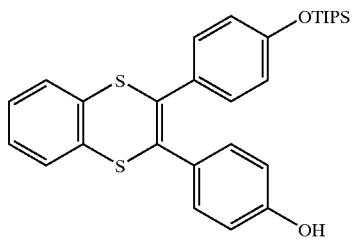

C

Using the thioketone 20ah, prepared in Example 20, 121 mg of a mixture of three products (A: B: C=1: 0.1: 0.25) was isolated after purification by silica gel chromatography with 10% EtOAc/hexane as the eluant. $^1$H 500 MHz NMR (CDCl$_3$) ppm (δ): A: 4.9 (q, 2H); B: 4.68 (d, 2H).

Example 32

Preparation of

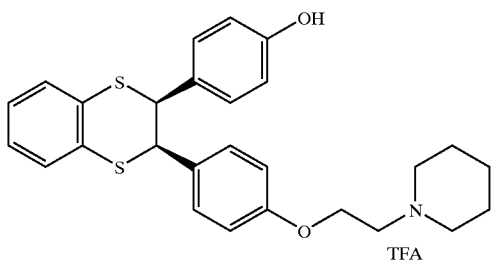

A

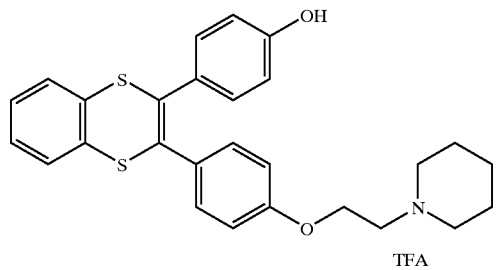

B

Step A

The dithiin mixture obtained from Example 31 was coupled with 1-piperidineethanol using the procedure described in Example 25 (Step A). After purification by silica gel chromatography using 3% MeOH/CH$_2$Cl$_2$ as eluant, the adducts were obtained as a mixture.

Step B

The adducts from Step A were desilylated using the procedure described in Example 25 (Step C). The products were separated by HPLC on a Meta Chem Polaris C-18, 4.6×50 mm reverse-phase column, at a flow rate of 4 mL/minute, with a gradient of 5 to 75% of acetonitrile in 0.1% trifluoroacetic acid. A: a white solid, $^1$H NMR (400 MHz, CD$_3$OD) δ (ppm):7.2 (m, 2H), 7.1 (m, 2H), 6.9 (m, 2H), 6.8 (m, 4H), 6.55 (d, 2H), 4.75 (m, 2H), 4.3 (m, 2H), 3.6 (br d, 2H), 3.5 (m, 2H), 3.0 (br t, 2H), 1.95 (m, 2H), 1.8 (m, 4H); (MS In/z 464 (M$^+$). B: $^1$H NMR (400 MHz, CD$_3$OD) δ (ppm): 7.4 (m, 2H), 7.3 (m, 2H), 7.1 (d, 2H), 6.95 (d, 2H), 6.8 (d, 2H), 6.6 (d, 2H), 4.3 (br s, 2H), 3.6 (br d, 2H), 3.5 (br t, 2H), 3.05 (br t, 2H), 2.0 (br d, 2H), 1.8 (m, 4H); MS m/z 462 (M$^+$).

Example 33

Preparation of

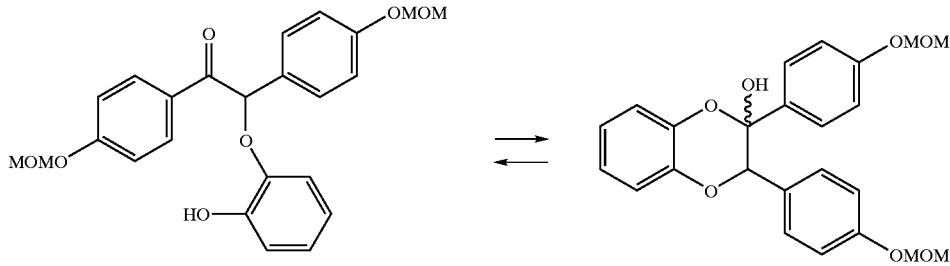

Using 1,2-dihydroxybenzene and bromide 19g, of Example 19, the product was obtained after purification by silica gel chromatography using EtOAc/hexane (1:4) as eluant, and shown to be an equilibrium mixture of the open and closed form of the adduct MS m/z 448 (M⁺+23).

Example 34

Preparation of Dihydro-Benzodioxanes

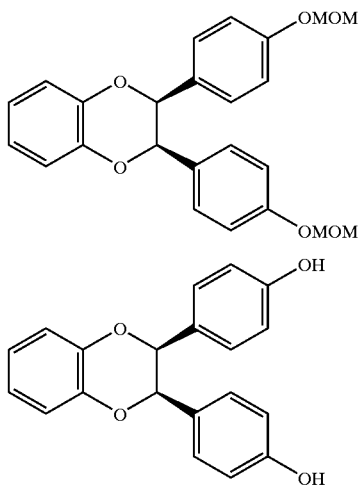

The mixture generated in Example 33 was converted to the bis-MOM protected product shown following the procedure described in Example 21, with the exception that 5 equivalents of TFA and 2 equivalents of Et₃SiH were necessary to drive the reaction to completion. The MOM groups were then removed with mild acid treatment (2N HCl, 75° C.) to give the depicted diol product. $^1$H NMR (400 MHz, CDCl₃) δ (ppm): 7.0 (m, 4H), 6.85 (d, 2H), 6.65 (d, 2H), 5.38 (s, 2H); MS m/z 343 (M⁺+23).

Example 35

Preparation of

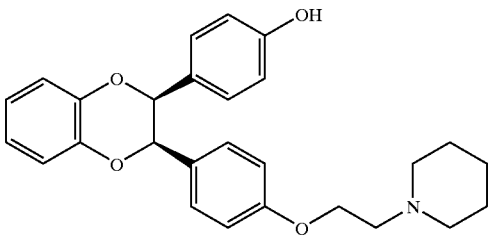

The dioxane derivative obtained from Example 34 was coupled with 1-piperidineethanol, as described in Example 25 Step A, to give the product. $^1$H NMR (400 MHz, CD₃OD) δ (ppm): 7.04 (d, 2H), 6.98–6.84 (m, 4H), 6.82 (d, 2H), 6.74 (d, 1H), 6.63 (d, 2H), 6.56 (d, 2H), 5.36 (d, 1H), 5.33 (d, J=3.0 Hz, 1H), 4.02 (m, 2H), 2.8 (m, 2H), 2.6 (br s, 4H), 1.62 (m, 4H), 1.5 (m, 2H); MS m/z 432 (M⁺).

Example 36

Preparation of 1-N-(2-Hydroxyethyl)-3-(R)-Methylpyrrolidine

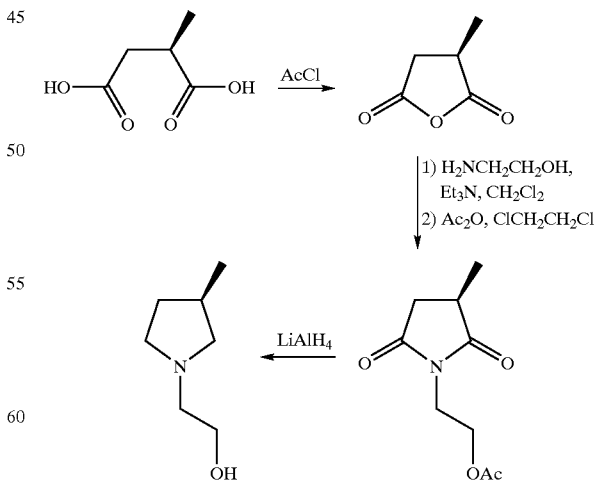

Step A: A mixture of (R)-2-methyl-succinic acid (3.30 g, 0.025 mol, Aldrich) and acetyl chloride (25 mL, Aldrich) was stirred at reflux (oil bath temperature 65° C.) for 3.5 hours. The resulting yellow solution was cooled to room temperature, diluted with toluene (50 mL) and evaporated to a yellow oil. Additional toluene (50 mL) was added and the mixture was evaporated again to a yellow oil which solidified on standing at room temperature to an off-white solid. The crude anhydride was used without purification in the next step.

Step B: The crude anhydride (2.86 g) obtained in Step A was dissolved in anhydrous dichloromethane (250 mL) then triethylamine (3.5 mL, 0.025 mol, Aldrich) and ethanolamine (1.5 mL, 0.025 mol, Aldrich) were added. The resulting mixture (initially turned cloudy then clear) was stirred at room temperature for 16 hours then evaporated to a yellow-orange syrup (10.48 g). The residue was suspended in anhydrous dichloroethane (200 mL) then acetic anhydride (11.8 mL, 1.25 mol) was added. The resulting mixture was stirred at reflux for 5 hours. The resulting solution was cooled to room temperature and transferred to a 1L Erlenmyer flask. Saturated aqueous sodium bicarbonate (250 mL) was added cautiously (in three portions) and the resulting mixture was stirred vigorously for 30 minutes. The layers were separated and the aqueous layer was extracted with dichloromethane (150 mL). The combined organic layers were dried ($MgSO_4$), filtered, and evaporated to a light yellow syrup (4.12 g). The crude product was purified by flash chromatography on silica gel eluted with 55:45 hexane:ethyl acetate ($R_f$ 0.30) to afford the imide as a colorless liquid. NMR: ($CDCl_3$, 600 MHz) δ 4.20–4.26 (2H, m, $H_2$′), 3.73–3.78 (2H, m, $H_1$′), 2.91 (1H, dd, J=18,9 Hz, $H_{4\square}$), 2.83–2.88 (1H, m, $H_3$), 2.31 (1H, dd, J=18, 4 Hz, $H_4$′), 2.00 (3H, s, OAc), 1.34 (1H, d, J=7 Hz, $CH_3$). MS (electrospray): m/e 222 (M+Na).

Step C: Lithium aluminum hydride (1.83 g, 0.048 mol) was added to a cold (ice bath) solution of the imide obtained in Step B (3.20 g, 0.016 mol) in anhydrous ether (250 mL). The cold bath was removed and the resulting mixture was stirred at room temperature for 16.5 hours. The resulting mixture was cooled in an ice bath as water (1.8 mL) was added slowly dropwise (CAUTION: vigorous reaction, gas evolution) followed by 15% NaOH (1.8 mL) and additional water (5.5 mL). The resulting mixture was stirred vigorously for 15 minutes then sonicated for 15 minutes and filtered. The collected solid was washed with ether (2×125 mL; stirred vigorously for 15 minutes then sonicated 15 minutes and filtered) and the combined filtrates were dried ($MgSO_4$), filtered, and evaporated to a light yellow oil. The crude product was purified by Kugelrohr distillation @ 7 mm Hg to afford the pure product as a colorless liquid. NMR: ($CDCl_3$, 600 MHz) δ 3.60 (2H, t, J=6 Hz, $H_2$′), 2.82 (1H, dd, J=9, 8 Hz, $H_{2a}$), 2.66–2.72 & 2.50–2.55 (2H, 2 m, $H_5$), 2.58–2.62 & 2.62–2.66 (2H, 2 m, $H_1$′), 2.20–2.28 (1H, m, $H_3$), 2.09 (1H, dd, J=9, 7 Hz, $H_{2b}$), 1.97–2.04 & 1.31–1.38 (2H, 2 m, $H_4$), 1.02 (1H, d, J=7 Hz, $CH_3$). MS (electrospray): m/e 130 (M+H). $[α]_D$ −2.6°

Pharmaceutical Composition

As a specific embodiment of this invention, 25 mg of the compound 25aa, from Example 25, is formulated with sufficient finely divided lactose to provide a total amount of 580 to 590 mg to fill a size 0, hard-gelatin capsule.

What is claimed is:
1. A compound of the formula:

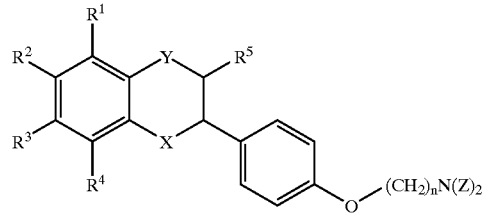

wherein
$R^1$ is selected from the group consisting of hydrogen, $C_{1-5}$ alkyl, $C_{3-8}$ cycloalkyl, $C_{2-5}$ alkenyl, $C_{2-5}$ alkynyl, $C_{3-8}$ cycloalkenyl, phenyl, heteroaryl, heterocyclyl, $CF_3$, —$OR^6$, halogen, $C_{1-5}$ alkylthio, thiocyanato, cyano, —$CO_2H$, —$COOC_{1-5}$ alkyl, —$COC_{1-5}$ alkyl, —$CONZ_2$, —$SO_2NZ_2$, and —$SO_2C_{1-5}$ alkyl, wherein said alkyl, alkenyl, alkynyl, cycloalkyl, cycloalkenyl, phenyl, heteroaryl and heterocyclyl can be optionally substituted with $C_{1-5}$ alkyl, $C_{3-8}$ cycloalkyl, $CF_3$, phenyl, heteroaryl, heterocyclyl, —$OR^6$, halogen, amino, $C_{1-5}$ alkylthio, thiocyanato, cyano, —$CO_2H$, —$COOC_{1-5}$ alkyl, —$COC_{1-5}$ alkyl, —$CONZ_2$, —$SO_2NZ_2$ or —$SO_2C_{1-5}$ alkyl;

$R^2$ is selected from the group consisting of hydrogen, $C_{1-5}$ alkyl, $C_{3-8}$ cycloalkyl, $C_{2-5}$ alkenyl, $C_{2-5}$ alkynyl, $C_{3-8}$ cycloalkenyl, phenyl, heteroaryl, heterocyclyl, $CF_3$, —$OR^6$, halogen, $C_{1-5}$ alkylthio, thiocyanato, cyano, —$CO_2H$, —$COOC_{1-5}$ alkyl, —$COC_{1-5}$ alkyl, —$CONZ_2$, —$SO_2NZ_2$, and —$SO_2C_{1-5}$ alkyl, wherein said alkyl, alkenyl, alkynyl, cycloalkyl, cycloalkenyl, phenyl, heteroaryl and heterocyclyl can be optionally substituted with $C_{1-5}$ alkyl, $C_{3-8}$ cycloalkyl, $CF_3$, phenyl, heteroaryl, heterocyclyl, —$OR^6$, halogen, amino, $C_{1-5}$ alkylthio, thiocyanato, cyano, —$CO_2H$, —$COOC_{1-5}$ alkyl, —$COC_{1-5}$ alkyl, —$CONZ_2$, —$SO_2NZ_2$ or —$SO_2C_{1-5}$ alkyl;

$R^3$ is selected from the group consisting of hydrogen, $C_{1-5}$ alkyl, $C_{3-8}$ cycloalkyl, $C_{2-5}$ alkenyl, $C_{2-5}$ alkynyl, $C_{3-8}$ cycloalkenyl, phenyl, heteroaryl, heterocyclyl, $CF_3$, —$OR^6$, halogen, $C_{1-5}$ alkylthio, thiocyanato, cyano, —$CO_2H$, —$COOC_{1-5}$ alkyl, —$COC_{1-5}$ alkyl, —$CONZ_2$, —$SO_2NZ_2$, and —$SO_2C_{1-5}$ alkyl, wherein said alkyl, alkenyl, alkynyl, cycloalkyl, cycloalkenyl, phenyl, heteroaryl and heterocyclyl can be optionally substituted with $C_{1-5}$ alkyl, $C_{3-8}$ cycloalkyl, $CF_3$, phenyl, heteroaryl, heterocyclyl, —$OR^6$, halogen, amino, $C_{1-5}$ alkylthio, thiocyanato, cyano, —$CO_2H$, —$COOC_{1-5}$ alkyl, —$COC_{1-5}$ alkyl, —$CONZ_2$, —$SO_2NZ_2$ or —$SO_2C_{1-5}$ alkyl;

$R^4$ is selected from the group consisting of hydrogen, $C_{1-5}$ alkyl, $C_{3-8}$ cycloalkyl, $C_{2-5}$ alkenyl, $C_{2-5}$ alkynyl, $C_{3-8}$ cycloalkenyl, phenyl, heteroaryl, heterocyclyl, $CF_3$, —$OR^6$, halogen, $C_{1-5}$ alkylthio, thiocyanato, cyano, —$CO_2H$, —$COOC_{1-5}$ alkyl, —$COC_{1-5}$ alkyl, —$CONZ_2$, —$SO_2NZ_2$, and —$SO_2C_{1-5}$ alkyl, wherein said alkyl, alkenyl, alkynyl, cycloalkyl, cycloalkenyl, phenyl, heteroaryl and heterocyclyl can be optionally substituted with $C_{1-5}$ alkyl, $C_{3-8}$ cycloalkyl, $CF_3$, phenyl, heteroaryl, heterocyclyl, —$OR^6$, halogen, amino, $C_{1-5}$ alkylthio, thiocyanato, cyano, —$CO_2H$, —$COOC_{1-5}$ alkyl, —$COC_{1-5}$ alkyl, —$CONZ_2$, —$SO_2NZ_2$ or —$SO_2C_{1-5}$ alkyl;

$R^5$ is selected from the group consisting of $C_{1-5}$ alkyl, $C_{3-8}$ cycloalkyl, $C_{2-5}$ alkenyl, $C_{2-5}$ alkynyl, $C_{3-8}$ cycloalkenyl, phenyl, heteroaryl and heterocyclyl, wherein said alkyl, cycloalkyl, alkenyl, alkynyl, cycloalkenyl, phenyl, heteroaryl and heterocyclyl can be optionally substituted with $C_{1-5}$ alkyl, $C_{3-8}$ cycloalkyl, $CF_3$, phenyl, heteroaryl, heterocyclyl, —$OR^6$, halogen, amino, $C_{1-5}$ alkylthio, thiocyanato, cyano, —$CO_2H$, —$COOC_{1-5}$ alkyl, —$COC_{1-5}$ alkyl, —$CONZ_2$, —$SO_2NZ_2$ or —$SO_2C_{1-5}$ alkyl;

X and Y are each independently selected from the group consisting of oxygen, sulfur, sulfoxide and sulfone;

$R^6$ is selected from the group consisting of hydrogen, $C_{1-5}$ alkyl, benzyl, methoxymethyl, triorganosilyl, $C_{1-5}$ alkylcarbonyl, alkoxycarbonyl and $CONZ_2$;

each Z is independently selected from the group consisting of hydrogen, $C_{1-5}$ alkyl, and trifluoromethyl, wherein said alkyl can be optionally substituted with $C_{1-5}$ alkyl, $CF_3$, —$OR^6$, halogen, amino, $C_{1-5}$ alkylthio, thiocyanato, cyano, —$CO_2H$, —$COOC_{1-5}$ alkyl, —$COC_{1-5}$ alkyl, —$CONV_2$, —$SO_2NV_2$ or —$SO_2C_{1-5}$ alkyl;

both Zs and the nitrogen to which they are attached may be taken together to form a 3–8 membered ring, said ring may optionally contain atoms selected from the group consisting of carbon, oxygen, sulfur, and nitrogen, wherein said ring may either be saturated or unsaturated, and the carbon atoms of said ring maybe optionally substituted with one to three substituents selected from the group consisting of $C_{1-5}$ alkyl, $CF_3$, —$OR^6$, halogen, amino, $C_{1-5}$ alkylthio, thiocyanato, cyano, —$CO_2H$, —$COOC_{1-5}$ alkyl, —$COC_{1-5}$ alkyl, —$CONV_2$, —$SO_2NV_2$, and —$SO_2C_{1-5}$ alkyl;

each V is independently selected from the group consisting of $C_{1-5}$ alkyl, $CF_3$, —$OR^6$, halogen, amino, $C_{1-5}$ alkylthio, thiocyanato, cyano, —$CO_2H$, —$COOC_{1-5}$ alkyl, —$COC_{1-5}$ alkyl, and —$SO_2C_{1-5}$ alkyl;

n is independently an integer from one to five;

or a pharmaceutically acceptable salt or stereoisomer thereof.

2. The compound of claim 1 wherein Y is sulfur and X is oxygen, or a pharmaceutically acceptable salt or stereoisomers thereof.

3. The compound of claim 2 wherein $R^1$ is selected from the group consisting of hydrogen, $C_{1-5}$ alkyl, $C_{3-8}$ cycloalkyl, $C_{2-5}$ alkenyl, $C_{2-5}$ alkynyl, —$OR^6$ and halogen, provided that one of $R^2$ and $R^3$ is —OH;

$R^2$ is selected from the group consisting of hydrogen, $C_{1-5}$ alkyl, $C_{3-8}$ cycloalkyl, $C_{2-5}$ alkenyl, $C_{2-5}$ alkynyl, —$OR^6$ and halogen, provided that one of $R^2$ and $R^3$ is —OH;

$R^3$ is selected from the group consisting of hydrogen, $C_{1-5}$ alkyl, $C_{3-8}$ cycloalkyl, $C_{2-5}$ alkenyl, $C_{2-5}$ alkynyl, —$OR^6$ and halogen, provided that one of $R^2$ and $R^3$ is —OH;

$R^4$ is selected from the group consisting of hydrogen, $C_{1-5}$ alkyl, $C_{3-8}$ cycloalkyl, $C_{2-5}$ alkenyl, $C_{2-5}$ alkynyl, —$OR^6$ and halogen, provided that one of $R^2$ and $R^3$ is —OH;

$R^5$ is selected from the group consisting of $C_{3-8}$ cycloalkyl, phenyl, heteroaryl and heterocyclyl wherein said cycloalkyl, phenyl, heteroaryl and heterocyclyl can be optionally substituted with —$OR^6$ or halogen;

$R^6$ is selected from the group consisting of hydrogen, $C_{1-5}$ alkyl, benzyl, methoxymethyl and triisopropylsilyl;

or a pharmaceutically acceptable salt or stereoisomer thereof.

4. The compound of claim 3 of the formula:

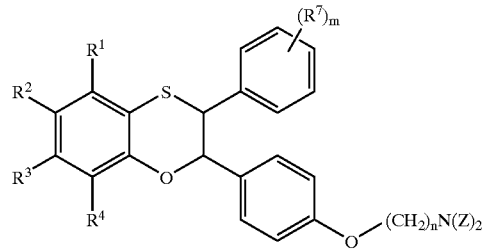

wherein $R^7$ is selected from the group consisting of hydrogen, halogen, and —$OR^6$;

m is an integer from one to three;

or a pharmaceutically acceptable salt or stereoisomer thereof.

5. The compound of claim 4 of the formula:

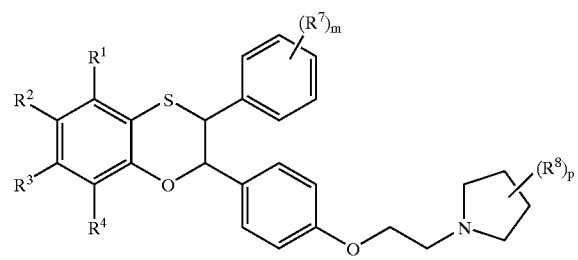

wherein each $R^8$ is independently selected from the group consisting of hydrogen, $C_{1-5}$ alkyl, $CF_3$, —$OR^6$, halogen, amino, $C_{1-5}$ alkylthio, thiocyanato, cyano, —$CO_2H$, —$COOC_{1-5}$ alkyl, —$COC_{1-5}$ alkyl, —$CONV_2$, —$SO_2NV_2$, and —$SO_2C_{1-5}$ alkyl;

p is an integer from one to three;

or a pharmaceutically acceptable salt or stereoisomer thereof.

6. The compound of claim 4 of the formula:

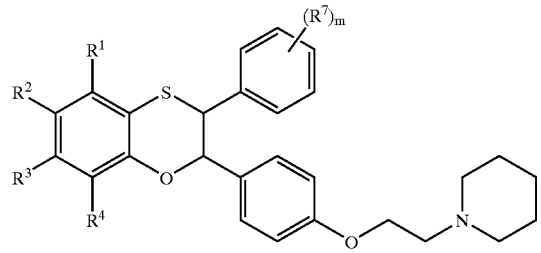

wherein m is an integer from one or two; ps or a pharmaceutically acceptable salt or stereoisomer thereof.

7. The compound of claim 1 wherein X is sulfur and Y is sulfur, or a pharmaceutically acceptable salt or stereoisomer thereof.

8. The compound of claim 3 which is:
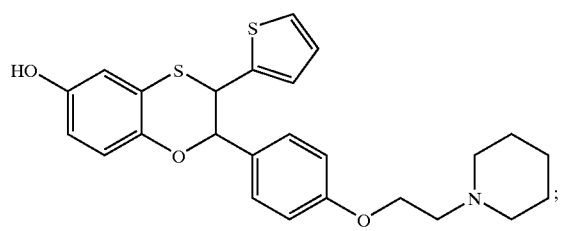
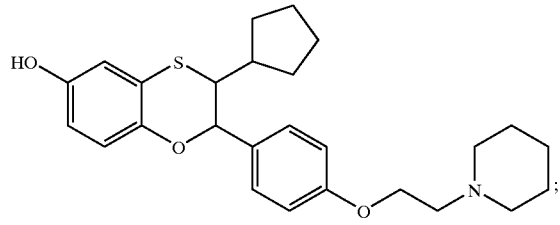
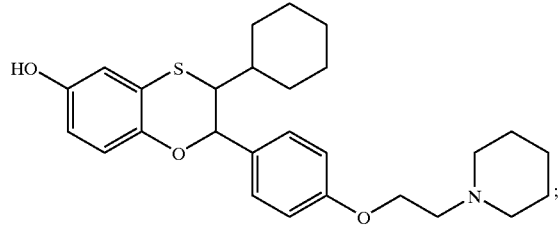
or a pharmaceutically acceptable salt or stereoisomer thereof.
9. The compound of claim 4 which is:
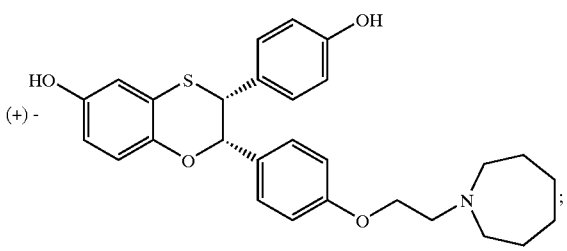
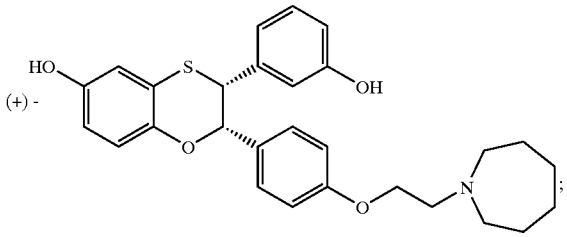
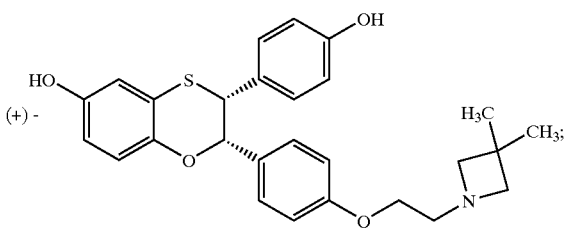
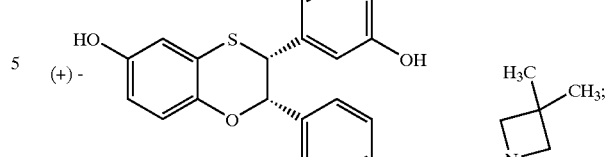
or a pharmaceutically acceptable salt or stereoisomer thereof.
10. The compound of claim 4 which is:
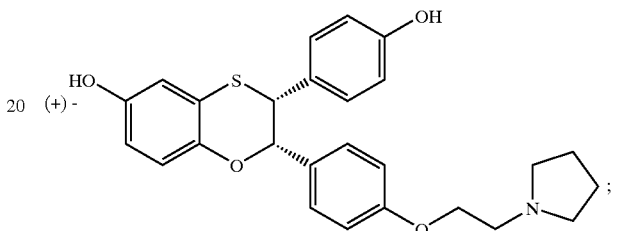
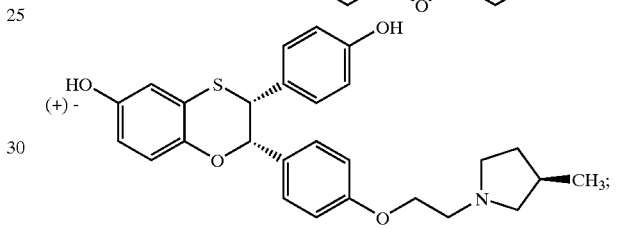
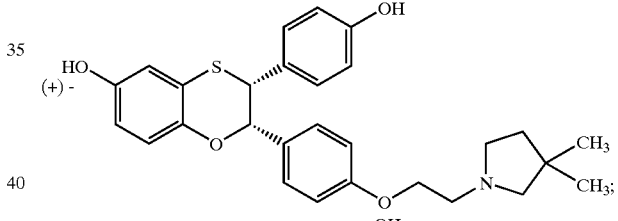
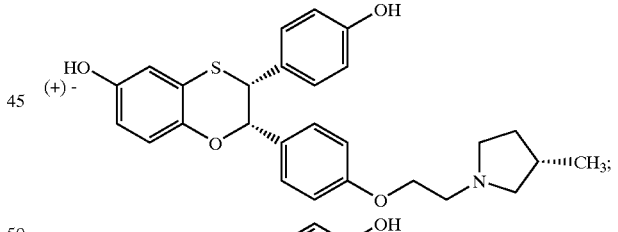
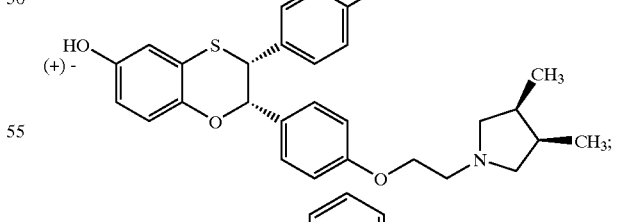
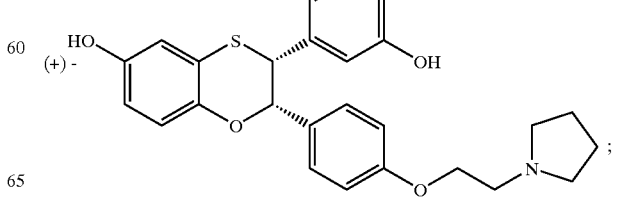

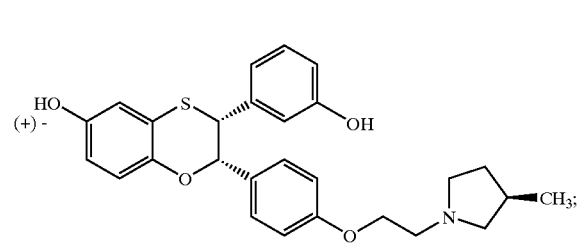
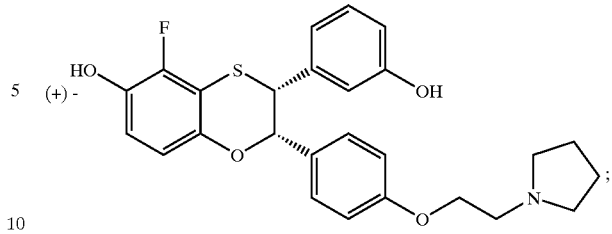
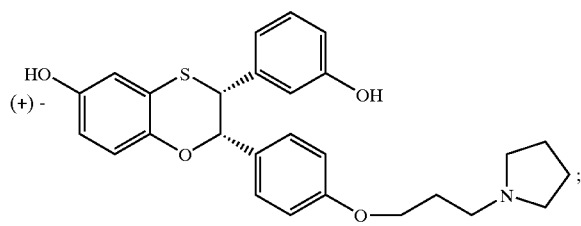
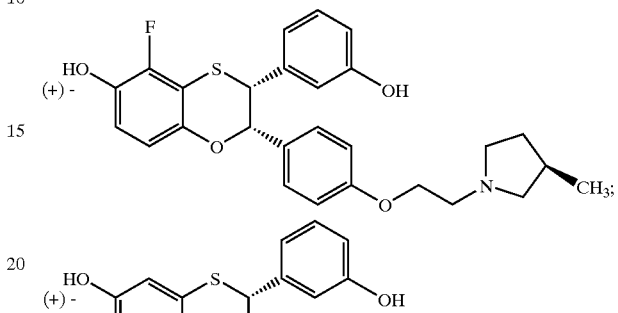
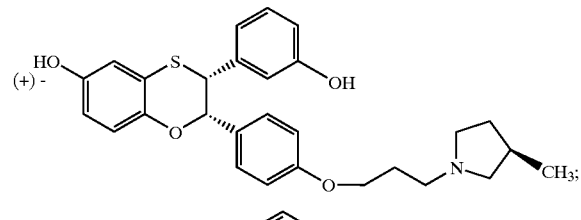
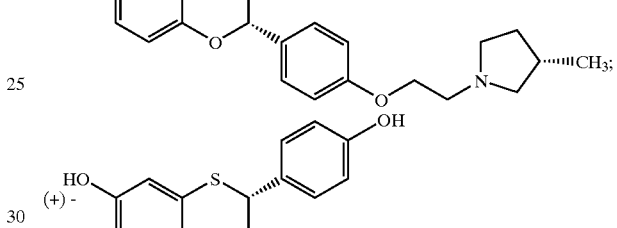
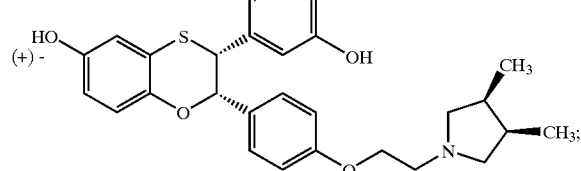
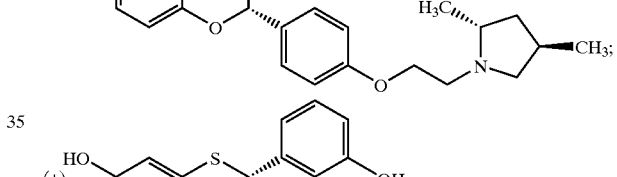
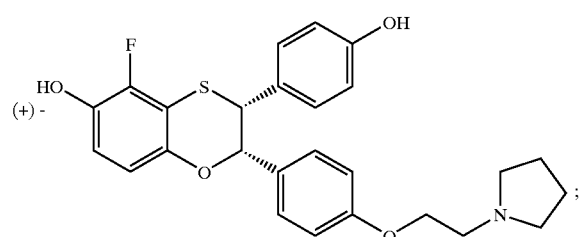
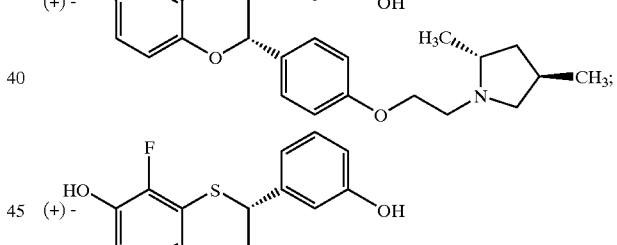
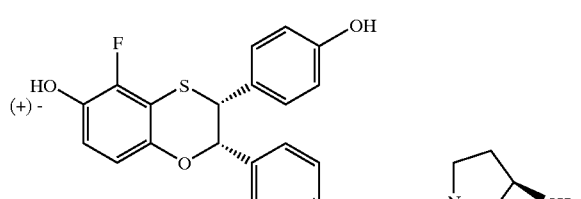
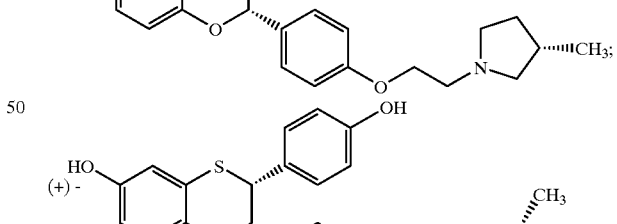
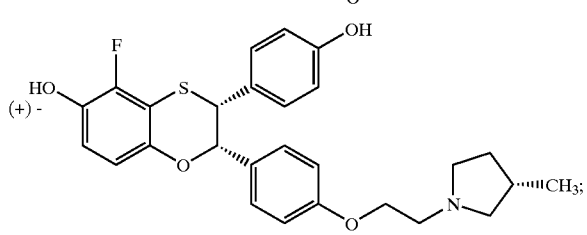
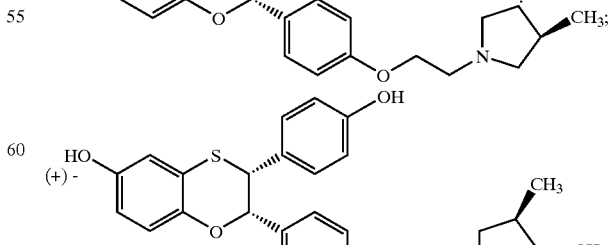

113
-continued
(+)- 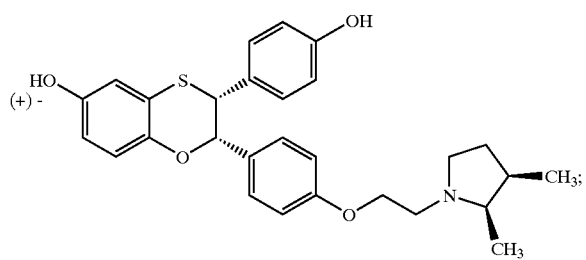
(+)- 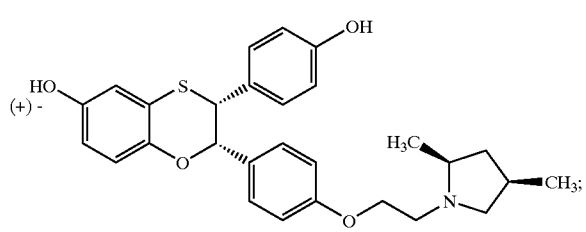
(+)- 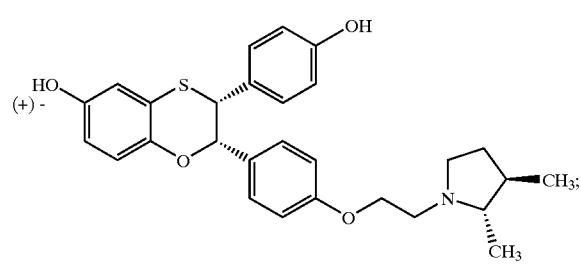
(+)- 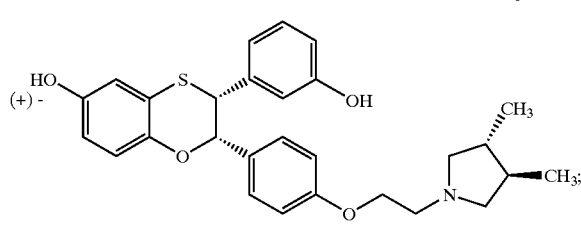
(+)- 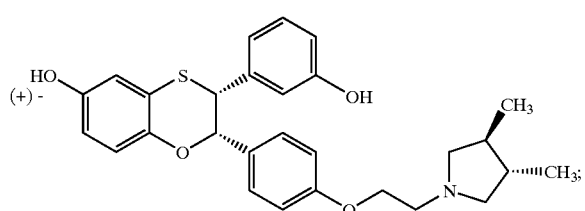
(+)- 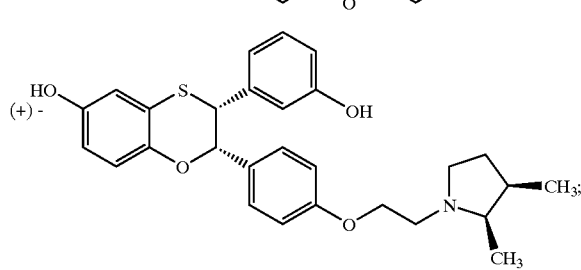
(+)- 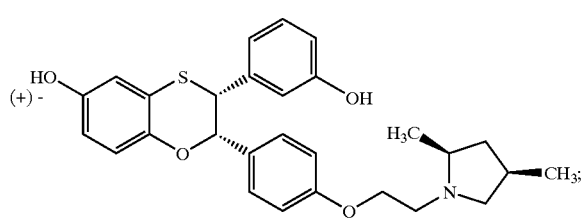
114
-continued
(+)- 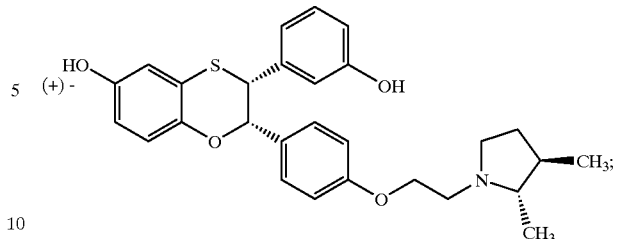
(+)- 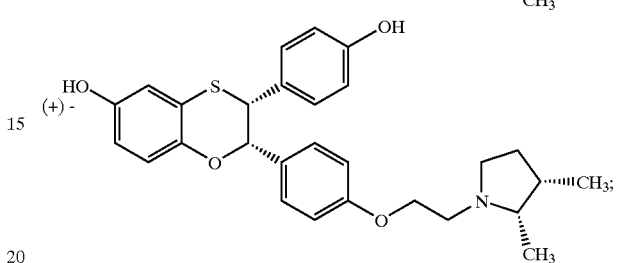
(+)- 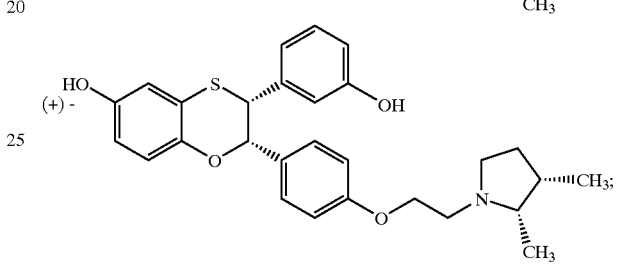
(+)- 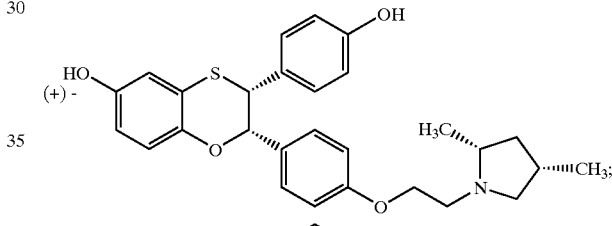
(+)- 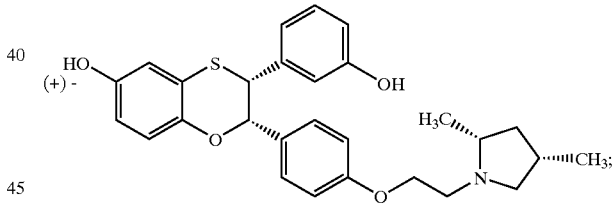
(+)- 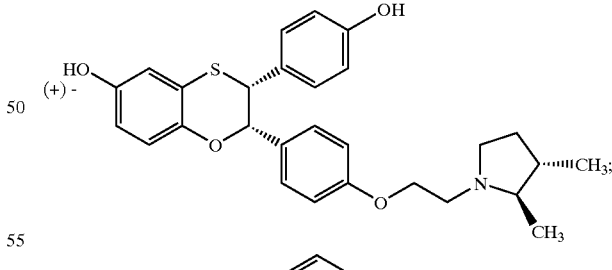
(+)- 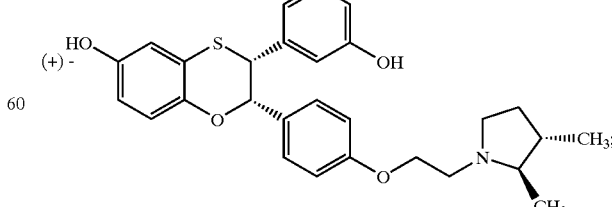

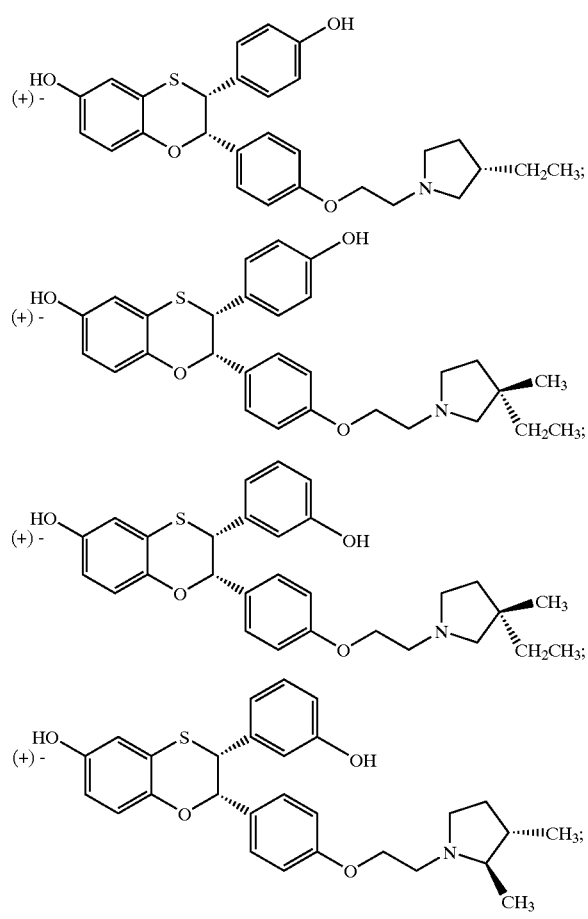
or a pharmaceutically acceptable salt or stereoisomer thereof.
11. The compound of claim 5 which is:
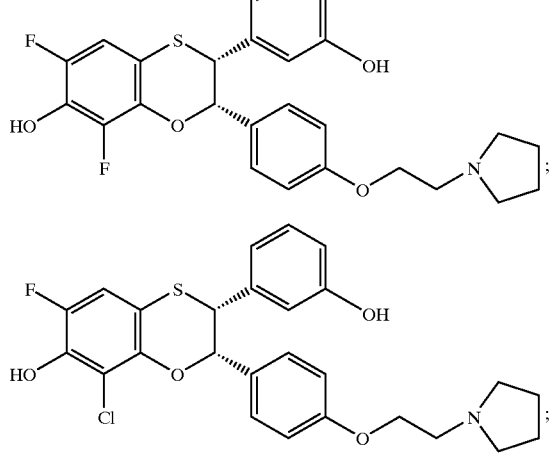
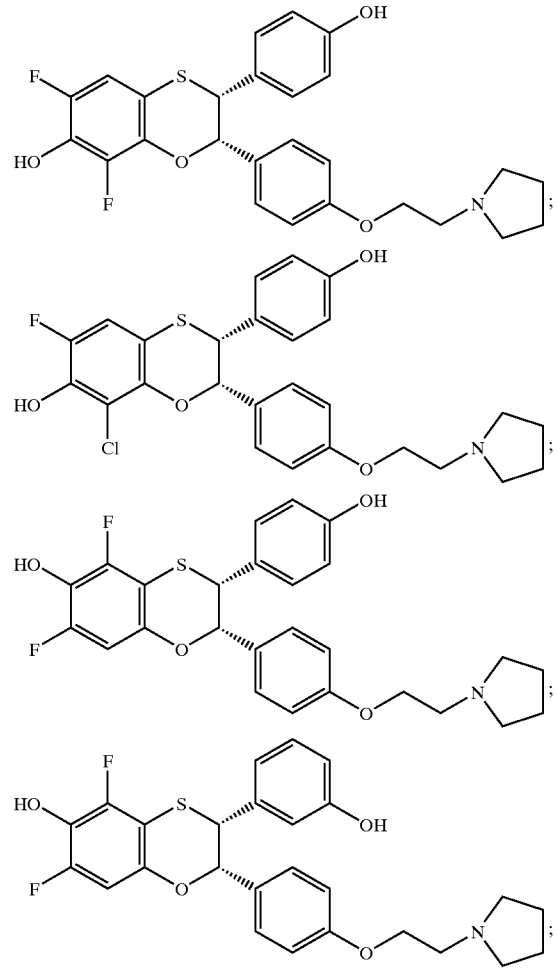
or a pharmaceutically acceptable salt or steroisomer thereof.
12. The compound of claim 10 of the formula
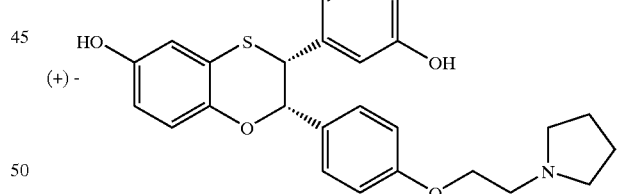
or a pharmaceutically acceptable salt or stereoisomer thereof.
13. The compound of claim 10 of the formula
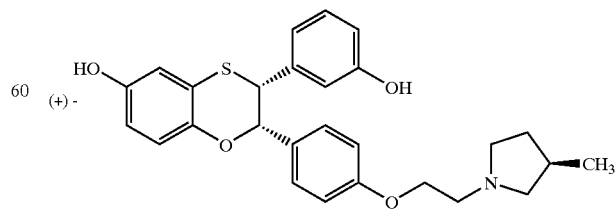

or a pharmaceutically acceptable salt or stereoisomer thereof.

14. The compound of claim 10 of the formula

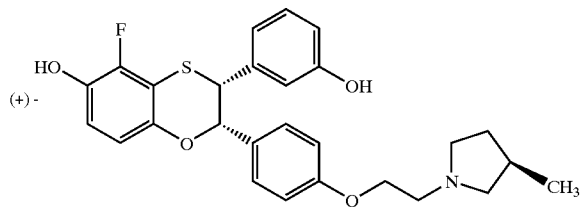

or a pharmaceutically acceptable salt or stereoisomer thereof.

15. The compound of claim 10 of the structure

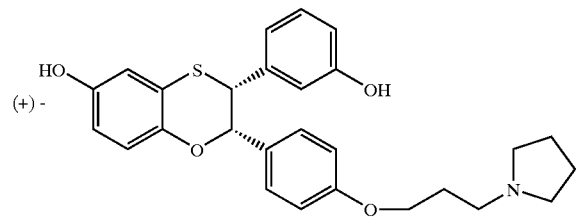

or a pharmaceutically acceptable salt or stereoisomer thereof.

16. The compound of claim 10 of the structure

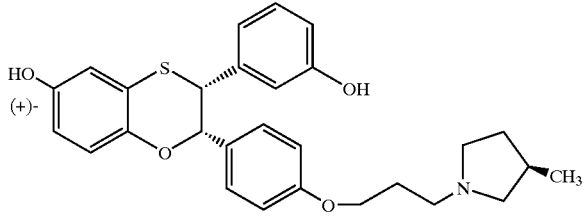

or a pharmaceutically acceptable salt or stereoisomer thereof.

17. The compound of claim 6 which is:

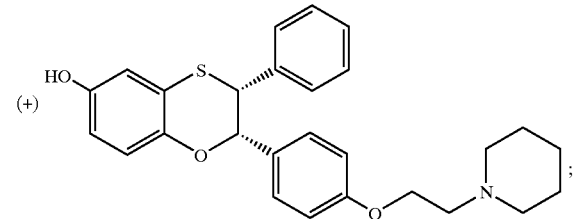

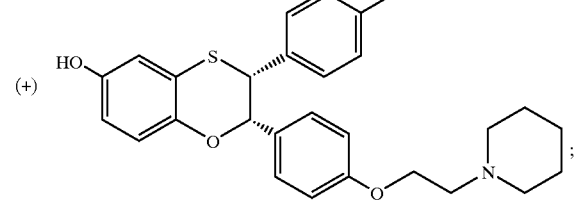

-continued

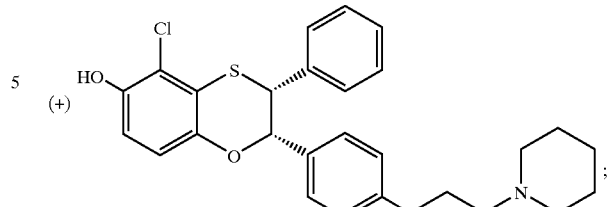

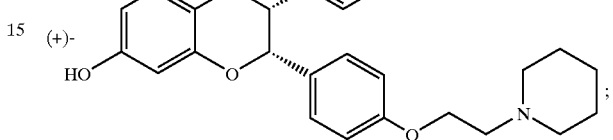

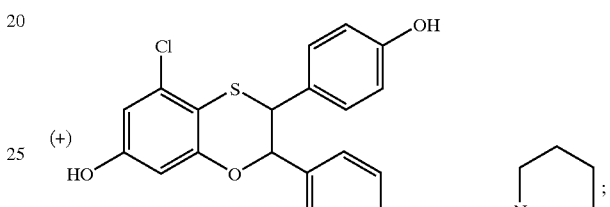

or a pharmaceutically acceptable salt or stereoisomer thereof.

18. The compound of claim 6 which is:

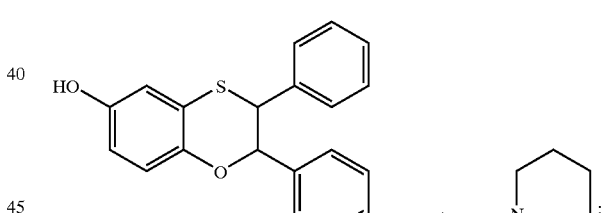

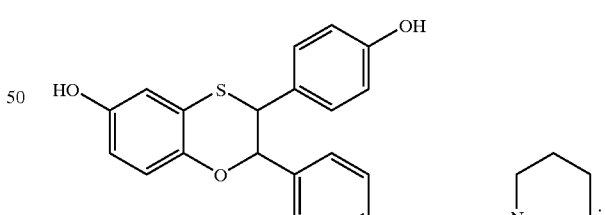

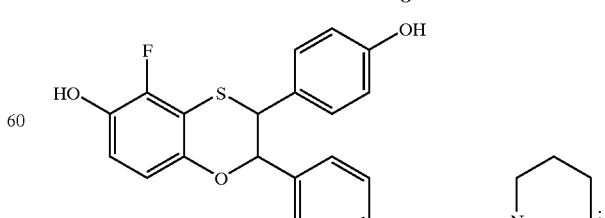

121
-continued
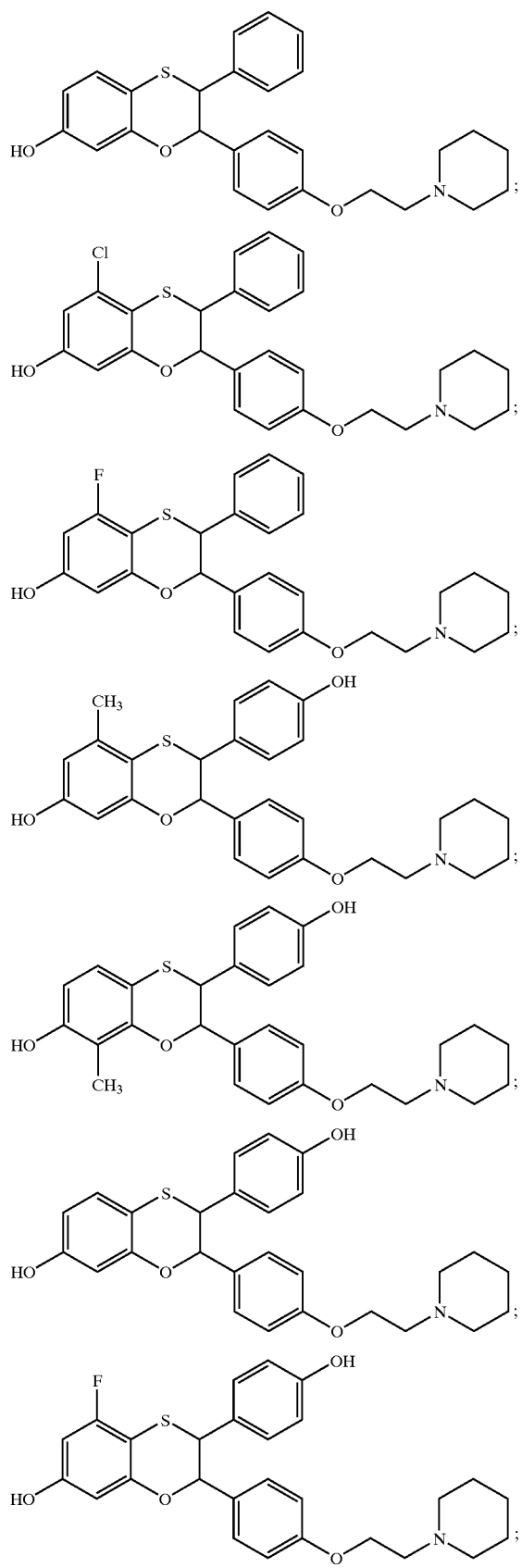
122
-continued
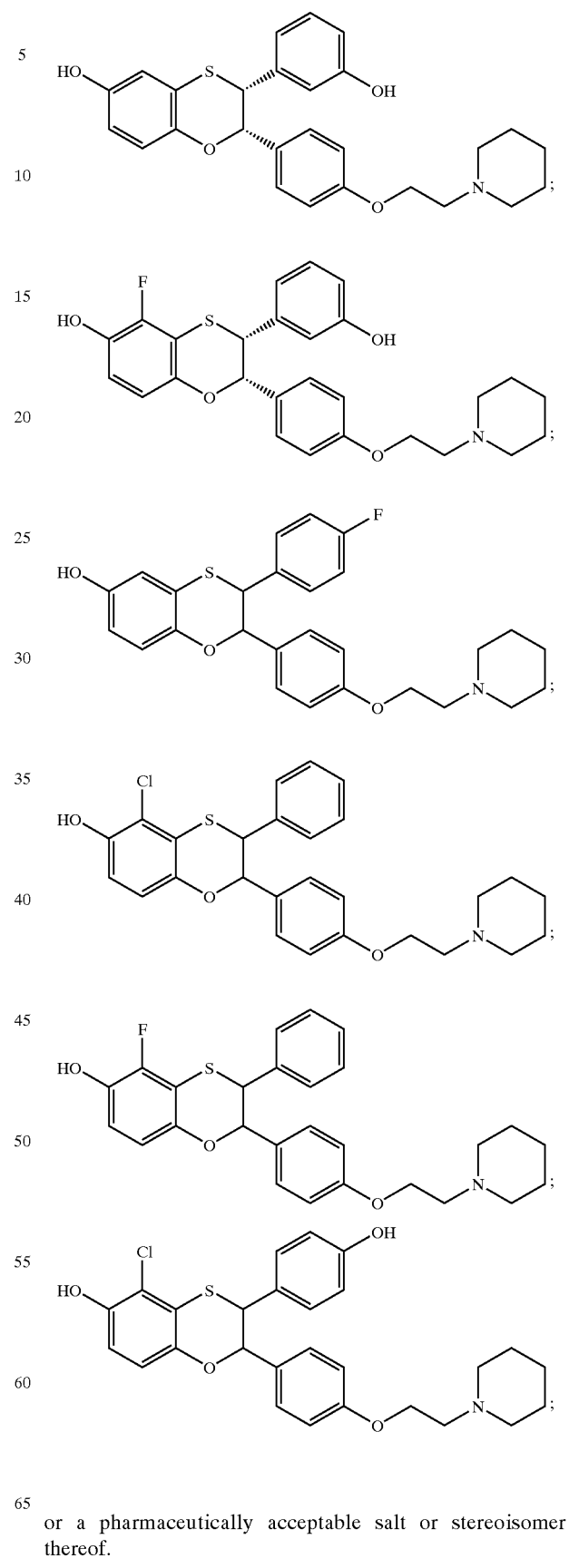
or a pharmaceutically acceptable salt or stereoisomer thereof.

19. The compound of claim 17 of the structure

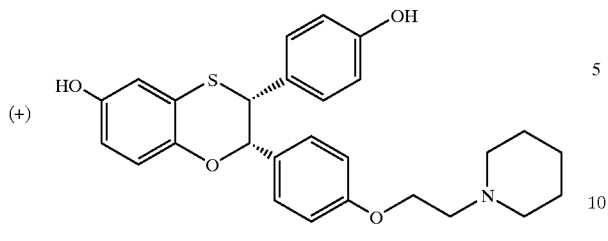

or a pharmaceutically acceptable salt or stereoisomer thereof.

20. The compound of claim 17 of the structure

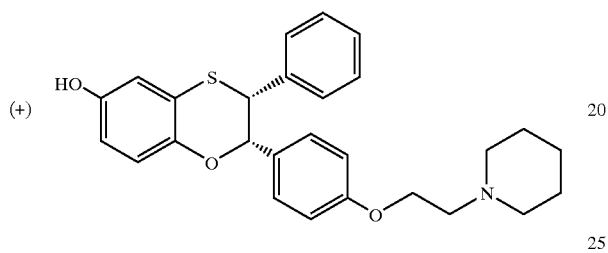

or a pharmaceutically acceptable salt or stereoisomer thereof.

21. The compound of claim 17 of the structure

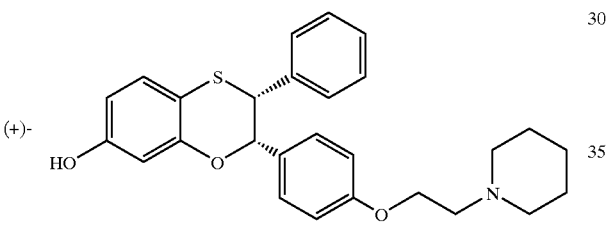

or a pharmaceutically acceptable salt or stereoisomer thereof.

22. The compound according to claim 7 which is:

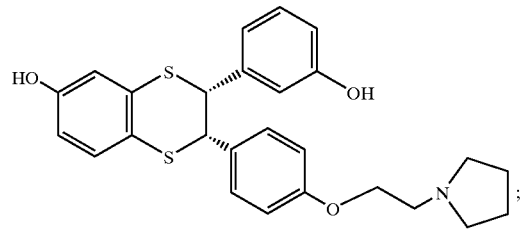

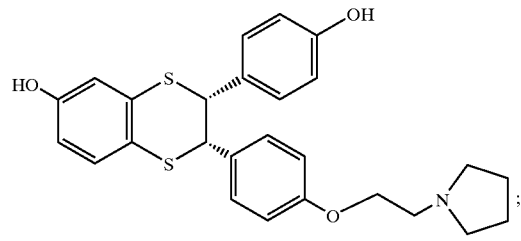

or a pharmaceutically acceptable salt or stereoisomer thereof.

23. A pharmaceutical composition comprising a compound according to claim 1 and a pharmaceutically acceptable carrier.

24. A pharmaceutical composition made by combining a compound according to claim 1 and a pharmaceutically acceptable carrier.

* * * * *